US009023637B2

(12) United States Patent
Dai et al.

(10) Patent No.: US 9,023,637 B2
(45) Date of Patent: May 5, 2015

(54) **ENHANCED CITRIC ACID PRODUCTION IN *ASPERGILLUS* WITH INACTIVATED ASPARAGINE-LINKED GLYCOSYLATION PROTEIN 3 (ALG3), AND/OR INCREASED LAEA EXPRESSION**

(71) Applicant: Battelle Memorial Institute, Richland, WA (US)

(72) Inventors: Ziyu Dai, Richland, WA (US); Scott E. Baker, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 176 days.

(21) Appl. No.: 13/691,396

(22) Filed: Nov. 30, 2012

(65) Prior Publication Data

US 2013/0137150 A1    May 30, 2013

Related U.S. Application Data

(60) Provisional application No. 61/565,018, filed on Nov. 30, 2011.

(51) Int. Cl.
| | |
|---|---|
| C12N 1/15 | (2006.01) |
| C12P 7/48 | (2006.01) |
| C12N 1/14 | (2006.01) |
| C12N 9/10 | (2006.01) |
| C12N 15/00 | (2006.01) |
| C12P 21/00 | (2006.01) |
| C07H 21/00 | (2006.01) |

(52) U.S. Cl.
CPC ... *C12P 7/48* (2013.01); *C12N 1/14* (2013.01); *C12N 9/1051* (2013.01); *C12Y 204/01258* (2013.01)

(58) Field of Classification Search
CPC   C12P 7/48; C12Y 204/01258; C12N 9/1051; C12N 1/14
USPC .............. 435/254.11, 254.3, 144, 193, 320.1, 435/69.1; 536/23.2
See application file for complete search history.

(56) References Cited

U.S. PATENT DOCUMENTS

| | | | |
|---|---|---|---|
| 5,532,148 | A | 7/1996 | Datta et al. |
| 2004/0058872 | A1 | 3/2004 | Keller et al. |
| 2010/0062485 | A1 * | 3/2010 | Kang et al. .................. 435/69.1 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Sousa et al., Microbiology 148(Pt5):1291-1303, 2002.*
Zhou et al., Cell Mol Life Sci 63(19-20):2260-2290, 2006.*
Kozak, M., Gene 234:187-208, 1999.*
Uniprot ALG3_ASPNC [online] Nov. 2, 2010 [retrieved Jan. 9, 2013], available on the internet <URL: www.uniprot.org/uniprot/A2RA94.txt?version=27>.
Pel et al., "Genome Sequencing and Analysis of the Versatile Cell Factory *Aspergillus niger* CBS 513.88," *Nature Biotechnol.* 25:221-231, 2007.
Aebi et al., "Cloning and Characterization of the *ALG3* Gene of *Saccharomyces cerevisiae*," *Glycobiol.* 6:439-444, 1996.
Andersen et al., "Comparative Genomics of Citric-Acid-Producing *Aspergillus niger* ATCC 1015 Versus Enzyme-Producing CBS 513.88," *Genome Res.* 21:885-897, 2011.
Apweiler et al., "On the Frequency of Protein Glycosylation, as Deduced from Analysis of the SWISS-PROT Database," *Biochim. Biophys. Acta* 1473:4-8, 1999.
Baba et al., "Identification and Characterization of *Penicillium citrinum* VeA and LaeA as Global Regulators for ML-236B Production," *Curr. Genet.* 58:1-11, 2012.
Bayram et al., "Ve1B/VeA/LaeA Complex Coordinates Light Signal with Fungal Development and Secondary Metabolism," *Science* 320:1504-1506, 2008.
Bayram et al., "LaeA Control of Velvet Family Regulatory Proteins for Light-Dependent Development and Fungal Cell-Type Specificity," *PLoS Genet.* 6:e1001226, 2010.
Bok and Keller, "LaeA, a Regulator of Secondary Metabolism in *Aspergillus* spp.," *Eukaryot. Cell* 3:527-535, 2004.
Bok et al., "Secondary Metabolic Gene Cluster Silencing in *Aspergillus nidulans*," *Mol. Microbiol.* 61:1636-1645, 2006.
Bok et al., "Chromatin-Level Regulation of Biosynthetic Gene Clusters," *Nat. Chem. Biol.* 5:462-464, 2009.
Bouhired et al., "Accurate Prediction of the *Aspergillus nidulans* Terrequinone Gene Cluster Boundaries Using the Transcriptional Regulator LaeA," *Fungal Genet. Biol.* 44:1134-1145, 2007.
Bowman et al., "Mutational Analysis of the Glycosylphosphatidylinositol (GPI) Anchor Pathway Demonstrates that GPI-Anchored Proteins Are Required for Cell Wall Biogenesis and Normal Hyphal Growth in *Neurospora crassa*," *Eukaryot. Cell* 5:587-600, 2006.
Butchko et al., "Lael Regulates Expression of Multiple Secondary Metabolite Gene Clusters in *Fusarium verticillioides*," *Fungal Genet. Biol.* 49:602-612, 2012.
Calvo, "The VeA Regulatory System and its Role in Morphological and Chemical Development in Fungi," *Fungal Genet. Biol.* 45:1053-1061, 2008.
Davidson et al., "Functional Analysis of the *ALG3* Gene Encoding the Dol-P-Man: Man$_5$GlcNAc$_2$-PP-Dol Mannosyltransferase Enzyme of *P. pastoris*," *Glycobiology* 14:399-407, 2004.

(Continued)

*Primary Examiner* — Delia Ramirez
(74) *Attorney, Agent, or Firm* — Klarquist Sparkman, LLP

(57) ABSTRACT

Provided herein are fungi, such as *Aspergillus niger*, having a dolichyl-P-Man:Man(5)GlcNAc(2)-PP-dolichyl mannosyltransferase (Alg3) gene genetic inactivation, increased expression of a loss of aflR expression A (Lae), or both. In some examples, such mutants have several phenotypes, including an increased production of citric acid relative to the parental strain. Methods of using the disclosed fungi to make citric acid are also provided, as are compositions and kits including the disclosed fungi.

20 Claims, 18 Drawing Sheets

(56) References Cited

OTHER PUBLICATIONS

Dellaporta et al., "A Plant DNA Minipreparation: Version II," *Plant Mol. Biol. Rep.* 1:19-21, 1983.
Denecke et al., "Congenital Disorder of Glycosylation Type Id: Clinical Phenotype, Molecular Analysis, Prenatal Diagnosis, and Glycosylation of Fetal Proteins," *Pediatr. Res.* 58:248-253, 2005.
de Oliveira and de Graaff, "Proteomics of Industrial Fungi: Trends and Insights for Biotechnology," *Appl. Microbiol. Biotechnol.* 89:225-237, 2011.
Deshpande et al., "Protein Glycosylation Pathways in Filamentous Fungi," *Glycobiology* 18:626-637, 2008.
Georgianna et al., "Beyond Aflatoxin: Four Distinct Expression Patterns and Functional Roles Associated with *Aspergillus flavus* Secondary Metabolism Gene Clusters," *Mol. Plant Pathol.* 11:213-226, 2010.
Gerngross, "Advances in the Production of Human Therapeutic Proteins in Yeasts and Filamentous Fungi," *Nat. Biotechnol.* 22:1409-1414, 2004.
Geysens et al., "Genomics of Protein Folding in the Endoplasmic Reticulum, Secretion Stress and Glycosylation in the Aspergilli," *Fungal Genet. Biol.* 46:S121-S140, 2009.
Haltiwanger and Lowe, "Role of Glycosylation in Development," *Ann. Rev. Biochem.* 73:491-537, 2004.
Jacobs et al., "Effective Lead Selection for Improved Protein Production in *Aspergillus niger* Based on Integrated Genomics," *Fungal Genet. Biol.* 46:S141-S152, 2009.
Kainz et al., "N-Glycan Modification in *Aspergillus Species,*" *Appl. Environ. Microbiol.* 74:1076-1086, 2008.
Kale et al., "Requirement of LaeA for Secondary Metabolism and Sclerotial Production in *Aspergillus flavus,*" *Fungal Genet. Biol.* 45:1422-1429, 2008.
Kajiura et al.,"*Arabidopsis thaliana* ALG3 Mutant Synthesizes Immature Oligosaccharides in the ER and Accumulates Unique N-Glycans," *Glycobiology* 20:736-7 51,2010.
Keller et al., "LaeA, A Global Regulator of *Aspergillus* Toxins," *Med. Mycol.* 44:S83-S85, 2006.
Kim et al., "Centralized Modularity of N-Linked Glycosylation Pathways in Mammalian Cells," *PLoS ONE* 4:e7317, 2009.
Körner et al., "Carbohydrate Deficient Glycoprotein Syndrome Type IV: Deficiency of Dolichyl-P-Man: $Man_5GlcNAc_2$-PP-dolichyl Mannosyltransferase," *EMBO J.* 18:6816-6822, 1999.
Kornfeld and Kornfeld, "Assembly of Asparagine-Linked Oligosaccharides," *Annu. Rev. Biochem.* 54:631-664, 1985.
Kotz et al., "Approaching the Secrets of N-Glycosylation in *Aspergillus fumigatus*: Characterization of the AfOch1 Protein," *PLoS ONE* 5:e15729, 2010.
Kranz et al., "CDG-Id in Two Siblings With Partially Different Phenotypes," *Am. J. Med. Genet.* 143A:1414-1420, 2007.
Kukuruzinska et al., "Protein Glycosylation in Yeast," *Annu. Rev. Biochem.* 56:915-944, 1987.
Maddi and Free, "α-1,6-Mannosylation of N-Linked Oligosaccharide Present on Cell Wall Proteins is Required for Their Incorporation into the Cell Wall in the Filamentous Fungus *Neurospora crassa,*" *Eukaryot. Cell* 9:1766-1775, 2010.
Magnuson and Lasure, "Organic Acid Production by Filamentous Fungi," in *Advances in Fungal Biotechnology for Industry, Agriculture, and Medicine*, Lange and Lange (eds.), pp. 307-340, Kluwer Academic/Plenum Publishers, 2004.
Manthri et al., "Deletion of the *TbALG3* Gene Demonstrates Site-Specific N-Glycosylation and N-Glycan Processing in *Trypanosoma brucei,*" *Glycobiology* 18:367-383, 2008.

Maras et al., "Molecular Cloning and Enzymatic Characterization of a *Trichoderma reesei* 1,2-α-D-mannosidase," *J. Biotechnol.* 77:255-263, 2000.
Nam et al., "The Effects of Culture Conditions on the Glycosylation of Secreted Human Placental Alkaline Phosphatase Produced in Chinese Hamster Ovary Cells," *Biotech. Bioeng.* 100:1178-1192, 2008.
Nevalainen et al., "Heterologous Protein Expression in Filamentous Fungi," *Trends Biotechnol.* 23:468-474, 2005.
Oda et al., "*Aspergillus oryzae laeA* Regulates Kojic Acid Synthesis Genes," *Biosci. Biotechnol. Biochem.* 75:1832-1834, 2011.
Pang et al., "Human Sperm Binding is Mediated by the Sialyl-Lewis$^x$ Oligosaccharide on the Zona Pellucida," *Science* 333:1761-1764, 2011.
Punt et al., "Filamentous Fungi as Cell Factories for Heterologous Protein Production," *Trends Biotechnol.* 20:200-206, 2002.
Ramamoorthy et al., "*veA*-Dependent RNA-pol II Transcription Elongation Factor-Like Protein, RtfA, is Associated with Secondary Metabolism and Morphological Development in *Aspergillus nidulans,*" *Mol. Microbiol.* 85:795-814, 2012.
Reyes-Dominguez et al., "Heterochromatic Marks are Associated with the Repression of Secondary Metabolism Clusters in *Aspergillus nidulans,*" *Mol. Microbiol.* 76:1376-1386, 2010.
Roze et al., "Volatile Profiling Reveals Intracellular Metabolic Changes in *Aspergillus parasiticus*: *veA* Regulates Branched Chain Amino Acid and Ethanol Metabolism," *BMC Biochem.* 11:33, 2010.
Sakai et al., "Heterologous Expression System in *Aspergillus oryzae* for Fungal Biosynthetic Gene Clusters of Secondary Metabolites," *Appl. Microbiol. Biotechnol.* 93:2011-2022, 2012.
Sauer et al., "Microbial Production of Organic Acids: Expanding the Markets," *Trends Biotechnol.* 26:100-108, 2008.
Schollen et al., "CDG-Id Caused by Homozygosity for an ALG3 Mutation Due to Segmental Maternal Isodisomy UPD3(q21.3-qter)," *Eur. J. Med. Genet.* 48:153-158, 2005.
Schuster et al., "On the Safety of *Aspergillus niger*—A Review," *Appl. Microbiol. Biotechnol.* 59:426-435, 2002.
Silberstein and Gilmore, "Biochemistry, Molecular Biology, and Genetics of the Oligosaccharyltransferase," *FASEB J.* .10:849-858, 1996.
Soukup et al., "Overexpression of the *Aspergillus nidulans* Histone 4 Acetyltransferase EsaA Increases Activation of Secondary Metabolite Production," *Mol. Microbiol.* 86:314-330, 2012.
Stibler et al., "Carbohydrate-Deficient Glycoprotein Syndrome—A Fourth Subtype," *Neuropediatrics* 26: 235-237, 1995.
Sun et al., "Congenital Disorder of Glycosylation Id Presenting with Hyperinsulinemic Hypoglycemia and Islet Cell Hyperplasia," *J. Clin. Endocrinol. Metab.* 90:4371-4375, 2005.
Trombetta and Parodi, "Quality Control and Protein Folding in the Secretory Pathway," *Ann. Rev. Cell Dev. Biol.* 19:649-676, 2003.
Tsang et al., "Analytical and Computational Approaches to Define the *Aspergillus niger* Secretome," *Fungal Genet. Biol.* 46:S153-S160, 2009.
Xing et al., "Molecular Cloning and Characterization of the Global Regulator LaeA in *Penicillium citrinum,*" *Biotechnol. Lett.* 32:1733-1737, 2010.
Yan and Lennarz, "Unraveling the Mechanism of Protein N-glycosylation," *J. Biol. Chem.* 280:3121-3124, 2005.
Yu et al., "Conservation of Structure and Function of the Aflatoxin Regulatory Gene *aflR* from *Aspergillus nidulans* and *A. flavus,*" *Curr. Genet.* 29:549-555, 1996.

\* cited by examiner

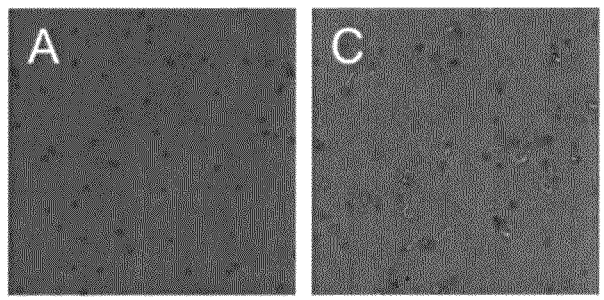
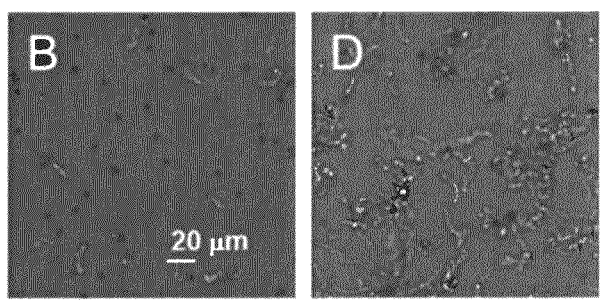
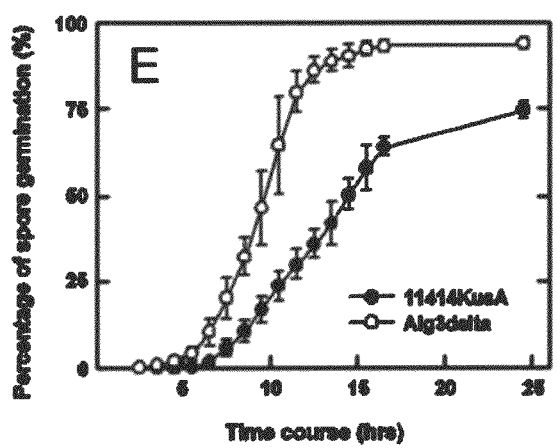
FIG. 6

FIG. 9

GENE ID: 5996303 AOR_1_556094 | dolichyl-P-Man:Man(5)GlcNAc(2)-PP-dolichyl mannosyltransferase [Aspergillus oryzae RIB40] (10 or fewer PubMed links)

Score = 137 bits (74), Expect = 2e-28
Identities = 400/553 (72%), Gaps = 40/553 (7%)
Strand=Plus/Plus

```
Query   801   CAGGTTTTACTCGCGATACCGTTCCTACAAAACAACCCGGCGGGGTATC-TCTCGCGGGC   859
              ||||||  ||||  |||||  ||  ||||||||     |||||   || || |  ||||||||
Sbjct   643   CAGGTTCTACTAGCGATTCCCTTCCTACAGGGTAACCCCATAGGATA-CGTCGCGCGGGC   701

Query   860   GTTCGAGCTAACCAGACAGTTCATGTTTAAATGGACAGTCAATTGGAGATTTGTTGGCGA   919
              ||  |||  |  ||  |||||||||| |||||  |||||||||||| ||||||||| |||||  || ||
Sbjct   702   CTTTGAGTTGACTAGACAGTTTATGTTCAAATGGACTGTCAATTGGAGGTTTGTGGGTGA   761

Query   920   AGAAGTATTCTTAT-CTAAGAGCTTTTCCCTGGCATTGCT-GGCCGTCCACATTGTGCTG   977
              |||   |  ||| ||| |  || ||  |||||| || || || ||    |  | ||| |  |||
Sbjct   762   AGACTTGTTCCTATCCAAACAG-TTTTCTCTAGCCTTACTAGG-TTTGCATATTTTCTG   819

Query   978   CTAGGCG-CT-TTTGCCGTCACTGGTTGGCTGA-GATAC-TCCAGG-TCTAGCTTGCCTG   1032
              || || |   | ||||    ||| || |||  |   |  | |||| |||| | | ||||
Sbjct   820   CT-GG-GATTATTTGTTACCACAGGCTGG-TTACG-GCCGT-CAGGATCTAACGTCCCTG   874

Query   1033  -CGTTCATTCGGAATCTGCTAGC-GGGTCGACATCGCACAGT-GTCCCTCCCCAAACCCT   1089
               | ||| |||||   |  ||     || ||  ||||| || |  | |   | ||
Sbjct   875   AC-TTCCTCCGGAGCCTACT-CCAAGGACGCCAACGCACCGTGGT-GCTTTCTAAGTCTT   931

Query   1090  ACATCATGAGCGTGATGCTCTCGTCTCTGACAG-TTGGCTTGTTGTGCGCAAGGTCCCTT   1148
              ||| |||| |||||||   |  | || |   |   | ||||||||||||||||||||||||
Sbjct   932   TCATAATGACCGTGATGTTGACATCGCTGGC-GATCGGGTTGTTGTGCGCAAGGTCCCTT   990

Query   1149  CATTACCAATTCTTCGCCTACCTCTCCTGGGCGACACCCTT-CCTCCTCTGGCGCGCAGG   1207
              |||||||||||||| |||| | |||||||||||   |  || ||  || ||||   || |
Sbjct   991   CATTACCAATTCTTTGCCTATCTCTCCTGGGCTACGCC-TTGCCTTCTCTGGCGGGCTCG   1049

Query   1208  GTTTCATCCAATC-TTGCTGTAC-CTTATCTGGGCTA-TGCAAGAGTGGGCTTGGAACA-   1263
              |  ||||||  ||| ||  | ||   |||||||||| || |||  ||||| |||||||||
Sbjct   1050  GCTCCATCCGATCCTTA-TATATGCG-ATCTGGGC-ACTACAGGAGTGGGCTTGGAATGT   1106

Query   1264  CATTCCCCAGCACCAAC-CTCAGTTCCATCATT-GTTGTCCTCTCACTTGCTACCCAGAG   1321
              |  |||  |||||||||    ||||||  || | ||||||  |||||||||||   |||  |
Sbjct   1107  C-TACCCAAGCACCAATGC-CAGTTCT-TCGGTCGTTGTCTTCTCACTTGCTGTTCAG-G   1162

Query   1322  TTT-CGGCGTCCT   1333
              ||| ||| |||||
Sbjct   1163  TTTTCGGTGTCCT   1175
```

FIG. 10A

```
                       +.  ...  ........  .. +  .   ..  ..  ....+..+..+...* +.*...+..**+*
Aspergillus niger    1) MD---------------WM-----RLIRDLCFNPRHTKWMAPLLVLGDAFLCALIIWKV
Aspergillus nid.     1) MA---------------L----TDLVSGLCSNPKHTKWIAPILNIADGLLCAFIIWKV
Fusarium oxy.        1) -------MPESASGTLSQGVRFLRNVLNGRHAL----SKLIPIALWLVDALGCGLIIWKI
Neurospora cra.      1) MAAPSS-RPESNPPLYKQALDFALDVANGRHAL----SKLIPPALFLVDALLCGLIIWKV
Saccharomyces cer.   1) MAGGKK-KSSTAPSRFQKTL-SSIWQDKHTVLFKPEYTLLVTAVLWFLEIAINIWVIQKV
Arabidopsis tha.     1) MA-GAS-SPASLRASRSRRL--GKETNRSDLFKKP--AVPFAFALILADAILVALIIAYV
Homo sap.            1) RKRGRSgSAAQAEGLCKQWL-QRAWQERRLLLREPRYTLLVAACLCLAEVGITFWVIHRV +****.+.**+.+++*+++*+.++*+*********+++*.*+.+*++*+.*.+*..+
Aspergillus niger   40) PYTEIDWATYMQQISLYLSGERDYTLIRGSTGPLVYPAAHVYSYTALYHLTDEGRDIFFG
Aserpgillus nid.    40) PYTEIDWTTYMQQVKLYLSGERDYTLIKGSTGPLVYPAAHVYSYSLFHHLTDEGRDIVFG
Fusarium oxy.       50) PYTEIDWVAYMQQISQFVSGERDYTKMEGDTGPLVYPAAHVYTYTGLYYITDKGTNILLA
Neurospora cra.     56) PYTEIDWAAYMEQVSQILSGERDYTKVRGGTGPLVYPAAHVYIYTGLYHLTDEGRNILLA
Saccharomyces cer.  59) SYTEIDWKAYMDEVEGVINGTYDYTQLKGDTGPLVYPAGFVYIFTGLYYLTDHGHNIRLG
Arabidopsis tha.    55) PYTKIDWDAYMSQVSGFLGGERDYGNLKGDTGPLVYPAGFLYVYSAVQNLT--GGEVYPA
Homo sap.           60) AYTEIDWKAYMAEVEGVINGTYDYTQLQGDTGPLVYPAGFVYIFMGLYYATSRGTDIRMA

*.+*+.+*+++*.+*+ +*.+...+***...+.++++*+*+**+*+*+***.+*...+*.
Aspergillus niger  100) QILFAVLYLITLVVVLCCYRQSG-APPY-LLPLLVLSKRLHSVYVLRLFNDGLAALAMWV
Aspergillus nid.   100) QIIFAFLYLICLTVVMACYRRVG-APPY-LFPLLVLSKRLHSVYMLRLFNDGLAALAMWG
Fusarium oxy.      110) QQIFAVLYMATLAVVMLCYWKAK-VPPY-MFIFLIASKRLHSLFVLRCFNDCFAVFFLWL
Neurospora cra.    116) QQLFAGLYMVTLAVVMGCYWQAK-APPY-LFPLLTLSKRLHSIFVLRCFNDCFAVLFLWL
Saccharomyces cer. 119) QYVFAVSYLINLLLVMRIYHRTKKVPPYVFFFICCASYRIHSIFILRLFNDPVAMMLCFG
Arabidopsis tha.   113) QILFGVLYIVNLGIVLIIYVKTD-VPWW-ALSLLCLSKRIHSIFVLRLFNDCFAMTLLHA
Homo sap.          120) QNIFAVLYLATLLLVFLIYHQTCKVPPFVFFFMCCASYRVHSIFVLRLFNDPVAMVLLFL ++ +*..++*. +..+*+.+++*+++..*++.+++....+ + ..+........ +*+
Aspergillus nig.   158) AILLFMNRKWTAAVAVWSTGVAIKMTLLLLAPAIAVVTVLSLS-LGPSVGLGVLAVLVQV
Aspergillus nid.   158) SIWLFINRKWTPAVVLWSLGLGVKMTLILLVPAVMVVLALSLD-IGRCIRLAGLALGIQI
Fusarium oxy.      168) TIFLFQRRQWTVGSLVYSWGLGIKMSLLLVLPAIGVILFLGRG-LWPSLRLAWLMAQIQF
Neurospora cra.    174) AIFFFQRRNWQAGALLYTLGLGVKMTLLLSLPAVGIVLFLGSGsFVTTLQLVATMGLVQI
Saccharomyces cer. 179) AINLFLDGRWTLGCALYSLAVSVKMNVLLFAPGLLFLLLCEFG-LWKTLPRLALCAVIQL
Arabidopsis tha.   171) SMALFLYRKWHLGMLVFSGAVSVKMNVLLYAPTLLLLLLKAMN-IIGVVSALAGAALVQI
Homo sap.          180) SINLLLAQRWGWGCCFFSLAVSVKMNVLLFAPGLLFLLLTQFG-FRGALPKLGICAGLQV ++++***..+*.+*.+*+**++*+*.*+*********++*.+*++*.*.+.**..*+.+*..
Aspergillus niger  217) LLAIPFLQNNPAGYLSRAFELTRQFMFKWTVNWRFVGEEVFLSKSFSLALLAVHIVLLGA
Aspergillus nid.   217) LLAIPFLKTNPSGYFERAFEFGRQFMFKWTVNWRFVGEDIFLSKGFWAGLIVLHLLILVV
Fusarium oxy.      227) AIGLPFITKNPRGYAARAFELSRQFQFKWTVNWRMLGEEVFLSKYFALSLLACHILVLLI
Neurospora cra.    234) LIGVPFLAHYPTEYLSRAFELSRQFFFKWTVNWRFVGEEIFLSKGFALTLLALHVLVLGI
Saccharomyces cer. 238) VLGLPFLLVNPVGYVSRAFDLGRQFLFKWTVNWRFLPEDVFLNRYFHLALLLAHITTLLL
Arabidopsis tha.   230) LVGLPFLITYPVSYIANAFDLGRVFIHFWSVNPKFVPERVFVSKEFAVCLLIAHLFLLVA
Homo sap.          239) VLGLPFLLENPSGYLSRSFDLGRQFLFHWTVNWRFLPEALFLHRAFHLALLTAHLTLLLL

*....*....+.++ .++.. .         ........ .. .... +.+.++++.+++++.
Aspergillus niger  277) FAVTGWLRYSRSSLPAFIRNLL------AGRHR---------TVSLPKPYIMSVMLSSLT
Aspergillus nid.   277) LGFTCFLNPSGTSLPDFAGRFL------TGQHR---------GIALHPSFIMSALLTSLS
Fusarium oxy.      287) FISKRWIQPTGRSLYDLIPSFLrlkSPFTMQEQ------LRISHYVTPEYAMTTMLTANL
Neurospora cra.    294) FITTRWIKPARKSLVQLISPVL-----LAGKPPLTVPEhRAAARDVTPRYIMTTILSANA
Saccharomyces cer. 298) FALKRW-KRSGSSIWTILKDPS---------ER------KETAHKVNADQMVLILFTSNF
Arabidopsis tha.   290) FANYKWCKHEG-GIIGFMRSRH---FFLTLPSSLSFSD-VSASRIITKEHVVTAMFVGNF
Homo sap.          299) FALCRW-HRTGESILSLLRDPS--------KRKV--PP-----QPLTPNQIVSTLFTSNF
```

FIG. 10B

```
                     **++++***********+*+.*+*******+....++...*..+++...*++**+****..**.
Aspergillus niger 322) VGLLCARSLHYQFFAYLSWATPFLLWRAGFHPI---LLYLIWAMQEWAWNTFPSTNLSSI
Aspergillus nid.  322) VGLLCARSLHYQFFAYLSWATPFLLWQAGYHPI---LVYALWLVQEWAWNVYPSTNLSSA
Fusarium oxy.     341) IGLLFARSLHYQFYAYLAWATPYLLWRATEDPV---IVAIIWAAQEWAWNVYPSTDLSST
Neurospora cra.   349) VGLLFARSLHYQFYAYVAWSTPFLLWRAGLHPV---LVYLLWAVHEWAWNVFPSTPASSA
Saccharomyces cer. 342) IGMCFSRSLHYQFYVWYFHTLPYLLWSGGVKKLARLLRVLILGLIELSWNTYPSTNYSSL
Arabidopsis tha.  345) IGIVFARSLHYQFYSWYFYSLPYLLWRTPF-PT--WLRLIMFLGIELCWNVYPSTPSSSG
Homo sap.         343) IGICFSRSLHYQFYVWYFHTLPYLLWAMPARWLTHLLRLLVLGLIELSWNTYPSTSCSSA .+.  .........++.+....  ........+.+.+ ..-
Aspergillus niger 379) IVVLSLATQSFGVLANSASA-FYTMRSNPSGKEHNQ--
Aspergillus nid.  379) AVVLLLGAQVLGVLVNRDRA-FPSSPPTPKAKQHVQ--
Fusarium oxy.     398) IAVNTMLATVVLVYLGTARR-AVPAPAAQVGNVDDKNk
Neurospora cra.   406) VVVGVLGVTVAGVWFGAREEwEPGMKSSSKKEEAAMR-
Saccharomyces cer. 402) SLHVCHLIILLCLWLNPNPA-SPSHRSENKAKSH----
Arabidopsis tha.  402) LLLCLHLIILVGLWLAPSVD-PYQLKEHPKSQIHKKA-
Homo sap.         403) ALHICHAVILLQLWLGPQPF--PKSTQHSK-KAH----
```

FIG. 11

```
Score =  279 bits (713),   Expect = 2e-87, Method: Compositional matrix
adjust.
 Identities = 159/405 (39%), Positives = 239/405 (59%), Gaps = 6/405 (1%)

Query   12   FNPRHTKWMAPLLVLGDAFLCALIIWKVPYTEIDWATYMQQISLYLSGERDYTLIRGSTG    71
             F P +T   +L  +  +   +I KV YTEIDW  YM ++     ++G  DYT ++G TG
Sbjct   31   FKPEYTLLVTAVLWFLEIAINIWVIQKVSYTEIDWKAYMDEVEGVINGTYDYTQLKGDTG    90

Query   72   PLVYPAAHVYSYTALYHLTDEGRDIFFGQILFAVLYLITLVVVLCCY-RQSGAPPYLLPL   130
             PLVYPA  VY +T LY+LTD G +I   GQ +FAV YLI L++V+  Y R     PPY+
Sbjct   91   PLVYPAGFVYIFTGLYYLTDHGHNIRLGQYVFAVSYLINLLLVMRIYHRTKKVPPYVFFF   150

Query  131   LVL-SKRLHSVYVLRLFNDGLAALAMWVAILLFMNRKWTAAVAVWSTGVAIKMTLLLLAP   189
             +   S R+HS+++LRLFND +A +  + AI LF++ +WT   A++S V++KM +LL AP
Sbjct  151   ICCASYRIHSIFILRLFNDPVAMMLCFGAINLFLDGRWTLGCALYSLAVSVKMNVLLFAP   210

Query  190   AIAVVTVLSLSLGPSVGLGVLAVLVQVLLAIPFLQNNPAGYLSRAFELTRQFMFKWTVNW   249
             + + +    L  ++   L  ++Q++L +PFL  NP GY+SRAF+L RQF+FKWTVNW
Sbjct  211   GLLFLLLCEFGLWKTLPRLALCAVIQLVLGLPFLLVNPVGYVSRAFDLGRQFLFKWTVNW   270

Query  250   RFVGEEVFLSKSFSLALLAVHIVLLGAFAVTGWLRYSRSSLPAFIRNLLAGRHRTVSLPK   309
             RF+  E+VFL++  F LALL  HI  L  FA+   W R S SS+   +++     +  +
Sbjct  271   RFLPEDVFLNRYFHLALLLAHITTLLLFALKRWKR-SGSSIWTILKDPSERKETAHKVNA   329

Query  310   PYIMSVMLSSLTVGLLCARSLHYQFFAYLSWATPFLLWRAGFHP---ILLYLIWAMQEWA   366
              ++ ++ +S  +G+  +RSLHYQF+ +    P+LLW  G    +L  LI  + E +
Sbjct  330   DQMVLILFTSNFIGMCFSRSLHYQFYVWYFHTLPYLLWSGGVKKLARLLRVLILGLIELS   389

Query  367   WNTFPSTNLSSIIVVLSLATQSFGVLANSASAFYTMRSNPSGKEH   411
             WNT+PSTN SS+ + +          + N  A   RS    K H
Sbjct  390   WNTYPSTNYSSLSLHVCHLIILLCLWLNPNPASPSHRSENKAKSH   434
```

FIG. 12

*A. nidulans*

```
Query    1   MTSPAHNHYSYHSPTSSDRGRSRQNSDAMDIQSITEREPATR-------YAVAGGPAPWN   53
             M SP N+YSY   S D GRSRQNSDAMDI  IT +EP        Y    GGPA  +
Sbjct   14   MASPNRNNYSYQGIESYDSGRSRQNSDAMDIHVITAQEPPREPPDNNDPYDGHGGPAGTS   73
```

*A. niger*

```
Query   54   RNGSPSMSPINSERNQFHEENGRTYHGFRRGMYFLPCDEQEQDRLDIFHKLFTVARVSES  113
                    P       R  F+EENGRTYHG+RRG+Y LPCDEQEQDRLDIFHKLFTVAR+SES
Sbjct   74   HYSKPP------NRWLFYEENGRTYHGYRRGVYPLPCDEQEQDRLDIFHKLFTVARMSES  127

Query  114   LIYAPHPTNGRFLDLGCGTGIWAIEVANKYPDAFVAGVDLAPIQPPNHPKNCEFYAPFDF  173
             LIYAPHP NGRFLDLGCGTGIWAI+VA+KYP+AFVAGVDLAPIQPPNHP NCEFYAPFDF
Sbjct  128   LIYAPHPPNGRFLDLGCGTGIWAIDVAHKYPNAFVAGVDLAPIQPPNHPDNCEFYAPFDF  187

Query  174   EAPWAMGEDSWDLIHLQMGCGSVMGWPNLYRRIFAHLRPGAWFEQVEIDFEPRCDDRSLD  233
             EAPW +GE+SWDLIHLQMGCGSV+GW NLY+RI   HL+PGAWFEQVEIDFEPRCDDRSL+
Sbjct  188   EAPWTLGENSWDLIHLQMGCGSVLGWQNLYKRILRHLQPGAWFEQVEIDFEPRCDDRSLN  247

Query  234   GTALRHWYDCLKQATAETMRPIAHSSRDTIKDLQDAGFTEIDHQIVGLPLNPWHQDEHER  293
             G ALR WY  LKQAT +TMRPIAHSSRDTI+ L++AGFT+IDHQ+VGLPLNPWH+DEHE+
Sbjct  248   GLALREWYQYLKQATQDTMRPIAHSSRDTIRHLEEAGFTQIDHQMVGLPLNPWHRDEHEQ  307

Query  294   KVARWYNLAVSESIENLSLAPFSRVYRWPLERIQQLAADVKSEAFNKEIHAYNILHIYQA  353
             KVARWYNLA+SESIE LSLAPFSR++ W L+RI+Q+ A+VKS+AFNKEIHAYNILHIYQA
Sbjct  308   KVARWYNLAISESIETLSLAPFSRIFHWDLDRIRQITAEVKSQAFNKEIHAYNILHIYQA  367

Query  354   RKP  356
             RKP
Sbjct  368   RKP  370
```

FIG. 15A. Oligo primers:PTR5F/PTR3R
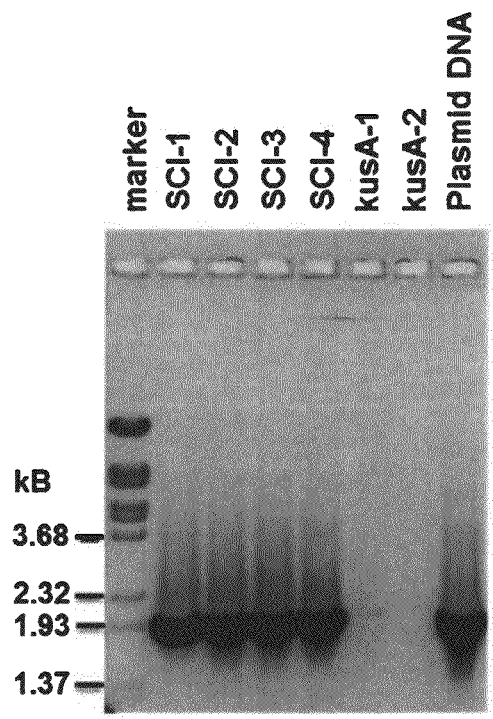
FIG. 15B. Oligo primers:LaeA5F/TRP3R
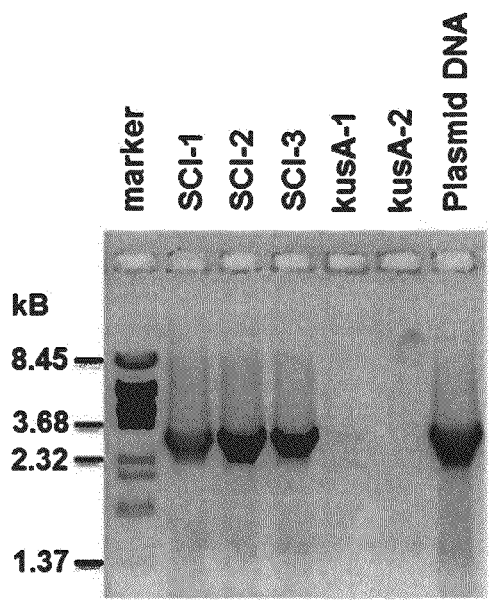

SEQUENCE LISTING

<160> NUMBER OF SEQ ID NOS: 60

<210> SEQ ID NO 1
<211> LENGTH: 3888
<212> TYPE: DNA
<213> ORGANISM: Aspergillus niger
<220> FEATURE:
<221> NAME/KEY: CDS
<222> LOCATION: (1186)..(1306)
<220> FEATURE:
<221> NAME/KEY: Intron
<222> LOCATION: (1307)..(1392)
<220> FEATURE:
<221> NAME/KEY: CDS
<222> LOCATION: (1393)..(1916)
<220> FEATURE:
<221> NAME/KEY: Intron
<222> LOCATION: (1917)..(1988)
<220> FEATURE:
<221> NAME/KEY: CDS
<222> LOCATION: (1989)..(2582)

<400> SEQUENCE: 1

```
tctgacattg aactacagtc ataacttctc tccctcccc ggcttcccg gtcgtccttc      60 tatcgccgcc ccccccgcta tccattggtg aggccatgct atgattgggg cgtcctacct    120
tgcctgtcat taagttttg tgctttggtt gctacaaggt tggactattc ctttcttttg     180
cattgttctt ttacaccgaa actaacgcat gcccgcggcc tagtgaacgc atcgtcgtta    240
ccgtcaccct ccgctccgca taaatcttct ccttaattgc tcacatccac atttcaacat    300
gccgccgcat ctacatcccc ggtcacggtc aacgtcctcc ctcttcgccg ggacgctcct    360
ggcttccttg gtcgtcgtcg gcctaccaca tgtcttcc tgtcccgccc cgcgtcgcac      420
attcgccgat tctgagatga taatgtcggc agatgggcaa cctatccaga gaatccgcag    480
acgacgtcgg aaagacgaag aactccttgg ccaggatggc aatccgctcg gccagacgca    540
gcctgcagcc gatgaagagg tgtctacgtt cctacaattg gaagaagaag cacagagatt    600
ggccaaggca ggccacgagt gtcctgttcc caagcctcga gggattctgg gcgaattgct    660
gggttttacg agtagtggag gtatttcgac atcaacgacg acacaggcac aacaggttgg    720
agagggtcgg taaccgacaa ttggaaagca aggaggactc aatcaaggct aaaataggct    780
ttgagcatgt acagcgtgaa ggaactgtgg attatatcac gaaataagcc atgaggcagt    840
cgtgttggct tcgacggagg ttggcttcgg aaattttcgg ccgggcacca aatccgaccc    900
atggcagcaa tatacccatc tttgtatcga tagtgtactt acaaaaactg tctactatat    960
gattatgcat atgcgattaa atacaactct caattgatgc acaattcgcc tcaacttcta   1020
tggtaacgaa cccacctgtt ctgcagacat gcggccgcgc ggtctgtgtg tgtccatgaa   1080
cgctaatccc aaacgggaca gctctcattg gctctccggc acgaagaggc caccgacat    1140 ctacagctgt agaagaaagt agctggttca acaaccgcat gcaag atg gac tgg atg  1197
                                                  Met Asp Trp Met
                                                   1 cgc cta att cgc gat ttg tgt ttc aat ccc cga cac aca aaa tgg atg     1245
Arg Leu Ile Arg Asp Leu Cys Phe Asn Pro Arg His Thr Lys Trp Met
 5                 10                  15                  20 gct ccg ctc ctg gtc ctg ggt gac gct ttc ctc tgc gcg ctg atc atc     1293
Ala Pro Leu Leu Val Leu Gly Asp Ala Phe Leu Cys Ala Leu Ile Ile
             25                  30                  35 tgg aaa gtg ccc t gtaaggctac agctaagctc cgttcacacc cttttgcgac       1346
Trp Lys Val Pro
         40
```

-continued

| | |
|---|---|
| aagtgaagca atgccactaa cctagccccg ttgctattgt ccacag at acc gag<br>                                                                                             Tyr Thr Glu | 1400 |
| att gac tgg gcc acg tac atg caa caa ata tcg ctt tat ttg tca gga<br>Ile Asp Trp Ala Thr Tyr Met Gln Gln Ile Ser Leu Tyr Leu Ser Gly<br> 45                                 50                              55 | 1448 |
| gaa cgc gat tat act ctc atc aga gga tca acc ggt ccc ctt gtc tac<br>Glu Arg Asp Tyr Thr Leu Ile Arg Gly Ser Thr Gly Pro Leu Val Tyr<br>60                      65                              70                        75 | 1496 |
| ccg gcc gcc cat gta tac agt tat acg gcc ctc tac cat ctc acc gat<br>Pro Ala Ala His Val Tyr Ser Tyr Thr Ala Leu Tyr His Leu Thr Asp<br>                 80                         85                              90 | 1544 |
| gag ggg cgc gat att ttc ttc ggt cag ata cta ttt gct gtg ctc tac<br>Glu Gly Arg Asp Ile Phe Phe Gly Gln Ile Leu Phe Ala Val Leu Tyr<br>              95                             100                        105 | 1592 |
| ttg atc acg ctg gtg gtt gtg ctg tgc tgt tat aga cag tcg ggt gct<br>Leu Ile Thr Leu Val Val Val Leu Cys Cys Tyr Arg Gln Ser Gly Ala<br>110                     115                              120 | 1640 |
| ccg ccg tac ttg ctt ccg ctg ctg gtc ctt tcc aag aga ctt cac agc<br>Pro Pro Tyr Leu Leu Pro Leu Leu Val Leu Ser Lys Arg Leu His Ser<br>    125                             130                          135 | 1688 |
| gtt tat gtc ctg cgt ctg ttc aat gat ggc ttg gcg gcg ctg gcg atg<br>Val Tyr Val Leu Arg Leu Phe Asn Asp Gly Leu Ala Ala Leu Ala Met<br>140                     145                              150                        155 | 1736 |
| tgg gtt gcc att ctg tta ttc atg aat cgg aag tgg acg gct gcg gtc<br>Trp Val Ala Ile Leu Leu Phe Met Asn Arg Lys Trp Thr Ala Ala Val<br>               160                            165                        170 | 1784 |
| gca gtg tgg tct act ggt gtt gcg att aag atg aca ctg ttg ctg ctg<br>Ala Val Trp Ser Thr Gly Val Ala Ile Lys Met Thr Leu Leu Leu Leu<br>            175                            180                          185 | 1832 |
| gcc ccg gct att gct gtg gtc acg gtg ctt agt ctg tcg ctt ggt cct<br>Ala Pro Ala Ile Ala Val Val Thr Val Leu Ser Leu Ser Leu Gly Pro<br>190                     195                              200 | 1880 |
| agc gtg ggg ctg ggg gtt ctg gcg gtg ctt gtc cag gtaggttccc<br>Ser Val Gly Leu Gly Val Leu Ala Val Leu Val Gln<br>    205                             210                          215 | 1926 |
| atgaggctgt agggttggcc aaaggcaatt tgtgtgaaga cttgtctgac attgaactac | 1986 |
| ag gtt tta ctc gcg ata ccg ttc cta caa aac aac ccg gcg ggg tat<br>   Val Leu Leu Ala Ile Pro Phe Leu Gln Asn Asn Pro Ala Gly Tyr<br>                     220                              225                        230 | 2033 |
| ctc tcg cgg gcg ttc gag cta acc aga cag ttc atg ttt aaa tgg aca<br>Leu Ser Arg Ala Phe Glu Leu Thr Arg Gln Phe Met Phe Lys Trp Thr<br>                  235                           240                        245 | 2081 |
| gtc aat tgg aga ttt gtt ggc gaa gaa gta ttc tta tct aag agc ttt<br>Val Asn Trp Arg Phe Val Gly Glu Glu Val Phe Leu Ser Lys Ser Phe<br>        250                              255                          260 | 2129 |
| tcc ctg gca ttg ctg gcc gtc cac att gtg ctg cta ggc gct ttt gcc<br>Ser Leu Ala Leu Leu Ala Val His Ile Val Leu Leu Gly Ala Phe Ala<br>             265                            270                          275 | 2177 |
| gtc act ggt tgg ctg aga tac tcc agg tct agc ttg cct gcg ttc att<br>Val Thr Gly Trp Leu Arg Tyr Ser Arg Ser Ser Leu Pro Ala Phe Ile<br>          280                            285                          290 | 2225 |
| cgg aat ctg cta gcg ggt cga cat cgc aca gtg tcc ctc ccc aaa ccc<br>Arg Asn Leu Leu Ala Gly Arg His Arg Thr Val Ser Leu Pro Lys Pro<br>295                     300                              305                        310 | 2273 |
| tac atc atg agc gtg atg ctc tcg tct ctg aca gtt ggc ttg ttg tgc<br>Tyr Ile Met Ser Val Met Leu Ser Ser Leu Thr Val Gly Leu Leu Cys<br>                 315                           320                        325 | 2321 |
| gca agg tcc ctt cat tac caa ttc ttc gcc tac ctc tcc tgg gcg aca<br>Ala Arg Ser Leu His Tyr Gln Phe Phe Ala Tyr Leu Ser Trp Ala Thr | 2369 |

```
                  330               335               340
ccc ttc ctc ctc tgg cgc gca ggg ttt cat cca atc ttg ctg tac ctt     2417
Pro Phe Leu Leu Trp Arg Ala Gly Phe His Pro Ile Leu Leu Tyr Leu
        345                 350                 355 atc tgg gct atg caa gag tgg gct tgg aac aca ttc ccc agc acc aac     2465
Ile Trp Ala Met Gln Glu Trp Ala Trp Asn Thr Phe Pro Ser Thr Asn
360                 365                 370 ctc agt tcc atc att gtt gtc ctc tca ctt gct acc cag agt ttc ggc     2513
Leu Ser Ser Ile Ile Val Val Leu Ser Leu Ala Thr Gln Ser Phe Gly
375                 380                 385                 390 gtc ctt gcg aat agt gcc agc gcc ttt tat acc atg cgt tcg aac cct     2561
Val Leu Ala Asn Ser Ala Ser Ala Phe Tyr Thr Met Arg Ser Asn Pro
                395                 400                 405 agc ggt aaa gag cat aac caa tagaagtgac acccggccag tatcgagatc        2612
Ser Gly Lys Glu His Asn Gln
            410 gggctgtgac aggtgcatcg ataatcgcaa tcagtcttgt acccatgaga atccctgaaa   2672 aagtaagact gctctgtcag gtagtccatt gcccatgcga taggttcgga cgcctaaagg   2732 atcaatcaag atgccaatca agcatccgac tcatcggaag aaggcatctt gccgacattg   2792 gactcatcct cttcgtccga gtcgtcggcg acaacagcag cttgcttagc gaactccttt   2852 ggcctgcaga gggatcagta gtagcccag gcaccgcgat tgagggatcc actcaccaaa    2912 acggggcttt cgccacgct ttctcatcac gaacgatgtt gactatttct cccttgagct    2972 tgttgtcgcg gccctcaaga gcattggtat cgatgaccac gtaggaaccc gcttgatcc    3032 agatggtcga tcggaagcgg gcagggagct ccaccaaaac cgactccttc gagggaagtt   3092 ccaccgagta gatgttgttt ccggtcgcct tgatagcccg ggcaattaga tggccctgag   3152 acagctcatc cggcgggaac atggtctctt ccgccgtagc gagaaccttg cgcctagggg   3212 gacccatttc taacgtatac gcaagtggtt cagcgggaag tagtgtcgat ctaaattggg   3272 atgaacacca aagagactga agaaagagtg agcaaaatgc gagaaaccgt cgactgcgga   3332 gagttttact cgaatgaaga aattcgggcg gcagaaaatc cccggtgggg agtgtgggtc   3392 ccccatccgc ttcttttgcca atctcgctct ctctcttctc tcatctccgc catctacgga   3452 gtagagctcc agtactacta tctacttacg gccgtgctca tatccattgg ttgtgaggaa   3512 tgtggcatct tagttggcta cacagtgcac tacacaatcc atcgaatcaa ggtcttcctg   3572 gcgagtcagt tcccctgcac aatgtttggc ctaaggcgga catctagacc acttgacctc   3632 gtgtttttgg gccttctgc cggcatttgg agtggatgta tcatatcgtg aaacttgcat    3692 gtgtctgatt ggcttccggc ttttatctct ttgaacttcg ctcactggtg gggttcgcgg   3752 agtgatattc cgctcaagct aattcacctc catggatatt aataatgacc ccgacacgtt   3812 ggggatcccc aaacctccgt aaaagaatcg tttatcctgg ggtctcggac agatttcgta   3872 ctacaaacct ctcacg                                                   3888

<210> SEQ ID NO 2
<211> LENGTH: 413
<212> TYPE: PRT
<213> ORGANISM: Aspergillus niger

<400> SEQUENCE: 2

Met Asp Trp Met Arg Leu Ile Arg Asp Leu Cys Phe Asn Pro Arg His
1               5                   10                  15

Thr Lys Trp Met Ala Pro Leu Leu Val Leu Gly Asp Ala Phe Leu Cys
            20                  25                  30
```

```
Ala Leu Ile Ile Trp Lys Val Pro Tyr Thr Glu Ile Asp Trp Ala Thr
            35                  40                  45

Tyr Met Gln Gln Ile Ser Leu Tyr Leu Ser Gly Glu Arg Asp Tyr Thr
        50                  55                  60

Leu Ile Arg Gly Ser Thr Gly Pro Leu Val Tyr Pro Ala Ala His Val
65                  70                  75                  80

Tyr Ser Tyr Thr Ala Leu Tyr His Leu Thr Asp Glu Gly Arg Asp Ile
                85                  90                  95

Phe Phe Gly Gln Ile Leu Phe Ala Val Leu Tyr Leu Ile Thr Leu Val
            100                 105                 110

Val Val Leu Cys Cys Tyr Arg Gln Ser Gly Ala Pro Pro Tyr Leu Leu
        115                 120                 125

Pro Leu Leu Val Leu Ser Lys Arg Leu His Ser Val Tyr Val Leu Arg
        130                 135                 140

Leu Phe Asn Asp Gly Leu Ala Ala Leu Ala Met Trp Val Ala Ile Leu
145                 150                 155                 160

Leu Phe Met Asn Arg Lys Trp Thr Ala Ala Val Ala Val Trp Ser Thr
                165                 170                 175

Gly Val Ala Ile Lys Met Thr Leu Leu Leu Ala Pro Ala Ile Ala
            180                 185                 190

Val Val Thr Val Leu Ser Leu Ser Leu Gly Pro Ser Val Gly Leu Gly
        195                 200                 205

Val Leu Ala Val Leu Val Gln Val Leu Leu Ala Ile Pro Phe Leu Gln
        210                 215                 220

Asn Asn Pro Ala Gly Tyr Leu Ser Arg Ala Phe Glu Leu Thr Arg Gln
225                 230                 235                 240

Phe Met Phe Lys Trp Thr Val Asn Trp Arg Phe Val Gly Glu Glu Val
                245                 250                 255

Phe Leu Ser Lys Ser Phe Ser Leu Ala Leu Leu Ala Val His Ile Val
            260                 265                 270

Leu Leu Gly Ala Phe Ala Val Thr Gly Trp Leu Arg Tyr Ser Arg Ser
        275                 280                 285

Ser Leu Pro Ala Phe Ile Arg Asn Leu Leu Ala Gly Arg His Arg Thr
        290                 295                 300

Val Ser Leu Pro Lys Pro Tyr Ile Met Ser Val Met Leu Ser Ser Leu
305                 310                 315                 320

Thr Val Gly Leu Leu Cys Ala Arg Ser Leu His Tyr Gln Phe Phe Ala
                325                 330                 335

Tyr Leu Ser Trp Ala Thr Pro Phe Leu Leu Trp Arg Ala Gly Phe His
            340                 345                 350

Pro Ile Leu Leu Tyr Leu Ile Trp Ala Met Gln Glu Trp Ala Trp Asn
        355                 360                 365

Thr Phe Pro Ser Thr Asn Leu Ser Ser Ile Ile Val Val Leu Ser Leu
        370                 375                 380

Ala Thr Gln Ser Phe Gly Val Leu Ala Asn Ser Ala Ser Ala Phe Tyr
385                 390                 395                 400

Thr Met Arg Ser Asn Pro Ser Gly Lys Glu His Asn Gln
                405                 410

<210> SEQ ID NO 3
<211> LENGTH: 1923
<212> TYPE: DNA
<213> ORGANISM: Aspergillus oryzae
<220> FEATURE:
```

<220> NAME/KEY: CDS
<222> LOCATION: (1)..(1242)

<400> SEQUENCE: 3

```
atg gag ttg aag cac ttc atc cac gaa ctc tgc cta aac ccc aga cat      48
Met Glu Leu Lys His Phe Ile His Glu Leu Cys Leu Asn Pro Arg His
1               5                   10                  15 aca aaa tgg att gca ccg ctt ctt gtc ata ggc gat gcc ttc cta tgt      96
Thr Lys Trp Ile Ala Pro Leu Leu Val Ile Gly Asp Ala Phe Leu Cys
            20                  25                  30 gct ctt atc atc tgg aag atc cca tat act gag atc gac tgg acg acg     144
Ala Leu Ile Ile Trp Lys Ile Pro Tyr Thr Glu Ile Asp Trp Thr Thr
        35                  40                  45 tac atg cag cag ata gcg ctt tac atc tct ggc gaa cgt gac tat acc     192
Tyr Met Gln Gln Ile Ala Leu Tyr Ile Ser Gly Glu Arg Asp Tyr Thr
    50                  55                  60 ctg atc aag ggg tcc act gga ccc ctt gta tac ccg gcc gcc cac gta     240
Leu Ile Lys Gly Ser Thr Gly Pro Leu Val Tyr Pro Ala Ala His Val
65                  70                  75                  80 tat agc tac atg gca ctc tat cac cta aca gat gaa ggc cga gat att     288
Tyr Ser Tyr Met Ala Leu Tyr His Leu Thr Asp Glu Gly Arg Asp Ile
                85                  90                  95 ctt ttc ggg cag ata tta ttt gct gtc ctt tac ctt gtc acg cta gca     336
Leu Phe Gly Gln Ile Leu Phe Ala Val Leu Tyr Leu Val Thr Leu Ala
            100                 105                 110 gtt gtg atg gtt tgc tac agg cag tca ggt gcc cct ccg tac ctg ttt     384
Val Val Met Val Cys Tyr Arg Gln Ser Gly Ala Pro Pro Tyr Leu Phe
        115                 120                 125 cct ctt ctt gtc ctt tcc aag cgg ctc cac agt gtc ttt gtt ttg cgc     432
Pro Leu Leu Val Leu Ser Lys Arg Leu His Ser Val Phe Val Leu Arg
    130                 135                 140 ctt ttc aat gat ggc ctc gcg gtc tgt gcc atg tgg ata gcg att ctg     480
Leu Phe Asn Asp Gly Leu Ala Val Cys Ala Met Trp Ile Ala Ile Leu
145                 150                 155                 160 ctc ttc cag aat aag aaa tgg acg gct ggt gtt acg gcc tgg act gtt     528
Leu Phe Gln Asn Lys Lys Trp Thr Ala Gly Val Thr Ala Trp Thr Val
                165                 170                 175 ggg gtt ggc att aag atg acg tta ctg ctc ctt gcg cca gcc att gcg     576
Gly Val Gly Ile Lys Met Thr Leu Leu Leu Leu Ala Pro Ala Ile Ala
            180                 185                 190 gtg gta act gtg ctc agc ctt tcc ctc gtg cct agt att cga ctt gga     624
Val Val Thr Val Leu Ser Leu Ser Leu Val Pro Ser Ile Arg Leu Gly
        195                 200                 205 att cta gca ttg ctc att cag gtt cta cta gcg att ccc ttc cta cag     672
Ile Leu Ala Leu Leu Ile Gln Val Leu Leu Ala Ile Pro Phe Leu Gln
    210                 215                 220 ggt aac ccc ata gga tac gtc gcg cgg gcc ttt gag ttg act aga cag     720
Gly Asn Pro Ile Gly Tyr Val Ala Arg Ala Phe Glu Leu Thr Arg Gln
225                 230                 235                 240 ttt atg ttc aaa tgg act gtc aat tgg agg ttt gtg ggt gaa gac ttg     768
Phe Met Phe Lys Trp Thr Val Asn Trp Arg Phe Val Gly Glu Asp Leu
                245                 250                 255 ttc cta tcc aaa cag ttt tct cta gcc tta cta ggt ttg cat att ttt     816
Phe Leu Ser Lys Gln Phe Ser Leu Ala Leu Leu Gly Leu His Ile Phe
            260                 265                 270 ctg ctg gga tta ttt gtt acc aca ggc tgg tta cgg ccg tca gga tct     864
Leu Leu Gly Leu Phe Val Thr Thr Gly Trp Leu Arg Pro Ser Gly Ser
        275                 280                 285 aac gtc cct gac ttc ctc cgg agc cta ctc caa gga cgc caa cgc acc     912
Asn Val Pro Asp Phe Leu Arg Ser Leu Leu Gln Gly Arg Gln Arg Thr
```

```
                 290                 295                 300
gtg gtg ctt tct aag tct ttc ata atg acc gtg atg ttg aca tcg ctg    960
Val Val Leu Ser Lys Ser Phe Ile Met Thr Val Met Leu Thr Ser Leu
305                 310                 315                 320 gcg atc ggg ttg ttg tgc gca agg tcc ctt cat tac caa ttc ttt gcc   1008
Ala Ile Gly Leu Leu Cys Ala Arg Ser Leu His Tyr Gln Phe Phe Ala
                325                 330                 335 tat ctc tcc tgg gct acg cct tgc ctt ctc tgg cgg gct cgg ctc cat   1056
Tyr Leu Ser Trp Ala Thr Pro Cys Leu Leu Trp Arg Ala Arg Leu His
            340                 345                 350 ccg atc ctt ata tat gcg atc tgg gca cta cag gag tgg gct tgg aat   1104
Pro Ile Leu Ile Tyr Ala Ile Trp Ala Leu Gln Glu Trp Ala Trp Asn
        355                 360                 365 gtc tac cca agc acc aat gcc agt tct tcg gtc gtt gtc ttc tca ctt   1152
Val Tyr Pro Ser Thr Asn Ala Ser Ser Ser Val Val Val Phe Ser Leu
    370                 375                 380 gct gtt cag gtt ttc ggt gtc ctc ctc aat agc aga aac gca ctg agc   1200
Ala Val Gln Val Phe Gly Val Leu Leu Asn Ser Arg Asn Ala Leu Ser
385                 390                 395                 400 gat gcg cct ccg aga cgc aaa gga aag gag cac atc cag tga            1242
Asp Ala Pro Pro Arg Arg Lys Gly Lys Glu His Ile Gln
                405                 410 taatgagcca ctcataggct ccaaatttat cgttcccttc attgttttca tcacttggtc  1302
ctcgtggttc acattaaatg tagacgcacg tgcattggat acagcgatca ccatacgtcg  1362
attagttcaa gcatcagagt cgtccgaggg aggcatcttg cccacatttg actcttcctc  1422
atcctctgaa tccgaagcaa caaccgtaga ttgcttgacg aattccttcg gcctaatgga  1482
gccttgcgcc aaactttctc atcccgaacg atattaatga tttccccagc aagcttattg  1542
tcccggtcct caagagcgtt ggtatcgacc acgacgtagg agttgcgttt catccagatt  1602
cttgaacgga agcgggaagg tagttcgacc aaaaccgtgt cttttgatgg cagttcgacc  1662
acatataaat tgttccccgt tgccttgatg actcgcgcga tttgctgtcc ctgttgaagc  1722
tcatctggag gggtcatagt ttcttccgct gttgcgagta ccttgcgccg tggtggtgcc  1782
atgatggtat attgcaattg ggatctcttt tcttggaacc taaattgtcg caatctctta  1842
gatgctgtct tgtatgaagc aattgctgat cagataagct gtggtgaggg gtagtcttat  1902
tgtgtttgat agcggagggg t                                            1923

<210> SEQ ID NO 4
<211> LENGTH: 413
<212> TYPE: PRT
<213> ORGANISM: Aspergillus oryzae

<400> SEQUENCE: 4

Met Glu Leu Lys His Phe Ile His Glu Leu Cys Leu Asn Pro Arg His
1               5                   10                  15

Thr Lys Trp Ile Ala Pro Leu Val Ile Gly Asp Ala Phe Leu Cys
            20                  25                  30

Ala Leu Ile Ile Trp Lys Ile Pro Tyr Thr Glu Ile Asp Trp Thr Thr
        35                  40                  45

Tyr Met Gln Gln Ile Ala Leu Tyr Ile Ser Gly Glu Arg Asp Tyr Thr
    50                  55                  60

Leu Ile Lys Gly Ser Thr Gly Pro Leu Val Tyr Pro Ala Ala His Val
65                  70                  75                  80

Tyr Ser Tyr Met Ala Leu Tyr His Leu Thr Asp Glu Gly Arg Asp Ile
                85                  90                  95
```

-continued

```
Leu Phe Gly Gln Ile Leu Phe Ala Val Leu Tyr Leu Val Thr Leu Ala
            100                 105                 110
Val Val Met Val Cys Tyr Arg Gln Ser Gly Ala Pro Pro Tyr Leu Phe
        115                 120                 125
Pro Leu Leu Val Leu Ser Lys Arg Leu His Ser Val Phe Val Leu Arg
    130                 135                 140
Leu Phe Asn Asp Gly Leu Ala Val Cys Ala Met Trp Ile Ala Ile Leu
145                 150                 155                 160
Leu Phe Gln Asn Lys Lys Trp Thr Ala Gly Val Thr Ala Trp Thr Val
                165                 170                 175
Gly Val Gly Ile Lys Met Thr Leu Leu Leu Ala Pro Ala Ile Ala
            180                 185                 190
Val Val Thr Val Leu Ser Leu Ser Leu Val Pro Ser Ile Arg Leu Gly
        195                 200                 205
Ile Leu Ala Leu Leu Ile Gln Val Leu Ala Ile Pro Phe Leu Gln
    210                 215                 220
Gly Asn Pro Ile Gly Tyr Val Ala Arg Ala Phe Glu Leu Thr Arg Gln
225                 230                 235                 240
Phe Met Phe Lys Trp Thr Val Asn Trp Arg Phe Val Gly Glu Asp Leu
                245                 250                 255
Phe Leu Ser Lys Gln Phe Ser Leu Ala Leu Leu Gly Leu His Ile Phe
            260                 265                 270
Leu Leu Gly Leu Phe Val Thr Thr Gly Trp Leu Arg Pro Ser Gly Ser
        275                 280                 285
Asn Val Pro Asp Phe Leu Arg Ser Leu Leu Gln Gly Arg Gln Arg Thr
    290                 295                 300
Val Val Leu Ser Lys Ser Phe Ile Met Thr Val Met Leu Thr Ser Leu
305                 310                 315                 320
Ala Ile Gly Leu Leu Cys Ala Arg Ser Leu His Tyr Gln Phe Phe Ala
                325                 330                 335
Tyr Leu Ser Trp Ala Thr Pro Cys Leu Leu Trp Arg Ala Arg Leu His
            340                 345                 350
Pro Ile Leu Ile Tyr Ala Ile Trp Ala Leu Gln Glu Trp Ala Trp Asn
        355                 360                 365
Val Tyr Pro Ser Thr Asn Ala Ser Ser Val Val Phe Ser Leu
    370                 375                 380
Ala Val Gln Val Phe Gly Val Leu Leu Asn Ser Arg Asn Ala Leu Ser
385                 390                 395                 400
Asp Ala Pro Pro Arg Arg Lys Gly Lys Glu His Ile Gln
                405                 410

<210> SEQ ID NO 5
<211> LENGTH: 22
<212> TYPE: DNA
<213> ORGANISM: Artificial Sequence
<220> FEATURE:
<223> OTHER INFORMATION: Alg3-ForScr primer

<400> SEQUENCE: 5
cggtttccct tcagtttcca gt                                              22

<210> SEQ ID NO 6
<211> LENGTH: 49
<212> TYPE: DNA
<213> ORGANISM: Artificial Sequence
<220> FEATURE:
```

<223> OTHER INFORMATION: Alg3-1 primer

<400> SEQUENCE: 6
gtaacgccag ggttttccca gtcacgacgt cataacttct ctcccctcc                49

<210> SEQ ID NO 7
<211> LENGTH: 49
<212> TYPE: DNA
<213> ORGANISM: Artificial Sequence
<220> FEATURE:
<223> OTHER INFORMATION: Alg3-2 primer

<400> SEQUENCE: 7
atccacttaa cgttactgaa atctccaact tcatggacac acacagacc                49

<210> SEQ ID NO 8
<211> LENGTH: 49
<212> TYPE: DNA
<213> ORGANISM: Artificial Sequence
<220> FEATURE:
<223> OTHER INFORMATION: Hph-F primer

<400> SEQUENCE: 8
ggtctgtgtg tgtccatgaa gttggagatt tcagtaacgt taagtggat                49

<210> SEQ ID NO 9
<211> LENGTH: 49
<212> TYPE: DNA
<213> ORGANISM: Artificial Sequence
<220> FEATURE:
<223> OTHER INFORMATION: Hph-R primer

<400> SEQUENCE: 9
gctactactg atccctctgc gtcggagaca gaagatgata ttgaaggag                49

<210> SEQ ID NO 10
<211> LENGTH: 49
<212> TYPE: DNA
<213> ORGANISM: Artificial Sequence
<220> FEATURE:
<223> OTHER INFORMATION: Alg3-3 primer

<400> SEQUENCE: 10
ctccttcaat atcatcttct gtctccgacg cagagggatc agtagtagc                49

<210> SEQ ID NO 11
<211> LENGTH: 49
<212> TYPE: DNA
<213> ORGANISM: Artificial Sequence
<220> FEATURE:
<223> OTHER INFORMATION: Alg3-4 primer

<400> SEQUENCE: 11
gcggataaca atttcacaca ggaaacagcc gtgagaggtt tgtagtacg                49

<210> SEQ ID NO 12
<211> LENGTH: 21
<212> TYPE: DNA
<213> ORGANISM: Artificial Sequence
<220> FEATURE:
<223> OTHER INFORMATION: Alg3-RevScr primer

<400> SEQUENCE: 12
aagctgagag cgacatcttc a                                              21

<210> SEQ ID NO 13
<211> LENGTH: 25
<212> TYPE: DNA
<213> ORGANISM: Artificial Sequence
<220> FEATURE:
<223> OTHER INFORMATION: hyg-RevScr primer

<400> SEQUENCE: 13
gtacttctac acagccatcg gtcca    25

<210> SEQ ID NO 14
<211> LENGTH: 25
<212> TYPE: DNA
<213> ORGANISM: Artificial Sequence
<220> FEATURE:
<223> OTHER INFORMATION: hyg-ForScr primer

<400> SEQUENCE: 14
gtacttctac acagccatcg gtcca    25

<210> SEQ ID NO 15
<211> LENGTH: 24
<212> TYPE: DNA
<213> ORGANISM: Artificial Sequence
<220> FEATURE:
<223> OTHER INFORMATION: pryGScr primer

<400> SEQUENCE: 15
tctgctgtct tgcatgaggt cctt    24

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
agcgtaggac aaggtcgtct ctgt    24

<210> SEQ ID NO 17
<211> LENGTH: 58
<212> TYPE: DNA
<213> ORGANISM: Artificial Sequence
<220> FEATURE:
<223> OTHER INFORMATION: 5-pyrG5F primer

<400> SEQUENCE: 17
gtaacgccag ggttttccca gtcacgacgt ttaaacatgc atcattctcc cgctttgt    58

<210> SEQ ID NO 18
<211> LENGTH: 43
<212> TYPE: DNA
<213> ORGANISM: Artificial Sequence
<220> FEATURE:
<223> OTHER INFORMATION: 5-pyrG3R primer

<400> SEQUENCE: 18
agaaagagtc accggtcacg acatcgccaa tcacctcaat cac    43

<210> SEQ ID NO 19
<211> LENGTH: 43
<212> TYPE: DNA
<213> ORGANISM: Artificial Sequence
<220> FEATURE:
<223> OTHER INFORMATION: ble5F primer

<400> SEQUENCE: 19
gtgattgagg tgattggcga tgtcgtgacc ggtgactctt tct         43

<210> SEQ ID NO 20
<211> LENGTH: 42
<212> TYPE: DNA
<213> ORGANISM: Artificial Sequence
<220> FEATURE:
<223> OTHER INFORMATION: Ble3R primer

<400> SEQUENCE: 20
tccaaccttg tagcaaccaa agcttcgagc gtcccaaaac ct         42

<210> SEQ ID NO 21
<211> LENGTH: 42
<212> TYPE: DNA
<213> ORGANISM: Artificial Sequence
<220> FEATURE:
<223> OTHER INFORMATION: Alg3-5F1 primer

<400> SEQUENCE: 21
aggttttggg acgctcgaag ctttggttgc tacaaggttg ga         42

<210> SEQ ID NO 22
<211> LENGTH: 29
<212> TYPE: DNA
<213> ORGANISM: Artificial Sequence
<220> FEATURE:
<223> OTHER INFORMATION: Alg3-3R1 primer

<400> SEQUENCE: 22
tcaagtagag cacagcaaat agtatctga         29

<210> SEQ ID NO 23
<211> LENGTH: 29
<212> TYPE: DNA
<213> ORGANISM: Artificial Sequence
<220> FEATURE:
<223> OTHER INFORMATION: Alg3-5F2 primer

<400> SEQUENCE: 23
tcagatacta tttgctgtgc tctacttga         29

<210> SEQ ID NO 24
<211> LENGTH: 42
<212> TYPE: DNA
<213> ORGANISM: Artificial Sequence
<220> FEATURE:
<223> OTHER INFORMATION: Alg3-3R2 primer

<400> SEQUENCE: 24
ttgatccttg tgccacacca tcctacgtgg tcatcgatac ca         42

<210> SEQ ID NO 25
<211> LENGTH: 42
<212> TYPE: DNA
<213> ORGANISM: Artificial Sequence
<220> FEATURE:
<223> OTHER INFORMATION: 3-pyrG5F primer

<400> SEQUENCE: 25
tggtatcgat gaccacgtag gatggtgtgg cacaaggatc aa         42

<210> SEQ ID NO 26
<211> LENGTH: 60

```
<212> TYPE: DNA
<213> ORGANISM: Artificial Sequence
<220> FEATURE:
<223> OTHER INFORMATION: 3=pyrG3R primer

<400> SEQUENCE: 26
gcggataaca atttcacaca ggaaacagcg tttaaactgt gccagtcaat tgtccgaagt    60

<210> SEQ ID NO 27
<211> LENGTH: 21
<212> TYPE: DNA
<213> ORGANISM: Artificial Sequence
<220> FEATURE:
<223> OTHER INFORMATION: Alg3seq-1 primer

<400> SEQUENCE: 27
tacagacgcg tgtacgcatg t                                               21

<210> SEQ ID NO 28
<211> LENGTH: 24
<212> TYPE: DNA
<213> ORGANISM: Artificial Sequence
<220> FEATURE:
<223> OTHER INFORMATION: Alg3seq-2 primer

<400> SEQUENCE: 28
tgctattgtc cacagatacc gaga                                            24

<210> SEQ ID NO 29
<211> LENGTH: 22
<212> TYPE: DNA
<213> ORGANISM: Artificial Sequence
<220> FEATURE:
<223> OTHER INFORMATION: Alg3seq-3 primer

<400> SEQUENCE: 29
gagctaacca gacagttcat gt                                              22

<210> SEQ ID NO 30
<211> LENGTH: 21
<212> TYPE: DNA
<213> ORGANISM: Artificial Sequence
<220> FEATURE:
<223> OTHER INFORMATION: Alg3seq-4 primer

<400> SEQUENCE: 30
tcgtcgtacc gcattgatcc t                                               21

<210> SEQ ID NO 31
<211> LENGTH: 413
<212> TYPE: PRT
<213> ORGANISM: Aspergillus nidulans

<400> SEQUENCE: 31

Met Ala Leu Thr Asp Leu Val Ser Gly Leu Cys Ser Asn Pro Lys His
1               5                   10                  15

Thr Lys Trp Ile Ala Pro Ile Leu Asn Ile Ala Asp Gly Leu Leu Cys
            20                  25                  30

Ala Phe Ile Ile Trp Lys Val Pro Tyr Thr Glu Ile Asp Trp Thr Thr
        35                  40                  45

Tyr Met Gln Gln Val Lys Leu Tyr Leu Ser Gly Glu Arg Asp Tyr Thr
    50                  55                  60

Leu Ile Lys Gly Ser Thr Gly Pro Leu Val Tyr Pro Ala Ala His Val
65                  70                  75                  80
```

```
Tyr Ser Tyr Ser Leu Phe His His Leu Thr Asp Glu Gly Arg Asp Ile
                85                  90                  95

Val Phe Gly Gln Ile Ile Phe Ala Phe Leu Tyr Leu Ile Cys Leu Thr
            100                 105                 110

Val Val Met Ala Cys Tyr Arg Arg Val Gly Ala Pro Pro Tyr Leu Phe
            115                 120                 125

Pro Leu Val Leu Ser Lys Arg Leu His Ser Val Tyr Met Leu Arg
130                 135                 140

Leu Phe Asn Asp Gly Leu Ala Ala Leu Ala Met Trp Gly Ser Ile Trp
145                 150                 155                 160

Leu Phe Ile Asn Arg Lys Trp Thr Pro Ala Val Val Leu Trp Ser Leu
                165                 170                 175

Gly Leu Gly Val Lys Met Thr Leu Ile Leu Leu Val Pro Ala Val Met
            180                 185                 190

Val Val Leu Ala Leu Ser Leu Asp Ile Gly Arg Cys Ile Arg Leu Ala
            195                 200                 205

Gly Leu Ala Leu Gly Ile Gln Ile Leu Leu Ala Ile Pro Phe Leu Lys
210                 215                 220

Thr Asn Pro Ser Gly Tyr Phe Glu Arg Ala Phe Glu Phe Gly Arg Gln
225                 230                 235                 240

Phe Met Phe Lys Trp Thr Val Asn Trp Arg Phe Val Gly Glu Asp Ile
                245                 250                 255

Phe Leu Ser Lys Gly Phe Trp Ala Gly Leu Ile Val Leu His Leu Leu
            260                 265                 270

Ile Leu Val Val Leu Gly Phe Thr Cys Phe Leu Asn Pro Ser Gly Thr
            275                 280                 285

Ser Leu Pro Asp Phe Ala Gly Arg Phe Leu Thr Gly Gln His Arg Gly
290                 295                 300

Ile Ala Leu His Pro Ser Phe Ile Met Ser Ala Leu Leu Thr Ser Leu
305                 310                 315                 320

Ser Val Gly Leu Leu Cys Ala Arg Ser Leu His Tyr Gln Phe Phe Ala
                325                 330                 335

Tyr Leu Ser Trp Ala Thr Pro Phe Leu Leu Trp Gln Ala Gly Tyr His
            340                 345                 350

Pro Ile Leu Val Tyr Ala Leu Trp Leu Val Gln Glu Trp Ala Trp Asn
            355                 360                 365

Val Tyr Pro Ser Thr Asn Leu Ser Ser Ala Ala Val Val Leu Leu Leu
370                 375                 380

Gly Ala Gln Val Leu Gly Val Leu Val Asn Arg Asp Arg Ala Phe Pro
385                 390                 395                 400

Ser Ser Pro Pro Thr Pro Lys Ala Lys Gln His Val Gln
                405                 410

<210> SEQ ID NO 32
<211> LENGTH: 434
<212> TYPE: PRT
<213> ORGANISM: Fusarium oxysporum

<400> SEQUENCE: 32

Met Pro Glu Ser Ala Ser Gly Thr Leu Ser Gln Gly Val Arg Phe Leu
1               5                   10                  15

Arg Asn Val Leu Asn Gly Arg His Ala Leu Ser Lys Leu Ile Pro Ile
            20                  25                  30

Ala Leu Trp Leu Val Asp Ala Leu Gly Cys Gly Leu Ile Ile Trp Lys
```

```
            35                  40                  45
Ile Pro Tyr Thr Glu Ile Asp Trp Val Ala Tyr Met Gln Gln Ile Ser
 50                  55                  60

Gln Phe Val Ser Gly Glu Arg Asp Tyr Thr Lys Met Glu Gly Asp Thr
 65                  70                  75                  80

Gly Pro Leu Val Tyr Pro Ala Ala His Val Tyr Thr Tyr Thr Gly Leu
                     85                  90                  95

Tyr Tyr Ile Thr Asp Lys Gly Thr Asn Ile Leu Leu Ala Gln Gln Ile
            100                 105                 110

Phe Ala Val Leu Tyr Met Ala Thr Leu Ala Val Val Met Leu Cys Tyr
            115                 120                 125

Trp Lys Ala Lys Val Pro Pro Tyr Met Phe Ile Phe Leu Ile Ala Ser
130                 135                 140

Lys Arg Leu His Ser Leu Phe Val Leu Arg Cys Phe Asn Asp Cys Phe
145                 150                 155                 160

Ala Val Phe Phe Leu Trp Leu Thr Ile Phe Leu Phe Gln Arg Arg Gln
                    165                 170                 175

Trp Thr Val Gly Ser Leu Val Tyr Ser Trp Gly Leu Gly Ile Lys Met
                180                 185                 190

Ser Leu Leu Leu Val Leu Pro Ala Ile Gly Val Ile Leu Phe Leu Gly
            195                 200                 205

Arg Gly Leu Trp Pro Ser Leu Arg Leu Ala Trp Leu Met Ala Gln Ile
        210                 215                 220

Gln Phe Ala Ile Gly Leu Pro Phe Ile Thr Lys Asn Pro Arg Gly Tyr
225                 230                 235                 240

Ala Ala Arg Ala Phe Glu Leu Ser Arg Gln Phe Gln Phe Lys Trp Thr
                    245                 250                 255

Val Asn Trp Arg Met Leu Gly Glu Val Phe Leu Ser Lys Tyr Phe
                260                 265                 270

Ala Leu Ser Leu Leu Ala Cys His Ile Leu Val Leu Ile Phe Ile
            275                 280                 285

Ser Lys Arg Trp Ile Gln Pro Thr Gly Arg Ser Leu Tyr Asp Leu Ile
        290                 295                 300

Pro Ser Phe Leu Arg Leu Lys Ser Pro Phe Thr Met Gln Glu Gln Leu
305                 310                 315                 320

Arg Ile Ser His Tyr Val Thr Pro Glu Tyr Ala Met Thr Thr Met Leu
                325                 330                 335

Thr Ala Asn Leu Ile Gly Leu Leu Phe Ala Arg Ser Leu His Tyr Gln
            340                 345                 350

Phe Tyr Ala Tyr Leu Ala Trp Ala Thr Pro Tyr Leu Leu Trp Arg Ala
        355                 360                 365

Thr Glu Asp Pro Val Ile Val Ala Ile Ile Trp Ala Ala Gln Glu Trp
        370                 375                 380

Ala Trp Asn Val Tyr Pro Ser Thr Asp Leu Ser Ser Thr Ile Ala Val
385                 390                 395                 400

Asn Thr Met Leu Ala Thr Val Val Leu Val Tyr Leu Gly Thr Ala Arg
                    405                 410                 415

Arg Ala Val Pro Ala Pro Ala Ala Gln Val Gly Asn Val Asp Asp Lys
                420                 425                 430

Asn Lys

<210> SEQ ID NO 33
<211> LENGTH: 502
```

<212> TYPE: PRT
<213> ORGANISM: Neurospora crassa

<400> SEQUENCE: 33

```
Met Ala Ala Pro Ser Ser Arg Pro Glu Ser Asn Pro Pro Leu Tyr Lys
1               5                   10                  15

Gln Ala Leu Asp Phe Ala Leu Asp Val Ala Asn Gly Arg His Ala Leu
            20                  25                  30

Ser Lys Leu Ile Pro Pro Ala Leu Phe Leu Val Asp Ala Leu Leu Cys
        35                  40                  45

Gly Leu Ile Ile Trp Lys Val Pro Tyr Thr Glu Ile Asp Trp Ala Ala
    50                  55                  60

Tyr Met Glu Gln Val Ser Gln Ile Leu Ser Gly Glu Arg Asp Tyr Thr
65                  70                  75                  80

Lys Val Arg Gly Gly Thr Gly Pro Leu Val Tyr Pro Ala Ala His Val
                85                  90                  95

Tyr Ile Tyr Thr Gly Leu Tyr His Leu Thr Asp Glu Gly Arg Asn Ile
            100                 105                 110

Leu Leu Ala Gln Gln Leu Phe Ala Gly Leu Tyr Met Val Thr Leu Ala
        115                 120                 125

Val Val Met Gly Cys Tyr Trp Gln Ala Lys Ala Pro Pro Tyr Leu Phe
    130                 135                 140

Pro Leu Leu Thr Leu Ser Lys Arg Leu His Ser Ile Phe Val Leu Arg
145                 150                 155                 160

Cys Phe Asn Asp Cys Phe Ala Val Leu Phe Leu Trp Leu Ala Ile Phe
                165                 170                 175

Phe Phe Gln Arg Arg Asn Trp Gln Ala Gly Ala Leu Leu Tyr Thr Leu
            180                 185                 190

Gly Leu Gly Val Lys Met Thr Leu Leu Ser Leu Pro Ala Val Gly
        195                 200                 205

Ile Val Leu Phe Leu Gly Ser Gly Ser Phe Val Thr Thr Leu Gln Leu
    210                 215                 220

Val Ala Thr Met Gly Leu Val Gln Ile Ala Ile Gly Leu Pro Phe Ile
225                 230                 235                 240

Thr Lys Asn Pro Arg Gly Tyr Ala Ala Arg Ala Phe Glu Leu Ser Arg
                245                 250                 255

Gln Phe Gln Phe Lys Trp Thr Val Asn Trp Arg Met Leu Gly Glu Glu
            260                 265                 270

Val Phe Leu Ser Lys Tyr Phe Ala Leu Ser Leu Leu Ala Cys His Ile
        275                 280                 285

Leu Val Leu Leu Ile Leu Ile Gly Val Pro Phe Leu Ala His Tyr Pro
    290                 295                 300

Thr Glu Tyr Leu Ser Arg Ala Phe Glu Leu Ser Arg Gln Phe Phe
305                 310                 315                 320

Lys Trp Thr Val Asn Trp Arg Phe Val Gly Glu Glu Ile Phe Leu Ser
                325                 330                 335

Lys Gly Phe Ala Leu Thr Leu Ala Leu His Val Leu Val Leu Gly
            340                 345                 350

Ile Phe Ile Thr Thr Arg Trp Ile Lys Pro Ala Arg Lys Ser Leu Val
        355                 360                 365

Gln Leu Ile Ser Pro Val Leu Leu Ala Gly Lys Pro Pro Leu Thr Val
    370                 375                 380

Pro Glu His Arg Ala Ala Ala Arg Asp Val Thr Pro Arg Tyr Ile Met
385                 390                 395                 400
```

```
Thr Thr Ile Leu Ser Ala Asn Ala Val Gly Leu Leu Phe Ala Arg Ser
                405                 410                 415

Leu His Tyr Gln Phe Tyr Ala Tyr Val Ala Trp Ser Thr Pro Phe Leu
                420                 425                 430

Leu Trp Arg Ala Gly Leu His Pro Val Leu Val Tyr Leu Leu Trp Ala
                435                 440                 445

Val His Glu Trp Ala Trp Asn Val Phe Pro Ser Thr Pro Ala Ser Ser
450                 455                 460

Ala Val Val Gly Val Leu Gly Val Thr Val Ala Gly Val Trp Phe
465                 470                 475                 480

Gly Ala Arg Glu Glu Trp Glu Pro Gly Met Lys Ser Ser Ser Lys Lys
                485                 490                 495

Glu Glu Ala Ala Met Arg
                500
```

<210> SEQ ID NO 34
<211> LENGTH: 434
<212> TYPE: PRT
<213> ORGANISM: Saccharomyces cerevisiae

<400> SEQUENCE: 34

```
Met Ala Gly Gly Lys Lys Ser Ser Thr Ala Pro Ser Arg Phe Gln
1               5                   10                  15

Lys Thr Leu Ser Ser Ile Trp Gln Asp Lys His Thr Val Leu Phe Lys
                20                  25                  30

Pro Glu Tyr Thr Leu Leu Val Thr Ala Val Leu Trp Phe Leu Glu Ile
                35                  40                  45

Ala Ile Asn Ile Trp Val Ile Gln Lys Val Ser Tyr Thr Glu Ile Asp
                50                  55                  60

Trp Lys Ala Tyr Met Asp Glu Val Glu Gly Val Ile Asn Gly Thr Tyr
65                  70                  75                  80

Asp Tyr Thr Gln Leu Lys Gly Asp Thr Gly Pro Leu Val Tyr Pro Ala
                85                  90                  95

Gly Phe Val Tyr Ile Phe Thr Gly Leu Tyr Tyr Leu Thr Asp His Gly
                100                 105                 110

His Asn Ile Arg Leu Gly Gln Tyr Val Phe Ala Val Ser Tyr Leu Ile
                115                 120                 125

Asn Leu Leu Leu Val Met Arg Ile Tyr His Arg Thr Lys Lys Val Pro
                130                 135                 140

Pro Tyr Val Phe Phe Ile Cys Cys Ala Ser Tyr Arg Ile His Ser
145                 150                 155                 160

Ile Phe Ile Leu Arg Leu Phe Asn Asp Pro Val Ala Met Met Leu Cys
                165                 170                 175

Phe Gly Ala Ile Asn Leu Phe Leu Asp Gly Arg Trp Thr Leu Gly Cys
                180                 185                 190

Ala Leu Tyr Ser Leu Ala Val Ser Val Lys Met Asn Val Leu Leu Phe
                195                 200                 205

Ala Pro Gly Leu Leu Phe Leu Leu Cys Glu Phe Gly Leu Trp Lys
                210                 215                 220

Thr Leu Pro Arg Leu Ala Leu Cys Ala Val Ile Gln Leu Leu Val Gly
225                 230                 235                 240

Leu Pro Phe Leu Ile Thr Tyr Pro Val Ser Tyr Ile Ala Asn Ala Phe
                245                 250                 255

Asp Leu Gly Arg Val Phe Ile His Phe Trp Ser Val Asn Phe Lys Phe
```

```
                     260                 265                 270
Val Pro Glu Arg Val Phe Val Ser Lys Glu Phe Ala Val Cys Leu Leu
            275                 280                 285

Ile Ala His Leu Phe Leu Leu Val Ala Phe Ala Leu Lys Arg Trp Lys
            290                 295                 300

Arg Ser Gly Ser Ser Ile Trp Thr Ile Leu Lys Asp Pro Ser Glu Arg
305                 310                 315                 320

Lys Glu Thr Ala His Lys Val Asn Ala Asp Gln Met Val Leu Ile Leu
                325                 330                 335

Phe Thr Ser Asn Phe Ile Gly Met Cys Phe Ser Arg Ser Leu His Tyr
            340                 345                 350

Gln Phe Tyr Val Trp Tyr Phe His Thr Leu Pro Tyr Leu Leu Trp Ser
            355                 360                 365

Gly Gly Val Lys Lys Leu Ala Arg Leu Leu Arg Val Leu Ile Leu Gly
            370                 375                 380

Leu Ile Glu Leu Ser Trp Asn Thr Tyr Pro Ser Thr Asn Tyr Ser Ser
385                 390                 395                 400

Leu Ser Leu His Val Cys His Leu Ile Ile Leu Leu Cys Leu Trp Leu
                405                 410                 415

Asn Pro Asn Pro Ala Ser Pro Ser His Arg Ser Glu Asn Lys Ala Lys
            420                 425                 430

Ser His

<210> SEQ ID NO 35
<211> LENGTH: 437
<212> TYPE: PRT
<213> ORGANISM: Arabidopsis thaliana

<400> SEQUENCE: 35

Met Ala Gly Ala Ser Ser Pro Ala Ser Leu Arg Ala Ser Arg Ser Arg
1               5                   10                  15

Arg Leu Gly Lys Glu Thr Asn Arg Ser Asp Leu Phe Lys Lys Pro Ala
                20                  25                  30

Val Pro Phe Ala Phe Ala Leu Ile Leu Ala Asp Ala Ile Leu Val Ala
            35                  40                  45

Leu Ile Ile Ala Tyr Val Pro Tyr Thr Lys Ile Asp Trp Asp Ala Tyr
        50                  55                  60

Met Ser Gln Val Ser Gly Phe Leu Gly Gly Glu Arg Asp Tyr Gly Asn
65              70                  75                  80

Leu Lys Gly Asp Thr Gly Pro Leu Val Tyr Pro Ala Gly Phe Leu Tyr
                85                  90                  95

Val Tyr Ser Ala Val Gln Asn Leu Thr Gly Gly Glu Val Tyr Pro Ala
            100                 105                 110

Gln Ile Leu Phe Gly Val Leu Tyr Ile Val Asn Leu Gly Ile Val Leu
        115                 120                 125

Ile Ile Tyr Val Lys Thr Asp Val Pro Trp Trp Ala Leu Ser Leu Leu
        130                 135                 140

Cys Leu Ser Lys Arg Ile His Ser Ile Phe Val Leu Arg Leu Phe Asn
145             150                 155                 160

Asp Cys Phe Ala Met Thr Leu Leu His Ala Ser Met Ala Leu Phe Leu
                165                 170                 175

Tyr Arg Lys Trp His Leu Gly Met Leu Val Phe Ser Gly Ala Val Ser
            180                 185                 190

Val Lys Met Asn Val Leu Leu Tyr Ala Pro Thr Leu Leu Leu Leu Leu
```

```
                    195                 200                 205
Leu Lys Ala Met Asn Ile Ile Gly Val Val Ser Ala Leu Ala Gly Ala
    210                 215                 220

Ala Leu Val Gln Ile Leu Val Gly Leu Pro Phe Leu Ile Thr Tyr Pro
225                 230                 235                 240

Val Ser Tyr Ile Ala Asn Ala Phe Asp Leu Gly Arg Val Phe Ile His
                245                 250                 255

Phe Trp Ser Val Asn Phe Lys Phe Val Pro Glu Arg Val Phe Val Ser
            260                 265                 270

Lys Glu Phe Ala Val Cys Leu Leu Ile Ala His Leu Phe Leu Leu Val
        275                 280                 285

Ala Phe Ala Asn Tyr Lys Trp Cys Lys His Glu Gly Ile Ile Gly
    290                 295                 300

Phe Met Arg Ser Arg His Phe Phe Leu Thr Leu Pro Ser Ser Leu Ser
305                 310                 315                 320

Phe Ser Asp Val Ser Ala Ser Arg Ile Ile Thr Lys Glu His Val Val
                325                 330                 335

Thr Ala Met Phe Val Gly Asn Phe Ile Gly Ile Val Phe Ala Arg Ser
            340                 345                 350

Leu His Tyr Gln Phe Tyr Ser Trp Tyr Phe Tyr Ser Leu Pro Tyr Leu
        355                 360                 365

Leu Trp Arg Thr Pro Phe Pro Thr Trp Leu Arg Leu Ile Met Phe Leu
    370                 375                 380

Gly Ile Glu Leu Cys Trp Asn Val Tyr Pro Ser Thr Pro Ser Ser Ser
385                 390                 395                 400

Gly Leu Leu Leu Cys Leu His Leu Ile Ile Leu Val Gly Leu Trp Leu
                405                 410                 415

Ala Pro Ser Val Asp Pro Tyr Gln Leu Lys Glu His Pro Lys Ser Gln
            420                 425                 430

Ile His Lys Lys Ala
        435

<210> SEQ ID NO 36
<211> LENGTH: 433
<212> TYPE: PRT
<213> ORGANISM: Homo sapiens

<400> SEQUENCE: 36

Arg Lys Arg Gly Arg Ser Gly Ser Ala Ala Gln Ala Glu Gly Leu Cys
1               5                   10                  15

Lys Gln Trp Leu Gln Arg Ala Trp Gln Glu Arg Arg Leu Leu Leu Arg
            20                  25                  30

Glu Pro Arg Tyr Thr Leu Leu Val Ala Ala Cys Leu Cys Leu Ala Glu
        35                  40                  45

Val Gly Ile Thr Phe Trp Val Ile His Arg Val Ala Tyr Thr Glu Ile
    50                  55                  60

Asp Trp Lys Ala Tyr Met Ala Glu Val Glu Gly Val Ile Asn Gly Thr
65                  70                  75                  80

Tyr Asp Tyr Thr Gln Leu Gln Gly Asp Thr Gly Pro Leu Val Tyr Pro
                85                  90                  95

Ala Gly Phe Val Tyr Ile Phe Met Gly Leu Tyr Tyr Ala Thr Ser Arg
            100                 105                 110

Gly Thr Asp Ile Arg Met Ala Gln Asn Ile Phe Ala Val Leu Tyr Leu
        115                 120                 125
```

```
Ala Thr Leu Leu Leu Val Phe Leu Ile Tyr His Gln Thr Cys Lys Val
    130                 135                 140
Pro Pro Phe Val Phe Phe Met Cys Cys Ala Ser Tyr Arg Val His
145                 150                 155                 160
Ser Ile Phe Val Leu Arg Leu Phe Asn Asp Pro Val Ala Met Val Leu
                165                 170                 175
Leu Phe Leu Ser Ile Asn Leu Leu Leu Ala Gln Arg Trp Gly Trp Gly
                180                 185                 190
Cys Cys Phe Phe Ser Leu Ala Val Ser Val Lys Met Asn Val Leu Leu
                195                 200                 205
Phe Ala Pro Gly Leu Leu Phe Leu Leu Thr Gln Phe Gly Phe Arg
210                 215                 220
Gly Ala Leu Pro Lys Leu Gly Ile Cys Ala Gly Leu Gln Val Val Leu
225                 230                 235                 240
Gly Leu Pro Phe Leu Leu Glu Asn Pro Ser Gly Tyr Leu Ser Arg Ser
                245                 250                 255
Phe Asp Leu Gly Arg Gln Phe Leu Phe His Trp Thr Val Asn Trp Arg
                260                 265                 270
Phe Leu Pro Glu Ala Leu Phe Leu His Arg Ala Phe His Leu Ala Leu
            275                 280                 285
Leu Thr Ala His Leu Thr Leu Leu Leu Phe Ala Leu Cys Arg Trp
    290                 295                 300
His Arg Thr Gly Glu Ser Ile Leu Ser Leu Leu Arg Asp Pro Ser Lys
305                 310                 315                 320
Arg Lys Val Pro Pro Gln Pro Leu Thr Pro Asn Gln Ile Val Ser Thr
                325                 330                 335
Leu Phe Thr Ser Asn Phe Ile Gly Ile Cys Phe Ser Arg Ser Leu His
                340                 345                 350
Tyr Gln Phe Tyr Val Trp Tyr Phe His Thr Leu Pro Tyr Leu Leu Trp
            355                 360                 365
Ala Met Pro Ala Arg Trp Leu Thr His Leu Leu Arg Leu Leu Val Leu
    370                 375                 380
Gly Leu Ile Glu Leu Ser Trp Asn Thr Tyr Pro Ser Thr Ser Cys Ser
385                 390                 395                 400
Ser Ala Ala Leu His Ile Cys His Ala Val Ile Leu Leu Gln Leu Trp
                405                 410                 415
Leu Gly Pro Gln Pro Phe Pro Lys Ser Thr Gln His Ser Lys Lys Ala
                420                 425                 430
His

<210> SEQ ID NO 37
<211> LENGTH: 1291
<212> TYPE: DNA
<213> ORGANISM: Aspergillus nidulans

<400> SEQUENCE: 37
aagcttcaag ctgtaaggat ttcggcacgg ctacggaaga cggagaagcc caccttcagt    60
ggactcgagt accatttaat tctatttgtg tttgatcgag acctaataca gcccctacaa   120
cgaccatcaa agtcgtatag ctaccagtga ggaagtggac tcaaatcgac ttcagcaaca   180
tctcctggat aaactttaag cctaaactat acagaataag atggtggaga gcttataccg   240
agctcccaaa tctgtccaga tcatggttga ccggtgcctg gatcttccta tagaatcatc   300
cttattcgtt gacctagctg attctggagt gacccagagg gtcatgactt gagcctaaaa   360
```

```
tccgccgcct ccaccatttg tagaaaaatg tgacgaactc gtgagctctg tacagtgacc    420
ggtgactctt tctggcatgc ggagagacgg acggacgcag agagaagggc tgagtaataa    480
gcgccactgc gccagacagc tctggcggct ctgaggtgca gtggatgatt attaatccgg    540
gaccggccgc ccctccgccc cgaagtggaa aggctggtgt gccctcgtt gaccaagaat     600 ctattgcatc atcggagaat atggagcttc atcgaatcac cggcagtaag cgaaggagaa    660
tgtgaagcca gggtgtata gccgtcggcg aaatagcatg ccattaacct aggtacagaa     720
gtccaattgc ttccgatctg gtaaaagatt cacgagatag taccttctcc gaagtaggta    780
gagcgagtac ccggcgcgta agctccctaa ttggcccatc cggcatctgt agggcgtcca    840
aatatcgtgc ctctcctgct tgcccggtg tatgaaaccg gaaaggccgc tcaggagctg     900
gccagcggcg cagaccggga acacaagctg gcagtcgacc catccggtgc ctgcactcg     960 acctgctgag gtccctcagt ccctggtagg cagctttgcc ccgtctgtcc gcccggtgtg   1020
tcggcggggt tgacaaggtc gttgcgtcag tccaacattt gttgccatat tttcctgctc   1080
tccccaccag ctgctctttt cttttctctt tcttttccca tcttcagtat attcatcttc   1140
ccatccaaga acctttattt cccctaagta agtactttgc tacatccata ctccatcctt   1200
cccatccctt attcctttga acctttcagt tcgagctttc ccacttcatc gcagcttgac   1260
taacagctac cccgcttgag cagacatcac a                                   1291

<210> SEQ ID NO 38
<211> LENGTH: 30
<212> TYPE: DNA
<213> ORGANISM: Artificial Sequence
<220> FEATURE:
<223> OTHER INFORMATION: gpdA5F primer

<400> SEQUENCE: 38
cgcagatctc aagctgtaag gatttcggca                                       30

<210> SEQ ID NO 39
<211> LENGTH: 40
<212> TYPE: DNA
<213> ORGANISM: Artificial Sequence
<220> FEATURE:
<223> OTHER INFORMATION: gpdA3R primer

<400> SEQUENCE: 39
caccgggccc atctcaaaca ttgtgatgtc tgctcaagcg                            40

<210> SEQ ID NO 40
<211> LENGTH: 1255
<212> TYPE: DNA
<213> ORGANISM: Aspergillus nidulans
<220> FEATURE:
<221> NAME/KEY: CDS
<222> LOCATION: (1)..(236)
<220> FEATURE:
<221> NAME/KEY: Intron
<222> LOCATION: (237)..(366)
<220> FEATURE:
<221> NAME/KEY: CDS
<222> LOCATION: (367)..(1252)

<400> SEQUENCE: 40 atg ttt gag atg ggc ccg gtg gga act cgt ctc ccc gcc atg acc tct     48
Met Phe Glu Met Gly Pro Val Gly Thr Arg Leu Pro Ala Met Thr Ser
1               5                   10                  15 cca gcg cac aac cac tac agc tac cac tct ccc acc tcc agc gac aga     96
Pro Ala His Asn His Tyr Ser Tyr His Ser Pro Thr Ser Ser Asp Arg
```

```
                20                  25                  30
ggc cgg tca agg cag aac tcg gat gcc atg gac atc cag tcc atc act       144
Gly Arg Ser Arg Gln Asn Ser Asp Ala Met Asp Ile Gln Ser Ile Thr
         35                  40                  45 gaa cga gag ccg gcg acc aga tac gcg gtt gcg ggc ggc cct gcg ccc       192
Glu Arg Glu Pro Ala Thr Arg Tyr Ala Val Ala Gly Gly Pro Ala Pro
 50                  55                  60 tgg aat cgc aac ggg tct ccg agc atg agc cct atg tat agc aa           236
Trp Asn Arg Asn Gly Ser Pro Ser Met Ser Pro Met Tyr Ser Asn
 65                  70                  75 gtacatctct cttacccctc cgtttctttc tgcttttcta ccaccccatc cctctttcca     296
gtctgagtcc aggcttgttc cgcttgaagt ggctaatgtg atcctcgtct tctctctttc     356
tgtgttttag c aat tcc gag cga aac cag ttt cat gaa gag aac gga cgc     406
             Asn Ser Glu Arg Asn Gln Phe His Glu Glu Asn Gly Arg
              80                  85                  90 acc tac cat ggc ttt cgc agg gga atg tat ttt ctt ccg tgc gat gag       454
Thr Tyr His Gly Phe Arg Arg Gly Met Tyr Phe Leu Pro Cys Asp Glu
             95                 100                 105 caa gaa cag gat cgc ctc gac atc ttc cat aag cta ttc acg gta gcg       502
Gln Glu Gln Asp Arg Leu Asp Ile Phe His Lys Leu Phe Thr Val Ala
        110                 115                 120 cgg gta tcg gag agt ctg atc tac gcg ccc cat cca acc aac ggc cgg       550
Arg Val Ser Glu Ser Leu Ile Tyr Ala Pro His Pro Thr Asn Gly Arg
125                 130                 135                 140 ttt ctg gac cta gga tgt gga act ggt atc tgg gcg atc gag gta gcg       598
Phe Leu Asp Leu Gly Cys Gly Thr Gly Ile Trp Ala Ile Glu Val Ala
                145                 150                 155 aac aag tac cct gat gcg ttt gtc gct ggt gtg gat ttg gct cct att       646
Asn Lys Tyr Pro Asp Ala Phe Val Ala Gly Val Asp Leu Ala Pro Ile
        160                 165                 170 cag cct ccg aac cac ccg aag aac tgc gag ttc tac gcg ccc ttc gac       694
Gln Pro Pro Asn His Pro Lys Asn Cys Glu Phe Tyr Ala Pro Phe Asp
                175                 180                 185 ttc gaa gcg cca tgg gcc atg ggg gag gat tcc tgg gat cta atc cat       742
Phe Glu Ala Pro Trp Ala Met Gly Glu Asp Ser Trp Asp Leu Ile His
190                 195                 200 ctg cag atg ggt tgc ggt agt gtc atg ggc tgg cca aac ttg tat cga       790
Leu Gln Met Gly Cys Gly Ser Val Met Gly Trp Pro Asn Leu Tyr Arg
205                 210                 215                 220 agg ata ttc gca cat ctc cgt ccc ggt gcc tgg ttt gag cag gtt gag       838
Arg Ile Phe Ala His Leu Arg Pro Gly Ala Trp Phe Glu Gln Val Glu
                225                 230                 235 atc gat ttc gag cct cga tgt gat gat cgg tca cta gat gga acg gca       886
Ile Asp Phe Glu Pro Arg Cys Asp Asp Arg Ser Leu Asp Gly Thr Ala
        240                 245                 250 ttg cgg cat tgg tac gat tgt ctt aaa cag gcg aca gca gag acc atg       934
Leu Arg His Trp Tyr Asp Cys Leu Lys Gln Ala Thr Ala Glu Thr Met
                255                 260                 265 cgg cca atc gcc cat agc tcc cgc gat aca ata aaa gac ctg cag gac       982
Arg Pro Ile Ala His Ser Ser Arg Asp Thr Ile Lys Asp Leu Gln Asp
        270                 275                 280 gct ggg ttc acg gag atc gac cat caa ata gtg gga ctc ccg ctc aac      1030
Ala Gly Phe Thr Glu Ile Asp His Gln Ile Val Gly Leu Pro Leu Asn
285                 290                 295                 300 ccg tgg cat cag gac gaa cac gag cgg aag gtg gca cgt tgg tat aac      1078
Pro Trp His Gln Asp Glu His Glu Arg Lys Val Ala Arg Trp Tyr Asn
                305                 310                 315 ctg gcc gtc tca gag agc atc gaa aac ctc agt ctg gct ccc ttc agt      1126
Leu Ala Val Ser Glu Ser Ile Glu Asn Leu Ser Leu Ala Pro Phe Ser
```

-continued

```
Leu Ala Val Ser Glu Ser Ile Glu Asn Leu Ser Leu Ala Pro Phe Ser
            320                 325                 330 cgt gtc tat cgc tgg ccc ctg gag aga atc cag caa ctc gcc gca gat    1174
Arg Val Tyr Arg Trp Pro Leu Glu Arg Ile Gln Gln Leu Ala Ala Asp
            335                 340                 345 gtg aag tcc gaa gca ttc aac aaa gag atc cat gcc tac aat ata ctg    1222
Val Lys Ser Glu Ala Phe Asn Lys Glu Ile His Ala Tyr Asn Ile Leu
350                 355                 360 cac ata tac cag gct agg aaa cca tta aga taa                        1255
His Ile Tyr Gln Ala Arg Lys Pro Leu Arg
365                 370

<210> SEQ ID NO 41
<211> LENGTH: 374
<212> TYPE: PRT
<213> ORGANISM: Aspergillus nidulans

<400> SEQUENCE: 41

Met Phe Glu Met Gly Pro Val Gly Thr Arg Leu Pro Ala Met Thr Ser
1               5                   10                  15

Pro Ala His Asn His Tyr Ser Tyr His Ser Pro Thr Ser Ser Asp Arg
                20                  25                  30

Gly Arg Ser Arg Gln Asn Ser Asp Ala Met Asp Ile Gln Ser Ile Thr
            35                  40                  45

Glu Arg Glu Pro Ala Thr Arg Tyr Ala Val Ala Gly Pro Ala Pro
50                  55                  60

Trp Asn Arg Asn Gly Ser Pro Ser Met Ser Pro Met Tyr Ser Asn Asn
65                  70                  75                  80

Ser Glu Arg Asn Gln Phe His Glu Glu Asn Gly Arg Thr Tyr His Gly
                85                  90                  95

Phe Arg Arg Gly Met Tyr Phe Leu Pro Cys Asp Glu Gln Glu Gln Asp
            100                 105                 110

Arg Leu Asp Ile Phe His Lys Leu Phe Thr Val Ala Arg Val Ser Glu
        115                 120                 125

Ser Leu Ile Tyr Ala Pro His Pro Thr Asn Gly Arg Phe Leu Asp Leu
    130                 135                 140

Gly Cys Gly Thr Gly Ile Trp Ala Ile Glu Val Ala Asn Lys Tyr Pro
145                 150                 155                 160

Asp Ala Phe Val Ala Gly Val Asp Leu Ala Pro Ile Gln Pro Pro Asn
                165                 170                 175

His Pro Lys Asn Cys Glu Phe Tyr Ala Pro Phe Asp Phe Glu Ala Pro
            180                 185                 190

Trp Ala Met Gly Glu Asp Ser Trp Asp Leu Ile His Leu Gln Met Gly
        195                 200                 205

Cys Gly Ser Val Met Gly Trp Pro Asn Leu Tyr Arg Arg Ile Phe Ala
    210                 215                 220

His Leu Arg Pro Gly Ala Trp Phe Glu Gln Val Glu Ile Asp Phe Glu
225                 230                 235                 240

Pro Arg Cys Asp Asp Arg Ser Leu Asp Gly Thr Ala Leu Arg His Trp
                245                 250                 255

Tyr Asp Cys Leu Lys Gln Ala Thr Ala Glu Thr Met Arg Pro Ile Ala
            260                 265                 270

His Ser Ser Arg Asp Thr Ile Lys Asp Leu Gln Asp Ala Gly Phe Thr
        275                 280                 285

Glu Ile Asp His Gln Ile Val Gly Leu Pro Leu Asn Pro Trp His Gln
    290                 295                 300
```

Asp Glu His Glu Arg Lys Val Ala Arg Trp Tyr Asn Leu Ala Val Ser
305                 310                 315                 320

Glu Ser Ile Glu Asn Leu Ser Leu Ala Pro Phe Ser Arg Val Tyr Arg
            325                 330                 335

Trp Pro Leu Glu Arg Ile Gln Gln Leu Ala Ala Asp Val Lys Ser Glu
        340                 345                 350

Ala Phe Asn Lys Glu Ile His Ala Tyr Asn Ile Leu His Ile Tyr Gln
    355                 360                 365

Ala Arg Lys Pro Leu Arg
    370

<210> SEQ ID NO 42
<211> LENGTH: 40
<212> TYPE: DNA
<213> ORGANISM: Artificial Sequence
<220> FEATURE:
<223> OTHER INFORMATION: LaeA5F primer

<400> SEQUENCE: 42
cgcttgagca gacatcacaa tgtttgagat gggcccggtg                         40

<210> SEQ ID NO 43
<211> LENGTH: 29
<212> TYPE: DNA
<213> ORGANISM: Artificial Sequence
<220> FEATURE:
<223> OTHER INFORMATION: LaeA3R primer

<400> SEQUENCE: 43
cgcagatctg aggattatga aagggagc                                      29

<210> SEQ ID NO 44
<211> LENGTH: 2866
<212> TYPE: DNA
<213> ORGANISM: Artificial Sequence
<220> FEATURE:
<223> OTHER INFORMATION: pGPDA promoter LeaA fragment

<400> SEQUENCE: 44
aagcttcaag ctgtaaggat tcggcacgg ctacggaaga cggagaagcc caccttcagt     60
ggactcgagt accatttaat tctatttgtg tttgatcgag acctaataca gcccctacaa   120
cgaccatcaa agtcgtatag ctaccagtga ggaagtggac tcaaatcgac ttcagcaaca   180
tctcctggat aaactttaag cctaaactat acagaataag atggtggaga gcttataccg   240
agctcccaaa tctgtccaga tcatggttga ccggtgcctg gatcttccta tagaatcatc   300
cttattcgtt gacctagctg attctggagt gacccagagg gtcatgactt gagcctaaaa   360
tccgccgcct ccaccatttg tagaaaaatg tgacgaactc gtgagctctg tacagtgacc   420
ggtgactctt tctggcatgc ggagagacgg acggacgcag agagaagggc tgagtaataa   480
gcgccactgc gccagacagc tctggcggct ctgaggtgca gtggatgatt attaatccgg   540
gaccggccgc cctccgccc gaagtggaa aggctggtgt gcccctcgtt gaccaagaat   600
ctattgcatc atcggagaat atggagcttc atcgaatcac cggcagtaag cgaaggagaa   660
tgtgaagcca gggtgtata gccgtcggcg aaatagcatg ccattaacct aggtacagaa   720
gtccaattgc ttccgatctg gtaaaagatt cacgagatag taccttctcc gaagtaggta   780
gagcgagtac ccggcgcgta agctccctaa ttggcccatc cggcatctgt agggcgtcca   840
aatatcgtgc ctctcctgct tgcccggtg tatgaaaccg gaaaggccgc tcaggagctg   900

```
gccagcggcg cagaccggga acacaagctg gcagtcgacc catccggtgc tctgcactcg    960
acctgctgag gtccctcagt ccctggtagg cagctttgcc ccgtctgtcc gcccggtgtg   1020
tcggcggggt tgacaaggtc gttgcgtcag tccaacattt gttgccatat tttcctgctc   1080
tccccaccag ctgctctttt cttttctctt tcttttccca tcttcagtat attcatcttc   1140
ccatccaaga acctttattt cccctaagta agtactttgc tacatccata ctccatcctt   1200
cccatccctt attcctttga acctttcagt tcgagctttc ccacttcatc gcagcttgac   1260
taacagctac cccgcttgag cagacatcac aatgtttgag atgggcccgg tgggaactcg   1320
tctccccgcc atgacctctc cagcgcacaa ccactacagc taccactctc ccacctccag   1380
cgacagaggc cggtcaaggc agaactcgga tgccatggac atccagtcca tcactgaacg   1440
agagccggcg accagatacg cggttgcggg cggccctgcg ccctggaatc gcaacgggtc   1500
tccgagcatg agccctatgt atagcaagta catctctctt accctccgt ttctttctgc   1560 ttttctacca ccccatccct ctttccagtc tgagtccagg cttgttccgc ttgaagtggc   1620
taatgtgatc ctcgtcttct ctctttctgt gttttagcaa ttccgagcga aaccagtttc   1680
atgaagagaa cggacgcacc taccatggct ttcgcagggg aatgtatttt cttccgtgcg   1740
atgagcaaga acaggatcgc ctcgacatct tccataagct attcacggta gcgcgggtat   1800
cggagagtct gatctacgcg ccccatccaa ccaacggccg gtttctggac ctaggatgtg   1860
gaactggtat ctgggcgatc gaggtagcga acaagtaccc tgatgcgttt gtcgctggtg   1920
tggatttggc tcctattcag cctccgaacc acccgaagaa ctgcgagttc tacgcgccct   1980
tcgacttcga agcgccatgg gccatggggg aggattcctg ggatctaatc catctgcaga   2040
tgggttgcgg tagtgtcatg ggctggccaa acttgtatcg aaggatattc gcacatctcc   2100
gtcccggtgc ctggtttgag caggttgaga tcgatttcga gcctcgatgt gatgatcggt   2160
cactagatgg aacggcattg cggcattggt acgattgtct taaacaggcg acagcagaga   2220
ccatgcggcc aatcgcccat agctcccgcg atacaataaa agacctgcag gacgctgggt   2280
tcacggagat cgaccatcaa atagtgggac tcccgctcaa cccgtggcat caggacgaac   2340
acgagcggaa ggtggcacgt tggtataacc tggccgtctc agagagcatc gaaaacctca   2400
gtctggctcc cttcagtcgt gtctatcgct ggcccctgga gagaatccag caactcgccg   2460
cagatgtgaa gtccgaagca ttcaacaaag agatccatgc ctacaatata ctgcacatat   2520
accaggctag gaaaccatta agataagagc aaaaggcgac cacatccagg aacgcaaaac   2580
gaaaaggagg aaaactgcta gcgcaagttt atgtcacgct ggcacacgcc cagccatcag   2640
aaatctcaac agcgaaagtt atgaaccgca tcaaccgagt atgaacgaca attcgtccat   2700
cacacaccct tcggttcctc tcgcaggccc agcatggcgc cctatcaacc tgctttacga   2760
cgtcgtatat actggcgaag tatcctctct atctactctg gcgctctaga taccgtgaag   2820
atgcagacaa aattggccga gctcccttct cataatcctc aagctt            2866

<210> SEQ ID NO 45
<211> LENGTH: 1279
<212> TYPE: DNA
<213> ORGANISM: Aspergillus niger

<400> SEQUENCE: 45
atgcatcatt ctcccgcttt gttttggcc caaactaac cgagtaggtg tggcatttgc     60
gggcatgatg tttcaactac cgctgatcat tatcaccgcc ccattagaga agatccaaga   120
```

```
ccctactggg aaggtgatag gcaattccat tttctgggtt agttttttgtc ttgtcggcca    180 gcctttggga gctttgctgt acttctttgc ctggcaagcg aagtatggca gtgtgagccg    240
aatgtgaatg taaaagcacg cacgtgtccg ctgtttgtca tagatgtaaa taaatgccaa    300
caacttcagc catttttgga aaagcaaagc aaccgaagta aacgatcctg taccatcagc    360
gctcctcaca atggaatctt ttagatgttt ctgttccatt catcttgctt actgcaatgt    420
tcttttcgcg tttgactaat tctccggatg ttgaatggca acgctgtcgg cgtcgggtct    480
tcagggatcc gccaaggatg ctctggatcc gcatccggcc gctcttgcgc cccatcaatc    540
gcccgactat aaatcgaact actttcggca tcttctagac ttcctaatac cgcctagtca    600
tagcagattc aagctgagaa caccacaagt aaatatcacc catcatgctt accctgaccg    660
tccctgaaaa ctacgggtat gtgccaattc tacaattcct tgcagacaat gccattctcc    720
ccatgaagtc tgatgctaac tatcctgcag ctctgtcatt gccgtcgctc tgggtgccat    780
ccccgtcctg agcttcgtcc atggcgccgt cgtgtctcgt ctccgcaagg aagctgattg    840
cccctaccct cactgctatg cgaccgtaga gcagtgcaag accaacgtaa gccaacctca    900
cacaaacagg attcctcgag ctaacataca ttccgaaccg tgcagcccaa ggccgagcag    960
ttcaactgcg ctcagcgcgc tcatgccaac ttccttgaga ctccagcca aactatgctc    1020 ttcctcctgg tagctggact gaagtacccc cagttggcga ctggcctcgg aagcatctgg    1080
gtcctcggtc gctcactgtt cctttacgga tatgtgtact ccggcaagcc gcggggtcgc    1140
ggtcgtttgt acggcagctt ctacttgctt gcacagggag ctctctgggg cttgacgtct    1200
tttggagttg cgagggagtt gatttcctac ttctaagttt ggactgaatc cgtggtgtga    1260
ttgaggtgat tggcgatgt                                                 1279

<210> SEQ ID NO 46
<211> LENGTH: 472
<212> TYPE: DNA
<213> ORGANISM: Aspergillus nidulans
<220> FEATURE:
<221> NAME/KEY: misc_feature
<222> LOCATION: (361)..(361)
<223> OTHER INFORMATION: n is a, c, g, or t

<400> SEQUENCE: 46
ggaccgatgg ctgtgtagaa gtactcgccg atagtggaaa ccgacgcccc agcactcgtc     60
cgagggcaaa ggaatagagt agatgccgac cgcgggatcc acttaacgtt actgaaatca    120
tcaaacagct tgacgaatct ggatataaga tcgttggtgt cgatgtcagc tccggagttg    180
agacaaatgg tgttcaggat ctcgataaga tacgttcatt tgtccaagca gcaaagagtg    240
ccttctagtg atttaatagc tccatgtcaa caagaataaa acgcgttttc gggtttacct    300
cttccagata cagctcatct gcaatgcatt aatgcattga ctgcaaccta gtaacgcctt    360
ncaggctccg gcgaagagaa gaatagctta gcagagctat tttcattttc gggagacgag    420
atcaagcaga tcaacggtcg tcaagagacc tacgagactg aggaatccgc tc            472

<210> SEQ ID NO 47
<211> LENGTH: 2005
<212> TYPE: DNA
<213> ORGANISM: Aspergillus oryzae

<400> SEQUENCE: 47
tctgacagac gggcaattga ttacgggatc ccattggtaa cgaaatgtaa aagctaggag     60
atcgtccgcc gatgtcagga tgatttcact tgtttcttgt ccggctcacc ggtcaaagct    120
```

```
aaagaggagc aaaaggaacg gatagaatcg ggtgccgctg atctatacgg tatagtgccc      180
ttatcacgtt gactcaaccc atgctattta actcaacccc tccttctgaa ccccaccatc      240
ttcttccttt tcctctcatc ccacacaatt ctctatctca gatttgaatt ccaaaagtcc      300
tcggacgaaa ctgaacaagt cttcctccct tcgataaacc tttggtgatt ggaataactg      360
accatcttct atagttccca aaccaaccga caatgtaaat acactcctcg attagccctc      420
tagagggcat acgatggaag tcatggaata cttttggctg gactctcaca atgatcaagg      480
tatcttaggt aacgtctttg gcgtgggccg gtgttcgttc ccagtcatcg atgcattcac      540
atgccctccc taagctgggc cctagactct aggatcctag tctagaagga catggcatcg      600
atggactggg ttcgttctga gattatacgg ctaaaacttg atctggataa taccagcgaa      660
aagggtcatg ccttctctcg ttcttcctgt tgatggaatg gctaacagat gatagtcatt      720
gcaacttgaa acatgtctcc tccagctgcc atctacgaac ccactgtggc cgctaccggc      780
ctcaagggta aggtcgtggt ttctgagacc gtccccgttg agggagcttc tcagaccaag      840
ctgttggacc atttcggtgg caagtgggac gagttcaagt tcgcccctat ccgcgaaagc      900
caggtctctc gtgccatgac cagacgttac tttgaggacc tggacaagta cgctgaaagt      960
gacgttgtca ttgttggtgc tggttcctgc ggtctgagca ctgcgtacgt cttggccaag     1020
gctcgtccgg acctgaagat tgctatcgtc gaggccagcg tctctcctgg tcagtagtcc     1080
atgatggatt gccttgcact cagctttccg gaactaacgt gcaataggtg gcggtgcctg     1140
gttgggtggc caactctttt ctgctatggt catgcgccgt cccgcggaag tcttcctgaa     1200
cgagctgggt gttccttacg aagaggacgc aaaccccaac tacgttgtcg tcaagcacgc     1260
ctccctgttt acctcgacac tcatgtcgaa ggttctctcc ttccccaatg tcaagctctt     1320
caatgctacc gctgttgagg acttgatcac ccgtccgacc gagaacggca acccccagat     1380
tgctggtgtt gtcgtcaact ggacgctggt caccccttcac cacgatgatc actcctgcat     1440
ggaccccaac actatcaacg ctcctgtcat catcagtacc actggtcacg atgggccatt     1500
cggcgccttc tgtgcgaagc gcttggtgtc catgggcagc gtcgacaagc taggtggcat     1560
gcgtggtctc gacatgaact cggccgagga tgccatcgtc aagaacaccc gcgaggttac     1620
taagggcttg ataatcggcg gtatggagct gtctgaaatt gatggctttta accgcatggg     1680 ccctaccttc ggtgccatgg ttctcagtgg tgtcaaggct gccgaggagg cattgaaggt     1740
gttcgacgag cgtcagcgcg agtgtgctga gtaaatgact cactacccga atgggttcag     1800
tgcatgaacc ggatttgtct tacggtcttt gacgatagggg gaatgatgat tatgtgatag     1860
ttctgagatt tgaatgaact cgttagctcg taatccacat gcatatgtaa atggctgtgt     1920
cccgtatgta acgtggggc attctagaat aattatgtgt aacaagaaag acagtataat     1980
acaaacaaag atgcaagagc ggctc                                         2005
```

<210> SEQ ID NO 48
<211> LENGTH: 1052
<212> TYPE: DNA
<213> ORGANISM: Aspergillus niger

<400> SEQUENCE: 48

```
gtcatcgcag ataagcactg ctgtcttgca tccaagtcag cgtcagcaga aatacgggac       60
ttccgaaagt atatggcaaa attaaagaac ttgactctcc agcaatgttt tgccctgacc      120
gtcgctaaaa cgttactacc cctataccccg tctgtttgtc ccagcccgag gcattaggtc      180
```

```
tgactgacag cacggcgcca tgcgggcttg ggacgccatg tccgtcgcgt gataagggtt      240
gatccatgca gctactatcc ttccatcgtt ccattcccat ccttgtccta tctccatcct      300
tgaaacttta ctagtttagt tggatgctcg agcttgctct cggctactcc gtccaatgga      360
taagaccccg atgccggtcc tcattggtct ccagctggta tcgccccaac cttcgtgtga      420
tcgcctctct gcttcccctc atcatcatta ctaactagta catccaaaag ccatcccagt      480
gcttcccctc acccttgccc aagacattcc aagtgggcct tcggctggaa acatggacc       540 cattggttcc atcgataagc tagctcctcg tccgttaccc cagattgata ccagataaca      600
ttgaccagcg gcttatcacc gaggtctgcg ggtgagaccc cccctgcgac aagttagata      660
aaagaaactc gcctcattgt gcttccgatg gggtcggatg acgagccttc ggaaagagct      720
ggcgcctctt taaggggac agctgtcgcc aagttgtgaa attctccgat aactactaac       780
aatctctccc ttccttcccg ctactgtggt caccaaatca actctctttt ctcggccaag      840
atctaacatg gcggatgaga agactgaaaa gtctcccccca ccgatgacgg tggatgagga     900
gactggcaca acagaggaaa ttgacccgac aatggcaaag catacgaagg atgcagacga      960
ggcactggcg gtcttcgaag acctccatgg tgaagtcatc acacttgatg aggagacaaa     1020
caaaaggata cttcggacaa ttgactggca ca                                    1052

<210> SEQ ID NO 49
<211> LENGTH: 58
<212> TYPE: DNA
<213> ORGANISM: Artificial Sequence
<220> FEATURE:
<223> OTHER INFORMATION: pyrGU5F primer

<400> SEQUENCE: 49
gtaacgccag ggttttccca gtcacgacgt ttaaacatgc atcattctcc cgctttgt        58

<210> SEQ ID NO 50
<211> LENGTH: 49
<212> TYPE: DNA
<213> ORGANISM: Artificial Sequence
<220> FEATURE:
<223> OTHER INFORMATION: pyrGU3R primer

<400> SEQUENCE: 50
tgccgaaatc cttacagctt gaagcttcat cgccaatcac ctcaatcac                  49

<210> SEQ ID NO 51
<211> LENGTH: 49
<212> TYPE: DNA
<213> ORGANISM: Artificial Sequence
<220> FEATURE:
<223> OTHER INFORMATION: Trp5F primer

<400> SEQUENCE: 51
agctcccttc tcataatcct caagcttgga ccgatggctg tgtagaagt                  49

<210> SEQ ID NO 52
<211> LENGTH: 46
<212> TYPE: DNA
<213> ORGANISM: Artificial Sequence
<220> FEATURE:
<223> OTHER INFORMATION: Trp3R primer

<400> SEQUENCE: 52
cgtaatcaat tgcccgtctg tcagagagcg gattcctcag tctcgt                     46
```

```
<210> SEQ ID NO 53
<211> LENGTH: 46
<212> TYPE: DNA
<213> ORGANISM: Artificial Sequence
<220> FEATURE:
<223> OTHER INFORMATION: PTR5F primer

<400> SEQUENCE: 53
acgagactga ggaatccgct ctctgacaga cgggcaattg attacg          46

<210> SEQ ID NO 54
<211> LENGTH: 45
<212> TYPE: DNA
<213> ORGANISM: Artificial Sequence
<220> FEATURE:
<223> OTHER INFORMATION: PTR3R primer

<400> SEQUENCE: 54
acagcagtgc ttatctgcga tgacgagccg ctcttgcatc tttgt           45

<210> SEQ ID NO 55
<211> LENGTH: 45
<212> TYPE: DNA
<213> ORGANISM: Artificial Sequence
<220> FEATURE:
<223> OTHER INFORMATION: PyrGD5F primer

<400> SEQUENCE: 55
acaaagatgc aagagcggct cgtcatcgca gataagcact gctgt           45

<210> SEQ ID NO 56
<211> LENGTH: 44
<212> TYPE: DNA
<213> ORGANISM: Artificial Sequence
<220> FEATURE:
<223> OTHER INFORMATION: PyrGD3R primer

<400> SEQUENCE: 56
tgagacgctg tttcaccgag tacatcgcca atcacctcaa tcac            44

<210> SEQ ID NO 57
<211> LENGTH: 7689
<212> TYPE: DNA
<213> ORGANISM: Artificial Sequence
<220> FEATURE:
<223> OTHER INFORMATION: transgene
<220> FEATURE:
<221> NAME/KEY: misc_feature
<222> LOCATION: (4513)..(4513)
<223> OTHER INFORMATION: n is a, c, g, or t

<400> SEQUENCE: 57
gtttaaacat gcatcattct cccgctttgt ttttgggccc aaactaaccg agtaggtgtg    60
gcatttgcgg gcatgatgtt tcaactaccg ctgatcatta tcaccgcccc attagagaag   120
atccaagacc ctactgggaa ggtgataggc aattccattt tctgggttag tttttgtctt   180
gtcggccagc ctttgggagc tttgctgtac ttctttgcct ggcaagcgaa gtatggcagt   240
gtgagccgaa tgtgaatgta aaagcacgca cgtgtccgct gtttgtcata gatgtaaata   300
aatgccaaca acttcagcca ttttttgaaa agcaaagcaa ccgaagtaaa cgatcctgta   360
ccatcagcgc tcctcacaat ggaatctttt agatgtttct gttccattca tcttgcttac   420
tgcaatgttc ttttcgcgtt tgactaattc tccggatgtt gaatggcaac gctgtcggcg   480
tcgggtcttc agggatccgc caaggatgct ctggatccgc atccggccgc tcttgcgccc   540
```

```
catcaatcgc ccgactataa atcgaactac tttcggcatc ttctagactt cctaataccg    600
cctagtcata gcagattcaa gctgagaaca ccacaagtaa atatcaccca tcatgcttac    660
cctgaccgtc cctgaaaact acgggtatgt gccaattcta caattccttg cagacaatgc    720
cattctcccc atgaagtctg atgctaacta tcctgcagct ctgtcattgc cgtcgctctg    780
ggtgccatcc ccgtcctgag cttcgtccat ggcgccgtcg tgtctcgtct ccgcaaggaa    840
gctgattgcc cctaccctca ctgctatgcg accgtagagc agtgcaagac caacgtaagc    900
caacctcaca caaacaggat tcctcgagct aacatacatt ccgaaccgtg cagcccaagg    960
ccgagcagtt caactgcgct cagcgcgctc atgccaactt ccttgagaac tccagccaaa   1020
ctatgctctt cctcctggta gctggactga agtaccccca gttggcgact ggcctcggaa   1080
gcatctgggt cctcggtcgc tcactgttcc tttacggata tgtgtactcc ggcaagccgc   1140
ggggtcgcgg tcgtttgtac ggcagcttct acttgcttgc acaggagct ctctggggct    1200 tgacgtcttt tggagttgcg agggagttga tttcctactt ctaagtttgg actgaatccg   1260
tggtgtgatt gaggtgattg gcgatgaagc ttcaagctgt aaggatttcg gcacggctac   1320
ggaagacgga gaagcccacc ttcagtggac tcgagtacca tttaattcta tttgtgtttg   1380
atcgagacct aatacagccc ctacaacgac catcaaagtc gtatagctac cagtgaggaa   1440
gtggactcaa atcgacttca gcaacatctc ctggataaac tttaagccta aactatacag   1500
aataagatgg tggagagctt ataccgagct cccaaatctg tccagatcat ggttgaccgg   1560
tgcctggatc ttcctataga atcatcctta ttcgttgacc tagctgattc tggagtgacc   1620
cagagggtca tgacttgagc ctaaaatccg ccgcctccac catttgtaga aaatgtgac    1680 gaactcgtga gctctgtaca gtgaccggtg actctttctg gcatgcggag agacggacgg   1740
acgcagagag aagggctgag taataagcgc cactgcgcca gacagctctg gcggctctga   1800
ggtgcagtgg atgattatta atccgggacc ggccgcccct ccgccccgaa gtggaaaggc   1860
tggtgtgccc ctcgttgacc aagaatctat tgcatcatcg gagaatatgg agcttcatcg   1920
aatcaccggc agtaagcgaa ggagaatgtg aagccagggg tgtatagccg tcggcgaaat   1980
agcatgccat taacctaggt acagaagtcc aattgcttcc gatctggtaa aagattcacg   2040
agatagtacc ttctccgaag taggtagagc gagtacccgg cgcgtaagct ccctaattgg   2100
cccatccggc atctgtaggg cgtccaaata tcgtgcctct cctgctttgc ccggtgtatg   2160
aaaccggaaa ggccgctcag gagctggcca gcggcgcaga ccgggaacac aagctggcag   2220
tcgacccatc cggtgtctg cactcgacct gctgaggtcc ctcagtccct ggtaggcagc    2280
tttgccccgt ctgtccgccc ggtgtgtcgg cggggttgac aaggtcgttg cgtcagtcca   2340
acatttgttg ccatattttc ctgctctccc caccagctgc tcttttcttt tctctttctt   2400
ttcccatctt cagtatattc atcttcccat ccaagaacct ttatttcccc taagtaagta   2460
ctttgctaca tccatactcc atccttccca tcccttattc ctttgaacct ttcagttcga   2520
gctttcccac ttcatcgcag cttgactaac agctaccccg cttgagcaga catcacaatg   2580
tttgagatgg gcccggtggg aactcgtctc cccgccatga cctctccagc gcacaaccac   2640
tacagctacc actctcccac ctccagcgac agaggccggt caaggcagaa tcggatgcc    2700 atggacatcc agtccatcac tgaacgagag ccggcgacca gatacgcggt tgcgggcggc   2760
cctgcgccct ggaatcgcaa cgggtctccg agcatgagcc ctatgtatag caagtacatc   2820
tctcttaccc ctccgtttct ttctgctttt ctaccacccc atccctcttt ccagtctgag   2880
tccaggcttg ttccgcttga agtggctaat gtgatcctcg tcttctctct ttctgtgttt   2940
```

```
tagcaattcc gagcgaaacc agtttcatga agagaacgga cgcacctacc atggctttcg    3000
caggggaatg tattttcttc cgtgcgatga gcaagaacag gatcgcctcg acatcttcca    3060
taagctattc acggtagcgc gggtatcgga gagtctgatc tacgcgcccc atccaaccaa    3120
cggccggttt ctggacctag gatgtggaac tggtatctgg gcgatcgagg tagcgaacaa    3180
gtaccctgat gcgtttgtcg ctggtgtgga tttggctcct attcagcctc cgaaccaccc    3240
gaagaactgc gagttctacg cgcccttcga cttcgaagcg ccatgggcca tgggggagga    3300
ttcctgggat ctaatccatc tgcagatggg ttgcggtagt gtcatgggct ggccaaactt    3360
gtatcgaagg atattcgcac atctccgtcc cggtgcctgg tttgagcagg ttgagatcga    3420
tttcgagcct cgatgtgatg atcggtcact agatggaacg gcattgcggc attggtacga    3480
ttgtcttaaa caggcgacag cagagaccat gcggccaatc gcccatagct cccgcgatac    3540 aataaagac ctgcaggacg ctgggttcac ggagatcgac catcaaatag tgggactccc    3600
gctcaacccg tggcatcagg acgaacacga gcggaaggtg gcacgttggt ataacctggc    3660
cgtctcagag agcatcgaaa acctcagtct ggctccsttc agtcgtgtct atcgctggcc    3720
cctggagaga atccagcaac tcgccgcaga tgtgaagtcc gaagcattca acaaagagat    3780
ccatgcctac aatatactgc acatatacca ggctaggaaa ccattaagat aagagcaaaa    3840
ggcgaccaca tccaggaacg caaaacgaaa aggaggaaaa ctgctagcgc aagtttatgt    3900
cacgctggca cacgcccagc catcagaaat ctcaacagcg aaagttatga accgcatcaa    3960
ccgagtatga acgacaattc gtccatcaca caccccttcgg ttcctctcgc aggcccagca    4020
tggcgcccta tcaacctgct ttacgacgtc gtatatactg gcgaagtatc ctctctatct    4080
actctggcgc tctagatacc gtgaagatgc agacaaaatt ggccgagctc ccttctcata    4140
atcctcaagc ttggaccgat ggctgtgtag aagtactcgc cgatagtgga aaccgacgcc    4200
ccagcactcg tccgagggca aaggaataga gtagatgccg accgcgggat ccacttaacg    4260
ttactgaaat catcaaacag cttgacgaat ctggatataa gatcgttggt gtcgatgtca    4320
gctccggagt tgagacaaat ggtgttcagg atctcgataa gatacgttca tttgtccaag    4380
cagcaaagag tgccttctag tgatttaata gctccatgtc aacaagaata aaacgcgttt    4440
tcgggtttac ctcttccaga tacagctcat ctgcaatgca ttaatgcatt gactgcaacc    4500
tagtaacgcc ttncaggctc cggcgaagag aagaatagct tagcagagct atttttcattt    4560 tcgggagacg agatcaagca gatcaacggt cgtcaagaga cctacgagac tgaggaatcc    4620
gctctctgac agacgggcaa ttgattacgg gatcccattg gtaacgaaat gtaaaagcta    4680
ggagatcgtc cgccgatgtc aggatgattt cacttgtttc ttgtccggct caccggtcaa    4740
agctaaagag gagcaaaagg aacggataga atcgggtgcc gctgatctat acggtatagt    4800
gcccttatca cgttgactca acccatgcta tttaactcaa cccctccttc tgaaccccac    4860
catcttcttc cttttcctct catcccacac aattctctat ctcagatttg aattccaaaa    4920
gtcctcggac gaaactgaac aagtcttcct cccttcgata aacctttggt gattggaata    4980
actgaccatc ttctatagtt cccaaaccaa ccgacaatgt aaatacactc ctcgattagc    5040
cctctagagg gcatacgatg gaagtcatgg aatactttttg gctggactct cacaatgatc    5100
aaggtatctt aggtaacgtc tttggcgtgg gccggtgttc gttcccagtc atcgatgcat    5160
tcacatgccc tccctaagct gggccctaga ctctaggatc ctagtctaga aggacatggc    5220
atcgatggac tgggttcgtt ctgagattat acggctaaaa cttgatctgg ataataccag    5280
```

```
cgaaaagggt catgccttct ctcgttcttc ctgttgatgg aatggctaac agatgatagt    5340
cattgcaact tgaaacatgt ctcctccagc tgccatctac gaacccactg tggccgctac    5400
cggcctcaag ggtaaggtcg tggtttctga accgtcccc gttgagggag cttctcagac     5460
caagctgttg gaccatttcg gtggcaagtg ggacgagttc aagttcgccc ctatccgcga    5520
aagccaggtc tctcgtgcca tgaccagacg ttactttgag gacctggaca agtacgctga    5580
aagtgacgtt gtcattgttg gtgctggttc ctgcggtctg agcactgcgt acgtcttggc    5640
caaggctcgt ccggacctga agattgctat cgtcgaggcc agcgtctctc ctggtcagta    5700
gtccatgatg gattgccttg cactcagctt tccggaacta acgtgcaata ggtggcggtg    5760
cctggttggg tggccaactc ttttctgcta tggtcatgcg ccgtcccgcg gaagtcttcc    5820
tgaacgagct gggtgttcct tacgaagagg acgcaaaccc caactacgtt gtcgtcaagc    5880
acgcctccct gtttacctcg acactcatgt cgaaggttct ctccttcccc aatgtcaagc    5940
tcttcaatgc taccgctgtt gaggacttga tcacccgtcc gaccgagaac ggcaaccccc    6000
agattgctgg tgttgtcgtc aactggacgc tggtcaccct tcaccacgat gatcactcct    6060
gcatggaccc caacactatc aacgctcctg tcatcatcag taccactggt cacgatgggc    6120
cattcggcgc cttctgtgcg aagcgcttgg tgtccatggg cagcgtcgac aagctaggtg    6180
gcatgcgtgg tctcgacatg aactcggccg aggatgccat cgtcaagaac acccgcgagg    6240
ttactaaggg cttgataatc ggcggtatgg agctgtctga aattgatggc tttaaccgca    6300
tgggccctac cttcggtgcc atggttctca gtggtgtcaa ggctgccgag gaggcattga    6360
aggtgttcga cgagcgtcag cgcgagtgtg ctgagtaaat gactcactac ccgaatgggt    6420
tcagtgcatg aaccggattt gtcttacggt cttttgacgat aggggaatga tgattatgtg    6480
atagttctga gatttgaatg aactcgttag ctcgtaatcc acatgcatat gtaaatggct    6540
gtgtcccgta tgtaacggtg gggcattcta gaataattat gtgtaacaag aaagacagta    6600
taatacaaac aaagatgcaa gagcggctcg tcatcgcaga taagcactgc tgtcttgcat    6660
ccaagtcagc gtcagcagaa atacgggact tccgaaagta tatggcaaaa ttaaagaact    6720
tgactctcca gcaatgtttt gccctgaccg tcgctaaaac gttactaccc ctatacccgt    6780
ctgtttgtcc cagcccgagg cattaggtct gactgacagc acggcgccat gcgggcttgg    6840
gacgccatgt ccgtcgcgtg ataagggttg atccatgcag ctactatcct tccatcgttc    6900
cattcccatc cttgtcctat ctccatcctt gaaactttac tagtttagtt ggatgctcga    6960
gcttgctctc ggctactccg tccaatggat aagaccccga tgccggtcct cattggtctc    7020
cagctggtat cgccccaacc ttcgtgtgat cgcctctctg cttcccctca tcatcattac    7080
taactagtac atccaaaagc catcccagtg cttcccctca cccttgccca agacattcca    7140
agtgggcctt cggctggaaa acatggaccc attggttcca tcgataagct agctcctcgt    7200
ccgttacccc agattgatac cagataacat tgaccagcgg cttatcaccg aggtctgcgg    7260
gtgagacccc ccctgcgaca agttagataa aagaaactcg cctcattgtg cttccgatgg    7320
ggtcggatga cgagccttcg gaaagagctg gcgcctcttt aaaggggaca gctgtcgcca    7380
agttgtgaaa ttctccgata actactaaca atctctccct tccttcccgc tactgtggtc    7440
accaaatcaa ctctctttc tcggccaaga tctaacatgg cggatgagaa gactgaaaag    7500
tctcccccac cgatgacggt ggatgaggag actggcacaa cagaggaaat tgacccgaca    7560
atggcaaagc atacgaagga tgcagacgag gcactggcgg tcttcgaaga cctccatggt    7620
gaagtcatca cacttgatga ggagacaaac aaaaggatac ttcggacaat tgactggcac    7680
```

```
agtttaaac                                                      7689

<210> SEQ ID NO 58
<211> LENGTH: 1270
<212> TYPE: DNA
<213> ORGANISM: Aspergillus niger
<220> FEATURE:
<221> NAME/KEY: CDS
<222> LOCATION: (1)..(230)
<220> FEATURE:
<221> NAME/KEY: Intron
<222> LOCATION: (231)..(372)
<220> FEATURE:
<221> NAME/KEY: CDS
<222> LOCATION: (373)..(1267)

<400> SEQUENCE: 58 atg ttt gaa atc agc cga ctt ttg cat cag cca att act atg gct tcg    48
Met Phe Glu Ile Ser Arg Leu Leu His Gln Pro Ile Thr Met Ala Ser
1               5                   10                  15 ccg aat cgc aat aac tac agc tac caa ggg ata gaa tcc tat gat tcc    96
Pro Asn Arg Asn Asn Tyr Ser Tyr Gln Gly Ile Glu Ser Tyr Asp Ser
            20                  25                  30 ggc cgt tcc agg caa aac tcg gat gct atg gac att cac gtc att acg   144
Gly Arg Ser Arg Gln Asn Ser Asp Ala Met Asp Ile His Val Ile Thr
        35                  40                  45 gcc caa gaa cct cct cga gaa ccc ccg gac aac aac gat cct tat gat   192
Ala Gln Glu Pro Pro Arg Glu Pro Pro Asp Asn Asn Asp Pro Tyr Asp
    50                  55                  60 ggc cat ggg ggt cca gct ggg act agc cat tat agc aa  gtacttctcc    240
Gly His Gly Gly Pro Ala Gly Thr Ser His Tyr Ser Lys
65                  70                  75 cttctcatac tctgcacccc acgtaccccg caaaatccct ttttctcatg ccgtgcaaat   300
atcacactta tttctacaac taccgggcga ctaattcagg gaactttctt ttccgttgtt   360
cgtttaatct ag g cct cca aac aga tgg ctc ttc tat gaa gaa aat ggg    409
             Pro Pro Asn Arg Trp Leu Phe Tyr Glu Glu Asn Gly
                        80                  85 cga aca tat cat gga tat cgc aga gga gtt tac ccg ctg cca tgc gat   457
Arg Thr Tyr His Gly Tyr Arg Arg Gly Val Tyr Pro Leu Pro Cys Asp
90                  95                  100                 105 gaa cag gaa cag gac cgt ctc gat atc ttc cat aaa ctg ttc aca gta   505
Glu Gln Glu Gln Asp Arg Leu Asp Ile Phe His Lys Leu Phe Thr Val
                110                 115                 120 gca cgg atg tcc gag agc tta atc tac gca cct cac ccc cca aat ggt   553
Ala Arg Met Ser Glu Ser Leu Ile Tyr Ala Pro His Pro Pro Asn Gly
            125                 130                 135 cga ttc cta gat ctg ggg tgc ggc act ggg atc tgg gcc att gat gta   601
Arg Phe Leu Asp Leu Gly Cys Gly Thr Gly Ile Trp Ala Ile Asp Val
        140                 145                 150 gcc cac aag tat ccc aat gct ttc gtt gct gga gta gat cta gca cct   649
Ala His Lys Tyr Pro Asn Ala Phe Val Ala Gly Val Asp Leu Ala Pro
    155                 160                 165 ata cag cct ccc aac cac ccc gat aac tgc gag ttc tat gca cct ttt   697
Ile Gln Pro Pro Asn His Pro Asp Asn Cys Glu Phe Tyr Ala Pro Phe
170                 175                 180                 185 gac ttt gag gcg cca tgg acg ctt ggg gaa aat tct tgg gat ctc att   745
Asp Phe Glu Ala Pro Trp Thr Leu Gly Glu Asn Ser Trp Asp Leu Ile
                190                 195                 200 cat cta cag atg ggt tgc ggc agt gtt ctg ggc tgg cag aat ctc tac   793
His Leu Gln Met Gly Cys Gly Ser Val Leu Gly Trp Gln Asn Leu Tyr
            205                 210                 215
```

```
aag cga atc tta agg cat ctt cag cct ggg gca tgg ttt gaa cag gtg       841
Lys Arg Ile Leu Arg His Leu Gln Pro Gly Ala Trp Phe Glu Gln Val
        220                 225                 230 gaa ata gat ttc gaa ccc cgc tgc gat gat cgc tcc ctg aat gga ctg       889
Glu Ile Asp Phe Glu Pro Arg Cys Asp Asp Arg Ser Leu Asn Gly Leu
235                 240                 245 gca ctc cgg gag tgg tac cag tac ctg aag cag gcg aca caa gat aca       937
Ala Leu Arg Glu Trp Tyr Gln Tyr Leu Lys Gln Ala Thr Gln Asp Thr
250                 255                 260                 265 atg cga ccc ata gcg cac agc tcg cgg gat acc atc aga cac ctt gag       985
Met Arg Pro Ile Ala His Ser Ser Arg Asp Thr Ile Arg His Leu Glu
        270                 275                 280 gag gca ggc ttt acc cag atc gac cat cag atg gtg ggg ctg cct ctc      1033
Glu Ala Gly Phe Thr Gln Ile Asp His Gln Met Val Gly Leu Pro Leu
285                 290                 295 aac cct tgg cac cgt gat gaa cat gag cag aag gta gcc cgt tgg tat      1081
Asn Pro Trp His Arg Asp Glu His Glu Gln Lys Val Ala Arg Trp Tyr
        300                 305                 310 aac ctc gca atc tct gag agt atc gag acg ctc agc ctc gcc cct ttc      1129
Asn Leu Ala Ile Ser Glu Ser Ile Glu Thr Leu Ser Leu Ala Pro Phe
315                 320                 325 agt cgc atc ttt cac tgg gat ctg gat agg atc aga cag atc aca gcg      1177
Ser Arg Ile Phe His Trp Asp Leu Asp Arg Ile Arg Gln Ile Thr Ala
330                 335                 340                 345 gag gtc aag tca caa gcc ttc aac aag gaa atc cac gct tac aat atc      1225
Glu Val Lys Ser Gln Ala Phe Asn Lys Glu Ile His Ala Tyr Asn Ile
        350                 355                 360 tta cat ata tac cag gca cgg aag ccg ggc ggc cca tca ctt tga          1270
Leu His Ile Tyr Gln Ala Arg Lys Pro Gly Gly Pro Ser Leu
        365                 370                 375
```

<210> SEQ ID NO 59
<211> LENGTH: 375
<212> TYPE: PRT
<213> ORGANISM: Aspergillus niger

<400> SEQUENCE: 59

```
Met Phe Glu Ile Ser Arg Leu Leu His Gln Pro Ile Thr Met Ala Ser
1               5                   10                  15

Pro Asn Arg Asn Asn Tyr Ser Tyr Gln Gly Ile Glu Ser Tyr Asp Ser
                20                  25                  30

Gly Arg Ser Arg Gln Asn Ser Asp Ala Met Asp Ile His Val Ile Thr
            35                  40                  45

Ala Gln Glu Pro Pro Arg Glu Pro Pro Asp Asn Asn Asp Pro Tyr Asp
        50                  55                  60

Gly His Gly Pro Ala Gly Thr Ser His Tyr Ser Lys Pro Asn
65                  70                  75                  80

Arg Trp Leu Phe Tyr Glu Glu Asn Gly Arg Thr Tyr His Gly Tyr Arg
                85                  90                  95

Arg Gly Val Tyr Pro Leu Pro Cys Asp Glu Gln Glu Gln Asp Arg Leu
            100                 105                 110

Asp Ile Phe His Lys Leu Phe Thr Val Ala Arg Met Ser Glu Ser Leu
        115                 120                 125

Ile Tyr Ala Pro His Pro Pro Asn Gly Arg Phe Leu Asp Leu Gly Cys
    130                 135                 140

Gly Thr Gly Ile Trp Ala Ile Asp Val Ala His Lys Tyr Pro Asn Ala
145                 150                 155                 160
```

```
Phe Val Ala Gly Val Asp Leu Ala Pro Ile Gln Pro Pro Asn His Pro
            165                 170                 175

Asp Asn Cys Glu Phe Tyr Ala Pro Phe Asp Phe Glu Ala Pro Trp Thr
        180                 185                 190

Leu Gly Glu Asn Ser Trp Asp Leu Ile His Leu Gln Met Gly Cys Gly
    195                 200                 205

Ser Val Leu Gly Trp Gln Asn Leu Tyr Lys Arg Ile Leu Arg His Leu
210                 215                 220

Gln Pro Gly Ala Trp Phe Glu Gln Val Glu Ile Asp Phe Glu Pro Arg
225                 230                 235                 240

Cys Asp Asp Arg Ser Leu Asn Gly Leu Ala Leu Arg Glu Trp Tyr Gln
                245                 250                 255

Tyr Leu Lys Gln Ala Thr Gln Asp Thr Met Arg Pro Ile Ala His Ser
            260                 265                 270

Ser Arg Asp Thr Ile Arg His Leu Glu Glu Ala Gly Phe Thr Gln Ile
        275                 280                 285

Asp His Gln Met Val Gly Leu Pro Leu Asn Pro Trp His Arg Asp Glu
    290                 295                 300

His Glu Gln Lys Val Ala Arg Trp Tyr Asn Leu Ala Ile Ser Glu Ser
305                 310                 315                 320

Ile Glu Thr Leu Ser Leu Ala Pro Phe Ser Arg Ile Phe His Trp Asp
                325                 330                 335

Leu Asp Arg Ile Arg Gln Ile Thr Ala Glu Val Lys Ser Gln Ala Phe
            340                 345                 350

Asn Lys Glu Ile His Ala Tyr Asn Ile Leu His Ile Tyr Gln Ala Arg
        355                 360                 365

Lys Pro Gly Gly Pro Ser Leu
    370                 375

<210> SEQ ID NO 60
<211> LENGTH: 6411
<212> TYPE: DNA
<213> ORGANISM: Artificial Sequence
<220> FEATURE:
<223> OTHER INFORMATION: transgene to complement alg3delta mutant

<400> SEQUENCE: 60
gtttaaacat gcatcattct cccgctttgt ttttgggccc aaactaaccg agtaggtgtg      60
gcatttgcgg gcatgatgtt tcaactaccg ctgatcatta tcaccgcccc attagagaag     120
atccaagacc ctactgggaa ggtgataggc aattccattt tctgggttag tttttgtctt     180
gtcggccagc ctttgggagc tttgctgtac ttctttgcct ggcaagcgaa gtatggcagt     240
gtgagccgaa tgtgaatgta aaagcacgca cgtgtccgct gtttgtcata gatgtaaata     300
aatgccaaca acttcagcca ttttttgaaa agcaaagcaa ccgaagtaaa cgatcctgta     360
ccatcagcgc tcctcacaat ggaatctttt agatgtttct gttccattca tcttgcttac     420
tgcaatgttc ttttcgcgtt tgactaattc tccggatgtt gaatggcaac gctgtcggcg     480
tcgggtcttc agggatccgc caaggatgct ctggatccgc atccggccgc tcttgcgccc     540
catcaatcgc ccgactataa atcgaactac tttcggcatc ttctagactt cctaataccg     600
cctagtcata gcagattcaa gctgagaaca ccacaagtaa atatcaccca tcatgcttac     660
cctgaccgtc cctgaaaact acgggtatgt gccaattcta caattccttg cagacaatgc     720
cattctcccc atgaagtctg atgctaacta tcctgcagct ctgtcattgc cgtcgctctg     780
ggtgccatcc ccgtcctgag cttcgtccat ggcgccgtcg tgtctcgtct ccgcaaggaa     840
```

```
gctgattgcc cctaccctca ctgctatgcg accgtagagc agtgcaagac caacgtaagc    900
caacctcaca caaacaggat tcctcgagct aacatacatt ccgaaccgtg cagcccaagg    960
ccgagcagtt caactgcgct cagcgcgctc atgccaactt ccttgagaac tccagccaaa   1020
ctatgctctt cctcctggta gctggactga agtaccccca gttggcgact ggcctcggaa   1080
gcatctgggt cctcggtcgc tcactgttcc tttacggata tgtgtactcc ggcaagccgc   1140
ggggtcgcgg tcgtttgtac ggcagcttct acttgcttgc acaggagct ctctggggct    1200 tgacgtcttt tggagttgcg agggagttga tttcctactt ctaagtttgg actgaatccg   1260
tggtgtgatt gaggtgattg gcgatgtcgt gaccggtgac tctttctggc atgcggagag   1320
acggacggac gcagagagaa gggctgagta ataagccact ggccagacag ctctggcggc   1380
tctgaggtgc agtggatgat tattaatccg ggaccggccg cccctccgcc ccgaagtgga   1440
aaggctggtg tgcccctcgt tgaccaagaa tctattgcat catcggagaa tatggagctt   1500
catcgaatca ccggcagtaa gcgaaggaga atgtgaagcc aggggtgtat agccgtcggc   1560
gaaatagcat gccattaacc taggtacaga agtccaattg cttccgatct ggtaaaagat   1620
tcacgagata gtaccttctc cgaagtaggt agagcgagta cccggcgcgt aagctcccta   1680
attggcccat ccggcatctg tagggcgtcc aaatatcgtg cctctcctgc tttgcccggt   1740
gtatgaaacc ggaaaggccg ctcaggagct ggccagcggc gcagaccggg aacacaagct   1800
ggcagtcgac ccatccggtg ctctgcactc gacctgctga ggtccctcag tccctggtag   1860 gcagcttttgc cccgtctgtc cgcccggtgt gtcggcgggg ttgacaaggt cgttgcgtca   1920
gtccaacatt tgttgccata ttttcctgct ctccccacca gctgctcttt tcttttctct   1980
ttcttttccc atcttcagta tattcatctt cccatccaag aacctttatt tcccctaagt   2040
aagtactttg ctacatccat actccatcct tcccatccct tattcctttg aacctttcag   2100
ttcgagcttt cccacttcat cgcagcttga ctaacagcta ccccgcttga gcagacatca   2160
ccatggccaa gttgaccagt gccgttccgg tgctcaccgc gcgcgacgtc gccggagcgg   2220
tcgagttctg gaccgaccgg ctcgggttct cccgggactt cgtggaggac gacttcgccg   2280
gtgtggtccg ggacgacgtg accctgttca tcagcgcggt ccaggaccag gtggtgccgg   2340
acaacaccct ggcctgggtg tgggtgcgcg gcctggacga gctgtacgcc gagtggtcgg   2400
aggtcgtgtc cacgaacttc cgggacgcct ccgggccggc catgaccgag atcggcgagc   2460
agccgtgggg gcgggagttc gccctgcgcg accggccgg caactgcgtg cacttcgtgg   2520
ccgaggagca ggactgaccg acgccgacca acaccgccgg tccgacggcg cccacgggt    2580 cccaggagct tgagatccag gagcaggact gaccgacgcc gaccaacacc gccggtccga   2640
cgcggcccga cgggtccgag gcctcggaga tccgtcccc ttttcctttg tcgatatcat    2700
gtaattagtt atgtcacgct tacattcacg ccctccccc acatccgctc taaccgaaaa    2760
ggaaggagtt agacaacctg aagtctaggt ccctatttat ttttttatag ttatgttagt   2820
attaagaacg ttatttatat ttcaaatttt tcttttttt ctgtacagac gcgtgtacgc    2880
atgtaacatt atactgaaaa ccttgcttga gaaggttttg ggacgctcga agccgatgaa   2940
gaggtgtcta cgttcctaca attggaagaa gaagcacaga gattggccaa ggcaggccac   3000
gagtgtcctg ttcccaagcc tcgagggatt ctgggcgaat tgctgggttt tacgagtagt   3060
ggaggtattt cgacatcaac gacgacacag gcacaacagg ttggagaggg tcggtaaccg   3120
acaattggaa agcaaggagg actcaatcaa ggctaaaata ggctttgagc atgtacagcg   3180
```

```
tgaaggaact gtggattata tcacgaaata agccatgagg cagtcgtgtt ggcttcgacg    3240
gaggttggct tcggaaattt tcggccgggc accaaatccg acccatggca gcaatatacc    3300
catctttgta tcgatagtgt acttacaaaa actgtctact atatgattat gcatatgcga    3360
ttaaatacaa ctctcaattg atgcacaatt cgcctcaact tctatggtaa cgaacccacc    3420
tgttctgcag acatgcggcc gcgcggtctg tgtgtgtcca tgaacgctaa tcccaaacgg    3480
gacagctctc attggctctc cggcacgaag aggccacccg acatctacag ctgtagaaga    3540
aagtagctgg ttcaacaacc gcatgcaaga tggactggat gcgcctaatt cgcgatttgt    3600
gtttcaatcc ccgacacaca aaatggatgg ctccgctcct ggtcctgggt gacgcttttcc   3660 tctgcgcgct gatcatctgg aaagtgccct gtaaggctac agctaagctc cgttcacacc    3720
cttttgcgac aagtgaagca atgccactaa cctagccccg ttgctattgt ccacagatac    3780
cgagattgac tgggccacgt acatgcaaca aatatcgctt tatttgtcag gagaacgcga    3840
ttatactctc atcagaggat caaccggtcc ccttgtctac ccggccgccc atgtatacag    3900
ttatacggcc ctctaccatc tcaccgatga ggggcgcgat attttcttcg gtcagatact    3960
atttgctgtg ctctacttga tcacgctggt ggttgtgctg tgctgttata gacagtcggg    4020
tgctccgccg tacttgcttc cgctgctggt cctttccaag agacttcaca gcgtttatgt    4080
cctgcgtctg ttcaatgatg gcttggcggc gctggcgatg tgggttgcca ttctgttatt    4140
catgaatcgg aagtggacgg ctgccggtcgc agtgtggtct actggtgttg cgattaagat    4200
gacactgttg ctgctggccc cggctattgc tgtggtcacg gtgcttagtc tgtcgcttgg    4260
tcctagcgtg gggctggggg ttctggcggt gcttgtccag gtaggttccc atgaggctgt    4320
agggttggcc aaaggcaatt tgtgtgaaga cttgtctgac attgaactac aggttttact    4380
cgcgataccg ttcctacaaa acaacccggc ggggtatctc tcgcgggcgt tcgagctaac    4440
cagacagttc atgtttaaat ggacagtcaa ttggagattt gttggcgaag aagtattctt    4500
atctaagagc ttttcccctgg cattgctggc cgtccacatt gtgctgctag gcgcttttgc    4560
cgtcactggt tggctgagat actccaggtc tagcttgcct gcgttcattc ggaatctgct    4620
agcgggtcga catcgcacag tgtccctccc caaaccctac atcatgagcg tgatgctctc    4680
gtctctgaca gttggcttgt tgtgcgcaag gtccccttcat taccaattct tcgcctacct    4740
ctcctgggcg acaccttcc tcctctggcg cgcagggttt catccaatct tgctgtacct    4800
tatctgggct atgcaagagt gggcttggaa cacattcccc agcaccaacc tcagttccat    4860
cattgttgtc ctctcacttg ctacccgag tttcggcgtc cttgcgaata gtgccagcgc    4920
cttttatacc atgcgttcga accctagcgg taaagagcat aaccaataga agtgacaccc    4980
ggccagtatc gagatcgggc tgtgacaggt gcatcgataa tcgcaatcag tcttgtaccc    5040
atgagaatcc ctgaaaaagt aagactgctc tgtcaggtag tccattgccc atgcgatagg    5100
ttcggacgcc taaaggatca atcaagatgc caatcaagca tccgactcat cggaagaagg    5160
catcttgccg acattggact catcctcttc gtccgagtcg tcggcgacaa cagcagcttg    5220
cttagcgatg gtgtggcaca aggatcaatg cggtacgacg atttgatgca gataagcagg    5280
ctgcgaagta gtaactcttg cgtagagaaa atggcgacgg gtggctgata agggcggtga    5340
taagcttaat tgtcatcgca gataagcact gctgtcttgc atccaagtca gcgtcagcag    5400
aaatacggga cttccgaaag tatatggcaa aattaaagaa cttgactctc cagcaatgtt    5460
ttgccctgac cgtcgctaaa acgttactac ccctatccc gtctgtttgt cccagcccga    5520
ggcattaggt ctgactgaca gcacggcgcc atgcgggctt gggacgccat gtccgtcgcg    5580
```

```
tgataagggt tgatccatgc agctactatc cttccatcgt tccattccca tccttgtcct    5640
atctccatcc ttgaaacttt actagtttag ttggatgctc gagcttgctc tcggctactc    5700
cgtccaatgg ataagacccc gatgccggtc ctcattggtc tccagctggt atcgcccccaa   5760 ccttcgtgtg atcgcctctc tgcttcccct catcatcatt actaactagt acatccaaaa    5820
gccatcccag tgcttcccct caccccttgcc caagacattc caagtgggcc ttcggctgga   5880
aaacatggac ccattggttc catcgataag ctagctcctc gtccgttacc ccagattgat    5940
accagataac attgaccagc ggcttatcac cgaggtctgc gggtgagacc cccctgcga    6000 caagttagat aaaagaaact cgcctcattg tgcttccgat ggggtcggat gacgagcctt    6060
cggaaagagc tggcgcctct ttaaagggga cagctgtcgc caagttgtga aattctccga    6120
taactactaa caatctctcc cttccttccc gctactgtgg tcaccaaatc aactctcttt    6180
tctcggccaa gatctaacat ggcggatgag aagactgaaa agtctccccc accgatgacg    6240
gtggatgagg agactggcac aacagaggaa attgacccga caatggcaaa gcatacgaag    6300
gatgcagacg aggcactggc ggtcttcgaa gacctccatg gtgaagtcat cacacttgat    6360
gaggagacaa acaaaaggat acttcggaca attgactggc acagtttaaa c             6411
```

ENHANCED CITRIC ACID PRODUCTION IN ASPERGILLUS WITH INACTIVATED ASPARAGINE-LINKED GLYCOSYLATION PROTEIN 3 (ALG3), AND/OR INCREASED LAEA EXPRESSION

CROSS-REFERENCE TO RELATED APPLICATION

This application claims priority to U.S. Provisional Application No. 61/565,018 filed Nov. 30, 2011, herein incorporated by reference.

FIELD

This application provides recombinant *Aspergillus* fungi that are genetically inactivated for the dolichyl-P-Man:Man (5)GlcNAc(2)-PP-dolichyl mannosyltransferase (Alg3) gene, are genetically enhanced to increase the expression levels of the loss of aflR expression A (LaeA) gene, or both, which results in substantial improvement of citric acid production. Methods of using these fungi to produce citric acid are also provided.

BACKGROUND

Filamentous fungi, such as *Aspergillus niger*, are well known for their industrial applications in protein and chemical productions. They are used to produce a wide variety of products ranging from human therapeutics, glycosyl hydrolases to specialty chemicals [Punt et al., *Trends Biotechnol* 20(5):200-206, 2002; Schuster et al., *Appl Microbiol Biotechnol* 59(4-5):426-435, 2002; Gerngross, *Nat Biotechnol* 22(11):1409-1414, 2004; Nevalainen et al., *Trends Biotechnol* 23(9):468-474, 2005; Sauer et al., *Trends Biotechnol.* 26(2):100-8, 2008; Magnuson and Lasure (2004). "Organic acid production by filamentous fungi." *Advances in fungal biotechnology for industry, agriculture, and medicine*, pages 307-340]. Some of industrial *A. niger* strains are capable of growing on solutions of glucose or sucrose in excess of 20% (w/v) and converting approximately 90% of the supplied carbohydrate to citric acid. These remarkable properties are the reason that *A. niger* has been used to produce citric acid for more 80 years and is currently the primary source of commercial citric acid production (Magnuson and Lasure (2004). "Organic acid production by filamentous fungi." *Advances in fungal biotechnology for industry, agriculture, and medicine*, pages 307-340).

The maximum product output in fermentation processes is the result of optimal metabolic pathways and cellular formation, which are influenced by endogenous and exogenous factors. Cellular metabolisms are tightly controlled and highly interconnected, and are regulated spatially and temporally at different levels, such as transcription, post-transcription, translation, and post-translation. Therefore, different approaches have been explored to understand the regulatory mechanisms of metabolic processes and cellular formation for maximizing the product output in filamentous fungi. For example, comparative genomics was used to examine citric-acid-producing versus enzyme-producing *A. niger* strains (Andersen et al., *Genome Res.* 21(6): 885-97, 2011), proteomics was used to examine filamentous fungi related to enzymes or organic acid production (de Oliveira and de Graaff, *Appl. Microbiol. Biotechnol.* 89(2): 225-37, 2011), or combination of both genomics and proteomics were used to examine enzyme production (Jacobs et al., *Fungal Genetics and Biology* 46(1, Supplement):S141-S152, 2009). Although these studies examined the potential involvement of selected genes and proteins in optimizing production of organic acids or proteins in filamentous fungi, methods for altering the complex post-translation modifications (such as N-glycosylation of cellular proteins) for signal transduction, cellular formation and metabolism at different growth and development stages, which may affect product output, have not been examined.

Protein glycosylation is a ubiquitous and structurally diverse form of post translation modification, which occurs at all domains of life. More than two-thirds of eukaryotic proteins are predicted to be glycosylated (Apweiler et al., *Biochim Biophys Acta* 1473(1):4-8, 1999). N- and O-linked protein glycosylation are common types of protein glycosylation, occurring mainly on the asparagine (N) and serine/threonine (S/T) residues, respectively. N-linked glycosylation has been implicated in many biochemical and cellular processes, including protein secretion, stability and translocation, maintenance of cell structure, receptor-ligand interactions and cell signaling, cell-cell recognition, pathogen infection, and host defense in various organisms (Haltiwanger and Lowe, *Ann. Rev. Biochem.* 73(1):491-537, 2004; Dellaporta et al., *Plant Mol. Biol. Reporter* 1(4):19-21, 1983; Nam et al., *Biotech. Bioengineer.* 100(6):1178-1192, 2008; Trombetta and Parodi, *Ann. Rev. Cell Dev. Biol.* 19(1):649-676, 2003; Tsang et al., *Fungal Genetics and Biology* 46(1): S153-S160, 2009; Pang et al., *Science,* 333(6050):1761-4, 2011).

N-glycosylation is highly complex and has been extensively studied in mammalian systems (Yan and Lennarz, *J. Biol. Chem.* 280(5):3121, 2005; Silberstein and Gilmore, *FASEB J.* 10(8): 849, 1996; Kornfeld and Kornfeld, *Annu. Rev. Biochem.* 54:631-664, 2005; Kim et al., *PLoS ONE* 4(10): e7317, 2009, 2009) and yeast (Kukuruzinska et al., *Annu. Rev. Biochem.* 56(1):915-944, 1987). The protein N-glycosylation pathways in filamentous fungi have also been identified (Deshpande et al., *Glycobiology* 18(8):626-637, 2008; Geysens et al., *Fungal Genetics and Biology* 46(1, Supplement): S121-S140, 2009) on the basis of the known genomic sequences. Several genes involved in N-glycosylation have been studied in filamentous fungi (Kotz et al., *PLoS ONE* 5(12):e15729, 2010; Kainz et al., *Appl Environ Microbiol* 74(4):1076-86, 2008; Maras et al., *J. Biotechnol.* 77(2-3):255-63, 2000; Maddi and Free, *Eukaryot Cell* 9(11):1766-75, 2010; Bowman et al., *Eukaryotic Cell* 5(3):587-600, 2006). In these studies, the effects of gene deletion on N-linked glycan patterns formation, the cell wall formation, overall protein secretion and/or the phenotypic changes were demonstrated.

Alg3 is localized in the ER and catalyzes the initial transfer of a mannose residue from dolichol pyrophosphate-mannose to lipid-linked Man5GlcNAc2-PP-Dol on the ER luminal side. It is involved in the early N-glycan synthesis in eukaryotes for the assembly of a Glc3Man9GlcNAc2 core oligosaccharide that is linked to the lipid carrier dolichol pyrophosphate. The Alg3 gene and its functions have been identified and studied in *S. cerevisiae, P. pastories, T. brucei, A. thaliana,* and human (Aebi et al., *Glycobiol.* 6(4):439-444, 1996; Korner et al., *EMBO J.* 18(23): 6816-6822, 1999; Davidson et al., *Glycobiology* 14(5):399-407, 2004; Manthri et al., *Glycobiol.* 18(5):367-83, 2008; Kajiura et al., *Glycobiol.* 20(6):736-51, 2010). In these studies, the Alg3 mutants exhibited a unique structural profile in the glycoproteins, such as Man3GlcNAc2, Man4GlcNAc2, Man5GlcNAc2, GlcMan5GlcNAc2, and Glc3Man5GlcNAc2, which affected the overall N-glycosylation by incomplete utilization of N-linked glycosites in glycoproteins. No obvious growth phenotype was observed in those Alg3Δ mutants of *S. cerevisiae*, *P. pastoris*, *T. brucei*, and plant except that the Alg3 defect in human caused severe diseases such as profound psychomotor delay, optic atrophy, acquired microcephaly, iris olobomas and hypsarrhythmia (Stibler et al., *Neuropediatrics* 26(5): 235-7, 1995; Sun et al., *J. Clin. Endocrinol. Metab.* 90(7):4371-5, 2005; Schollen et al., *Eur. J. Med. Genet.* 48(2):153-158, 2005, Kranz et al., *Am. J. Med. Genet.* 143A(13):1414-20, 2007; Denecke et al., *Pediatr. Res.* 58(2): 248-53, 2005).

LaeA, a global regulator gene for the secondary metabolism, was first identified in *A. nidulans* through complementing the aflR deficient mutants (Bok and Keller, *Eukaryot Cell* 3:527-535, 2004). Deletion of LaeA gene inhibits the expression of secondary metabolic gene clusters, such as sterigmatocystin, penicillin, and lovastin, but has no effect on spore production in *A. nidulans*. The LaeA that was confirmed as a nuclear protein and a putative methyltransferase does not involve in gene clusters for nutrient utilization (Bok et al., *Mol Microbiol* 61:1636-45, 2006). Furthermore, the role of LaeA in secondary metabolism was confirmed in *Aspergillus flavus* and *Aspergillus oryzae* (Kale et al., *Fungal Genet. Biol.* 45:1422-9, 2008; Oda et al., *Biosci Biotechnol Biochem* 75:1832-4, 2011). Evidence indicates that LaeA reverses gene repression at the level of the heterochromatin state (Reyes-Dominguez et al., *Molecular Microbiology* 76:1376-86, 2010). LaeA is a component of the heterotrimeric VeA/VelB/LaeA protein complex (Bayram et al., *Science Signalling* 320:1504, 2008), which involves in the acetylation signal transduction for secondary metabolite production in *A. nidulans* (Soukup et al., *Mol. Microbiol.*, 86(2):314-30, 2012). The veA/VelB/LaeA complex may coordinately respond to environmental cues (Ramamoorthy et al., *Mol. Microbiol.*, 85(4):795-814, 2012) and has a role in fungal morphology (Calvo, *Fungal Genetics and Biology* 45:1053-61, 2008). LaeA may direct the formation of the VelB-VosA and VelB-VelA-LaeA complexes, control veA modification and protein levels, and be involved in light regulation of growth and development (Bayram et al., *PLoS genetics* 6: e1001226, 2010).

SUMMARY

Although the current commercial conversion rate of carbohydrate to citric acid in *A. niger* is more than eighty to ninety percent, further improvement citric acid and other metabolites is desirable. This disclosure describes the role of the dolichyl-P-Man:Man(5)GlcNAc(2)-PP-dolichyl mannosyltransferase gene (α-1,3-mannosyltransferase, Alg3) on the spore germination, filamentous growth, sporulation, and production of citric acid in *Aspergillus niger*. In addition, the role of the LaeA in citric acid production by its over-expression is shown, for example in combination with an Alg3Δ mutant background.

Based on these observations, provided herein are isolated fungi (such as filamentous fungi) having a gene inactivation (also referred to herein as a gene deletion) of a dolichyl-P-Man:Man(5)GlcNAc(2)-PP-dolichyl mannosyltransferase (Alg3) gene (referred to herein as Alg3Δ strains), a gene enhancement (e.g., overexpression) of a LaeA gene (referred to herein as upregulated LaeA strains), or both. Any strain of fungi can be used, such as a filamentous fungi, for example *Aspergillus niger* (*A. niger*) or particular strains thereof (for example *A. niger* strain 11414 or 11414KusA). In particular examples, an Alg3Δ strain exhibits one or more of the following characteristics: slower growth on citric acid production (CAP) medium, complete medium (CM) or potato dextrose agar (PDA) medium; earlier spore germination and a higher germination rate in CAP medium; delayed spore germination in CM or PDA medium; reduced sporulation on complete medium; or combinations thereof. In some examples, such increases or decreases are relative to *A. niger* strain 11414KusA grown under the same conditions. The combination of Alg3Δ and over-expression of LaeA resulted in some improvement of sporulation on CM.

In particular examples, such Alg3Δ strains, up-regulated LaeA strains, or Alg3Δ-upregulated LaeA strains, produce more citric acid when grown in CAP medium, such as at least 20%, at least 50%, or at least 70% more than *A. niger* strain 11414KusA under identical growing conditions after at least 4 days or at least 10 days. Thus, one strategy to increase citric acid production is to reduce the carbohydrate consumption for protein glycosylation and cellular formation, as altering protein glycosylation can augment the carbohydrate flux into citric acid production in *A. niger*.

Also provided herein are compositions (such as fermentation broth) and kits that include a fungal Alg3Δ strain, up-regulated LaeA strain, or Alg3Δ-upregulated LaeA strain.

Also provided herein are methods of making citric acid using the disclosed fungal Alg3Δ strains, up-regulated LaeA strains, and Alg3Δ-upregulated LaeA strains. For example, such a method can include culturing an isolated Alg3Δ fungus, up-regulated LaeA fungus, or Alg3Δ-upregulated LaeA fungus, under conditions that permit the fungus to make citric acid, thereby making citric acid. For example, the Alg3Δ fungus, up-regulated LaeA fungus, or Alg3Δ-upregulated LaeA fungus, can be cultured in CAP medium. In some examples, the method further includes isolating the citric acid produced.

The foregoing and other objects and features of the disclosure will become more apparent from the following detailed description, which proceeds with reference to the accompanying figures.

BRIEF DESCRIPTION OF THE DRAWINGS

FIGS. 6A-E show spore germination of parent 11414kusA and Alg3Δ strains in citric acid production (CAP) liquid medium. (A and B) Inverted microscopic images for parent 11414kusA strain. (C and D) Inverted microscopic images for Alg3Δ strain. (A and C) Strains grown in CAP liquid culture at 30° C. for 8 hrs. (B and D) Strains grown in CAP liquid culture at 30° C. for 15 hrs. (E) Time course of the spore germination rate (%) of parent and Alg3Δ strains grown in CAP liquid culture. The solid cycle for parent 11414kusA strain and open cycle for the Alg3Δ strain.

FIG. 9 shows an alignment of Alg3 nucleic acid sequences from *A. niger* (top strand, nucleotides 1986-2518 of SEQ ID NO: 1) and *A. oryzae* (bottom strand, nucleotides 643-1175 of SEQ ID NO: 3).

FIGS. 10A and 10B show an alignment of Alg3 protein sequences from *A. niger* (SEQ ID NO: 2), *A. nidulans* (SEQ ID NO: 31), *Fusarium oxysporum* (SEQ ID NO: 32), *Neurospora crassa* (SEQ ID NO: 33), *S. cerevisiae* (SEQ ID NO: 34), *Arabidopsis thaliana* (SEQ ID NO: 35), and *Homo sapiens* (SEQ ID NO: 36). The signs at the top of the alignment show: '−' the average weight of column pair exchanges is less than weight matrix mean value; '.' is less than mean value plus one SD; '+' is less than mean value plus two SD; and '*' is more than mean value plus two SD.

FIG. 11 shows an alignment of Alg3 protein sequences from *A. niger* (top strand, amino acids 12-411 of SEQ ID NO: 2) and *S. cerevisiae* (bottom strand, amino acids 31-434 of SEQ ID NO: 34).

FIG. 12 shows an alignment of LaeA protein sequences from *A. nidulans* (top strand, amino acids 14-372 of SEQ ID NO: 41) and *A. niger* (bottom strand, amino acids 14-370 of SEQ ID NO: 59).

FIGS. 15A and 15B show digital images of the results of polymerase chain reaction (PCR) analysis of LaeA gene insertion in the transgenic *A. niger* genome of heterologous expression of *A. nidulans* LaeA gene. (A) PCR products of *A. oryzae* ptrA gene detected in selected single spore colony isolate (SCI) of LaeA gene transgenic mutants and parent kusA and Alg3Δ are control strains. (B) PCR products of transgene expression DNA fragment including the gpdA promoter, LaeA coding region and trpC gene transcriptional terminator. The SCI-1 to SCI-4 is the individual single spore colony of LaeA gene transgenic mutants and parent kusA and Alg3Δ are control strains. Lambda DNA marker is the restriction fragment of BstEII restriction enzyme.

SEQUENCE LISTING

The nucleic acid sequences listed in the accompanying sequence listing are shown using standard letter abbreviations for nucleotide bases, as defined in 37 C.F.R. 1.822. Only one strand of each nucleic acid sequence is shown, but the complementary strand is understood as included by any reference to the displayed strand. In the accompanying sequence listing:

SEQ ID NOS: 1 and 2 are exemplary Alg3 nucleic acid and protein sequences, respectively, from *A. niger*.

SEQ ID NOS: 3 and 4 are exemplary Alg3 nucleic acid and protein sequences, respectively, from *A. oryzae*.

SEQ ID NOS: 5-30 show exemplary primer sequences.

SEQ ID NOS: 31-36 are exemplary Alg3 protein sequences from *A. nidulans, Fusarium oxysporum, Arabidopsis thaliana, Neurospora crassa, S. cerevisiae*, and *Homo sapiens*, respectively.

SEQ ID NO: 37 is an exemplary *Aspergillus nidulans* glyceraldehyde 3-phosphate dehydrogenase (gpdA) promoter sequence.

SEQ ID NOS: 38 and 39 are exemplary forward and reverse primers, respectively, that can be used to isolate or amplify an *A. nidulans* gpdA promoter.

SEQ ID NOS: 40 and 41 are exemplary *Aspergillus nidulans* methyltransferase (LaeA) coding and protein sequences, respectively.

SEQ ID NOS: 42 and 43 are exemplary forward and reverse primers, respectively, that can be used to isolate or amplify an *A. nidulans* LaeA sequence.

Figure 13:
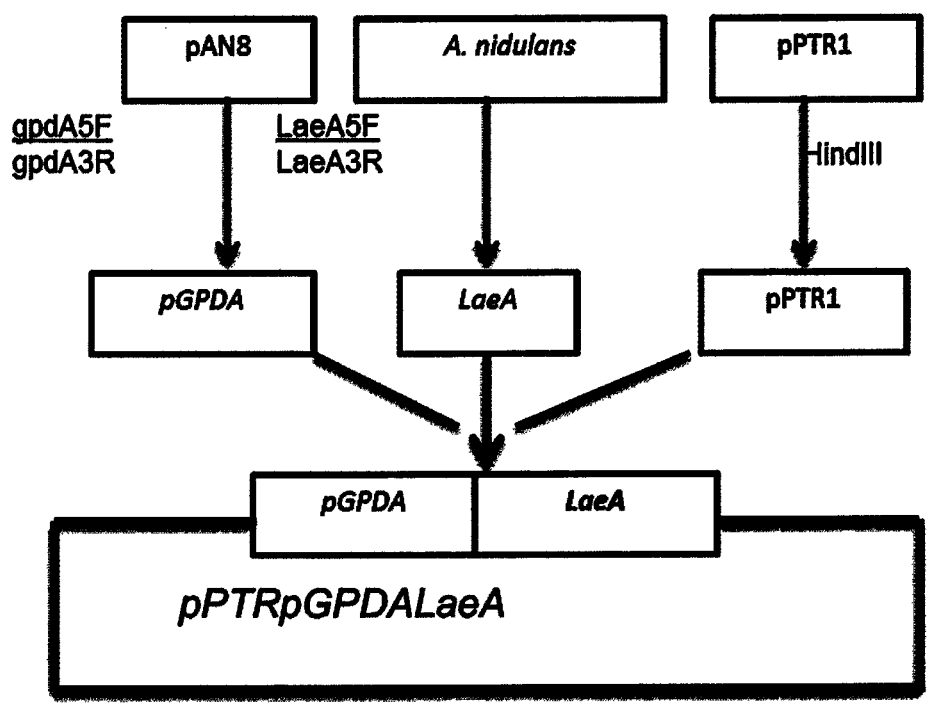
FIG. 13 is a schematic diagram showing the construction of pPTRpGPDALaeA plasmid vector. Both the glyceraldehyde 3-phosphate dehydrogenase (gpdA) promoter and LaeA (loss of aflR expression A) gene coding sequence of genomic DNA were isolated by overlap PCR from pAN7-1 plasmid vector and *A. nidulans* with additions of HindIII restriction enzyme sites at 5'-end of gpdA promoter and 3'-end of LaeA gene, confirmed by DNA sequence, and ligated into pPTR1 plasmid vector at HindIII restriction enzyme site.

SEQ ID NO: 44 is the nucleic acid sequence of the pGPDA-LaeA fragment described in FIG. 13 and Example 5.

SEQ ID NO: 45 is the upstream region of *A. niger* pyrG gene.

SEQ ID NO: 46 is the trpC transcriptional terminator of *A. nidulans*.

SEQ ID NO: 47 is the pyrithiamine resistance gene (ptrA) of *Aspergillus oryzae*.

SEQ ID NO: 48 is the downstream region of *A. niger* pyrG gene.

SEQ ID NOS: 49 and 50 are exemplary forward and reverse primers, respectively, that can be used to isolate or amplify an upstream region of *A. niger* pyrG.

SEQ ID NOS: 51 and 52 are exemplary forward and reverse primers, respectively, that can be used to isolate or amplify the trpC transcriptional terminator of *A. nidulans*.

SEQ ID NOS: 53 and 54 are exemplary forward and reverse primers, respectively, that can be used to isolate or amplify ptrA of *Aspergillus oryzae*.

SEQ ID NOS: 55 and 56 are exemplary forward and reverse primers, respectively, that can be used to isolate or a downstream region of *A. niger* pyrG.

SEQ ID NO: 57 is the nucleic acid sequence of the transgene fragment described in FIG. 13 and Example 6.

SEQ ID NOS: 58 and 59 are exemplary *Aspergillus niger* LaeA coding and protein sequences, respectively.

SEQ ID NO: 60 is the nucleic acid sequence of the transgene fragment used to complement the alg3Δ mutant with the original alg3 gene at pyrG locus.

DETAILED DESCRIPTION

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All references and Genbank Accession numbers mentioned herein are incorporated by reference (the sequence available on Nov. 30, 2011). The materials, methods, and examples are illustrative only and not intended to be limiting.

In order to facilitate review of the various embodiments of the disclosure, the following explanations of specific terms are provided:

Alg3 (dolichyl-P-Man:Man(5)GlcNAc(2)-PP-dolichyl mannosyltransferase):

Also known as asparagine-linked glycosylation 3 and α-1,3-mannosyltransferase. Alg3 encodes an enzyme which catalyzes the addition of the first dol-p-man derived mannose in an α-1,3 linkage to Man5GlcNAc2-PP-Dol. The term Alg3 (or Alg3) includes any Alg3 gene (such as a fungal Alg3 sequence), cDNA, mRNA, or protein, that is an Alg3 involved in catalyzing the addition of the first dol-p-man derived mannose in an α-1,3 linkage to Man5GlcNAc2-PP-Dol, and when genetically inactivated results in a fungus that has an ability to produce more citric acid than the parent strain (such as at least 20%, at least 30%, at least 50%, at least 60%, or at least 70% more than a parent strain under the same growing conditions).

Alg3 sequences are publicly available for many species of *Aspergillus*. For example, GenBank Accession Nos: XM_001823992.2 and XP_001824044 disclose *Aspergillus oryzae* RIB40 Alg3 nucleic acid and protein sequences, respectively; GenBank Accession Nos: XM_001398659.2 and XP_001398696.2 disclose *Aspergillus niger* CBS 513.88 Alg3 nucleic acid and protein sequences, respectively (SEQ ID NOS: 1 and 2); and GenBank Accession Nos: XM_748359.1 and XP_753452 disclose *Aspergillus fumigatus* Af293 Alg3 nucleic acid and protein sequences, respectively. Addition exemplary Alg3 sequences are provided in SEQ ID NOS: 1-4 and 31-36. However, one skilled in the art will appreciate that in some examples, an Alg3 sequence can include variant sequences (such as allelic variants and homologs) that retain Alg3 activity but when genetically inactivated in *Aspergillus* results in a fungus that has an ability to produce more citric acid than the parent strain (such as at least 20%, at least 30%, at least 50%, at least 60%, or at least 70% more under the same growing conditions).

Detectable:

Capable of having an existence or presence ascertained. For example, production of citric acid is detectable if the signal generated is strong enough to be measurable.

Genetic Enhancement or Up-Regulation:

When used in reference to the expression of a nucleic acid molecule, such as a gene, refers to any process which results in an increase in production of a gene product. A gene product can be RNA (such as mRNA, rRNA, tRNA, and structural RNA) or protein. Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene up-regulation can include inhibition of repression as well as stimulation of expression above an existing level. Examples of processes that increase translation include those that increase translational initiation, those that increase translational elongation and those that increase mRNA stability. In one example, additional copies of genes are introduced into a cell in order to increase expression of that gene in the resulting transgenic cell.

Gene up-regulation includes any detectable increase in the production of a gene product. In certain examples, production of a gene product increases by at least 1.5-fold, at least 2-fold, or at least 5-fold), such as LaeA. For example, a genetic enhancement of a LaeA gene in *Aspergillus* (e.g., *A. niger*) results in an *Aspergillus* strain having increased levels of the LaeA protein relative to the parent strain, which can increase the ability of the fungus to produce more citric acid. Genetic enhancement is also referred to herein as "enhancing or increasing expression."

Genetic Inactivation or Down-Regulation:

When used in reference to the expression of a nucleic acid molecule, such as a gene, refers to any process which results in a decrease in production of a gene product. A gene product can be RNA (such as mRNA, rRNA, tRNA, and structural RNA) or protein. Therefore, gene down-regulation or deactivation includes processes that decrease transcription of a gene or translation of mRNA.

For example, a mutation, such as a substitution, partial or complete deletion, insertion, or other variation, can be made to a gene sequence that significantly reduces (and in some cases eliminates) production of the gene product or renders the gene product substantially or completely non-functional. For example, a genetic inactivation of an Alg3 gene in *Aspergillus* (e.g., *A. niger*) results in *Aspergillus* having a non-functional or non-existent Alg3 protein, which results in an ability of the fungus to produce more citric acid. Genetic inactivation is also referred to herein as "functional deletion".

Isolated:

To be significantly separated from other agents. An "isolated" biological component (such as a nucleic acid molecule or protein) has been substantially separated, produced apart from, or purified away from other biological components in the cell of the organism in which the component occurs, for example, other chromosomal and extra-chromosomal DNA and RNA, and proteins. Nucleic acid molecules and proteins which have been "isolated" include nucleic acid molecules and proteins purified by standard purification methods. The term also embraces nucleic acid molecules and proteins prepared by recombinant expression in a host cell as well as chemically synthesized proteins and nucleic acids. Samples of isolated biological components include samples of the biological component wherein the biological component represents greater than 90% (for example, greater than 95%, such as greater than 98%) of the sample.

An "isolated" microorganism (such as an Alg3Δ strain of *Aspergillus*) has been substantially separated or purified away from microorganisms of different types, strains, or species. Microorganisms can be isolated by a variety of techniques, including serial dilution and culturing and resistance to certain chemicals.

LaeA (Loss of aflR Expression A):

LaeA encodes a protein which regulates secondary metabolite production in *Aspergillus*. The term LaeA (or LaeA) includes any LaeA gene (such as a fungal LaeA sequence), cDNA, mRNA, or protein, that is an LaeA involved in secondary metabolite production, and when its expression is increased, for example in combination with a genetically inactivated Alg3 gene, results in a fungus that has an ability to produce more citric acid than the parent strain (such as at least 20%, at least 30%, at least 40%, 50%, at least 60%, or at least 70% more than a parent strain under the same growing conditions).

LaeA sequences are publicly available for many species of *Aspergillus*. For example, GenBank Accession Nos: AB267276 and BAF74528.1 disclose *Aspergillus oryzae* LaeA nucleic acid and protein sequences, respectively; GenBank Accession No. EHA27020.1 discloses an exemplary *Aspergillus niger* ATCC1015 LaeA protein sequence, a parent strain of 11414kusA (other exemplary sequences are provided in SEQ ID NOS: 58 and 59); GenBank Accession No: CBF88745 discloses an *Aspergillus nidulans* LaeA protein sequence; and GenBank Accession Nos: AY422723 and AAR01218 disclose *Aspergillus fumigatus* LaeA nucleic acid and protein sequences, respectively. Additional exemplary LaeA sequences are provided in SEQ ID NOS: 40-41 and 58-59. However, one skilled in the art will appreciate that in some examples, an LaeA sequence can include variant sequences (such as allelic variants and homologs) that retain LaeA activity and when genetically up-regulated in *Aspergillus* (for example in combination with Alg3Δ) results in a fungus that has an ability to produce more citric acid than the parent strain (such as at least 20%, at least 30%, at least 40%, at least 50%, at least 60%, or at least 70% more under the same growing conditions).

Mutation:

A change in a nucleic acid sequence (such as a gene sequence) or amino acid sequence, for example as compared to a nucleic acid or amino acid sequence present in a wild-type or native organism. In particular examples, a mutation is introduced into an Alg3 gene in *Aspergillus*. Mutations can occur spontaneously, or can be introduced, for example using molecular biology methods. In particular examples, a mutation includes one or more nucleotide substitutions, deletions, insertions, or combinations thereof. In particular examples, the presence of one or more mutations in a gene can significantly inactivate that gene.

Recombinant:

A recombinant nucleic acid molecule or protein is one that has a sequence that is not naturally occurring or has a sequence that is made by an artificial combination of two otherwise separated segments of sequence. In particular examples, this artificial combination is accomplished by chemical synthesis or by the artificial manipulation of isolated segments of nucleic acids, for example, by genetic engineering techniques such as those described in Sambrook et al. (ed.), Molecular Cloning: A Laboratory Manual, 3d ed., vol. 1-3, Cold Spring Harbor Laboratory Press, Cold Spring Harbor, N.Y., 2001. The term recombinant includes nucleic acid molecules that have been altered solely by addition, substitution, or deletion of a portion of the nucleic acid molecule.

Sequence Identity/Similarity:

The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2.

To compare two amino acid sequences, the options of Bl2seq can be set as follows: -i is set to a file containing the first amino acid sequence to be compared (e.g., C:\seq1.txt);

-j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least 75%, 80%, 85%, 90%, 95%, or 99% sequence identity.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, 70%, 80%, 90%, 95%, 98%, or 99% sequence identity determined by this method.

One of skill in the art will appreciate that these sequence identity ranges are provided for guidance only; it is possible that strongly significant homologs could be obtained that fall outside the ranges provided.

Transformed:

A cell, such as a fungal cell, into which a nucleic acid molecule has been introduced, for example by molecular biology methods known in the art. As used herein, the term transformation encompasses all techniques by which a nucleic acid molecule might be introduced into such a cell, including, but not limited to transfection with viral vectors, conjugation, transformation with plasmid vectors, and introduction of naked DNA by electroporation, lipofection, and biolistic particle delivery.

Overview

This disclosure provides the first demonstration that genetic inactivation of Alg3, a gene involved in protein N-linked glycosylation, can result in substantial improvement of citric acid production in *A. niger*, while the total biomass is similar to the parent strain. The core oligosaccharide Glc3Man9GlcNAc2 is synthesized by a series of membrane-bound glycosyltransferases, which begins on the cytoplasmic side of the membrane of the endoplasmic reticulum (ER) and flips into the lumenal side of the ER membrane to complete its synthesis. The lipid-linked core Glc3Man9GlcNAc2 is subsequently transferred to a nascent protein in the ER, where the glycoproteins are folded and then shuttled to the Golgi for additional, but divergent processing. The Alg3 gene encodes the enzyme α-1,3-mannosyltransferase that converts Man5GlcNAc2-Dol-PP to Man6GlcNAc2-Dol-PP on the ER membrane of the luminal side. Provided herein is a homolog of *Saccharomyces cerevisiae* Alg3 identified from *Aspergillus niger* (e.g., see SEQ ID NOS: 1 and 2).

It is shown herein that genetic inactivation of Alg3 in *A. niger* resulted in a significant reduction of growth on complete medium (CM) and potato dextrose agar medium (PDA), but no effect on minimal medium (MM). The Alg3 deletion also caused the substantial reduction in spore production of *A. niger* on CM, but no significant change on the PDA. When the spores were germinated in CM or PDA liquid culture medium, the Alg3Δ strain showed pronounced delay in spore germination. This growth phenotype is similar to the mutants with defects in signal transduction pathways observed in *A. nidulans* and *A. niger* (Fillinger et al., *Mol. Microbiol.* 44(4):1001-16, 2002; Saudohar et al., *Microbiol.* 148(8):2635-45, 2002; Xue et al., *Eukaryot Cell* 3(2):557-60, 2004). Deletion of pkaA, cycaA or schA/pkaA in *A. nidulans* substantially reduces its growth on CM medium plates and spore germination rate in MM liquid culture medium (Fillinger et al., *Mol. Microbiol.* 44(4):1001-1016, 2002) and similar growth phenotypes were observed in the strains with the deletion of pkaR, pkaC or double deletion of pkaR/pkaC in *A. niger* (Saudohar et al., *Microbiol.* 148(8):2635-2645, 2002). However, functional deletion of the MAP kinase SakA in *A. fumigatus* delays the spore germination in liquid CM, but stimulates spore germination in MM liquid medium (Xue et al., *Eukaryot Cell* 3(2): 557-560, 2004).

Figure 8A:
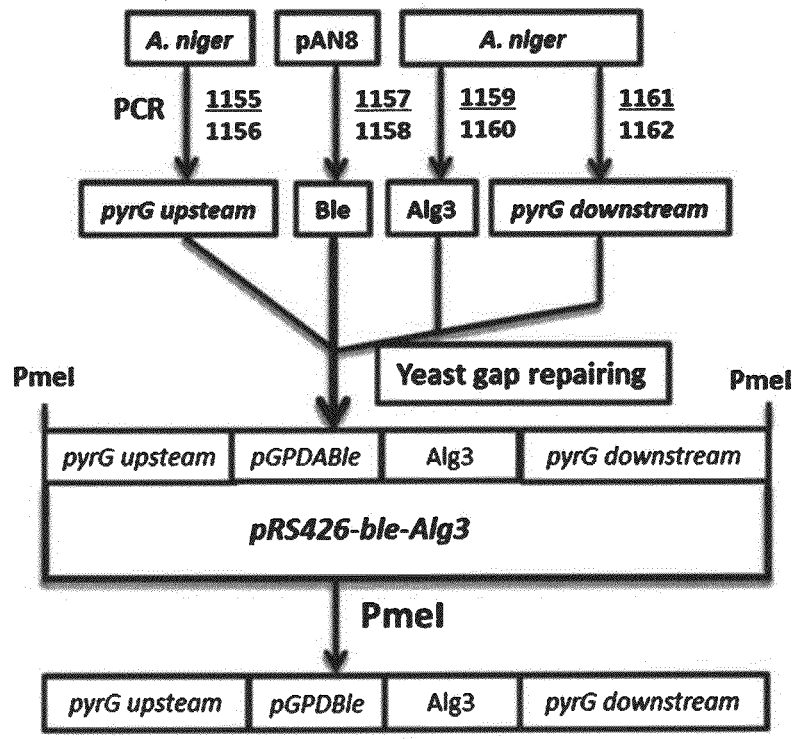
FIGS. 8A and 8B show (A) a schematic diagram showing the construction of the transgene used to complement the Alg3Δ mutant, and (B) a is a graph showing the citric acid production by parent strain 11414kusA (kusA), Alg3Δ mutant (Alg3) and Alg3Δ mutant complemented with Alg3 gene (cAlg3) after growth at 30° C., 200 rpm for 12 days
Figure 8B:
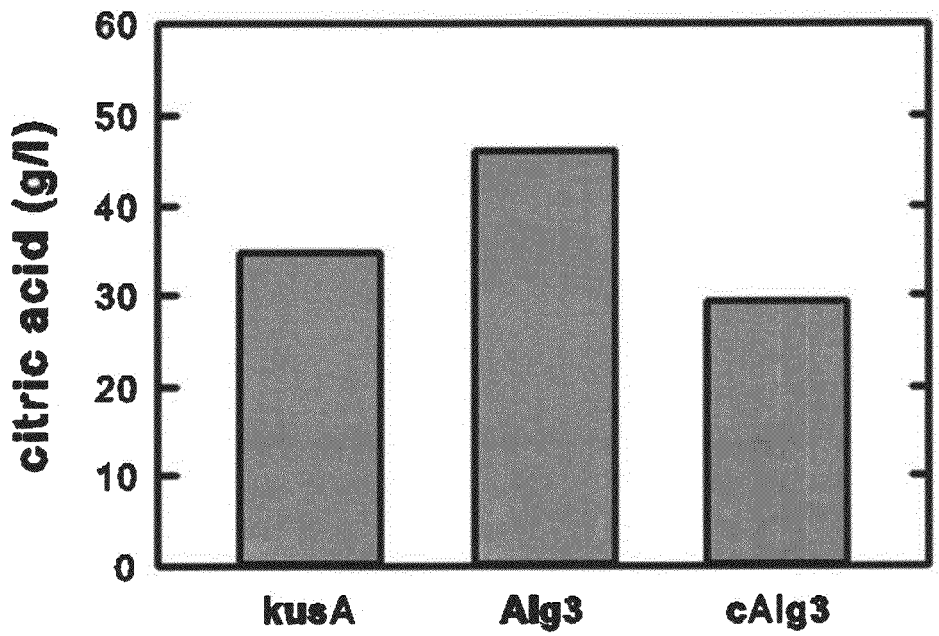

Furthermore, the Alg3 deletion reduced the overall growth on citric acid production (CAP) medium plates at different pHs. In contrast, the Alg3 deletion triggered early spore germination and substantially improved spore germination rate in CAP liquid culture medium. Citric acid production in CAP liquid culture medium was significantly improved in *A. niger*. When the alg3Δ mutant was complemented with the original alg3 gene at pyrG locus (FIG. 8A; SEQ ID NO: 60), its transcription levels was similar to parent strain with the cycle threshold (Ct) values about 23, while the Ct value for alg3Δ mutant was 30.8 in CAP liquid culture conditions, which was determined by real-time reverse-transcription PCR. Consequently, the citric acid production in the resulted complemented mutant strains was similar to the parent strain as shown in FIG. 8B. The results shown herein demonstrate the involvement of Alg3 on the growth and development and citric acid production in *A. niger*.

It is proposed that inactivation of Alg3 influences the N-glycosylation of those proteins involving in signal transduction pathways. The N-glycosylation consensus sequence (N-glycosite) for N-glycosylation in those proteins from the signal transduction pathways was observed. Most of those proteins contained 1 to 7 N-glycosites, such as, 6 N-glycosites found in sskB (map kinase kinase kinase), 7 in Ste11/SteC, 5 in acyA, 5 in rgsA, 6 in rgsC, 4 in gprA, 4 in pkaC2, 4 in flbA and 3 in Gβ. Comparison of these results with previous studies indicates that the effects of the Alg3 deletion on spore germination and growth may be regulated by altering the N-glycosylation in those proteins involved in signal transduction pathways in *A. niger*.

When the Alg3Δ strain was grown on CM medium, spore production of Alg3Δ mutants was dramatically reduced as compared to the parent strain, while maintaining a similar level when grown on PDA medium. This phenotype of sporulation production may be influenced by both endogenous and exogenous factors. For example, protein glycosylation was greatly influenced by culture conditions in filamentous fungi, such as fully glycosylated Cel7A only isolated from MM culture medium (Stals et al., *Glycobiology* 14(8):725-737, 2004). In addition, higher amounts of proteases were secreted by the Alg3Δ strain than the parent in liquid MM culture supplemented 1 g/l yeast extract, which further influenced nutrient uptakes, cellular formation and overall N-glycosylation. This would alter the yield and N-glycosylation in G protein system in *A. niger*, where G protein signaling is crucial for detection of major environmental stimuli for food acquisition, asexual sporulation, and spore germination (Chang et al., *Genetics* 167(3):305, 2004; Li et al., *Annu. Rev. Microbiol.* 61:423-452, 2007).

The spores of parent strain germinated more slowly and had a lower germination rate than the Alg3Δ strain in CAP liquid culture medium, which contains limited nitrogen source (3.1 g/l of $NH_4NO_3$), similar to MM. A similar phenotype was observed when the stress activating kinase, a MAP kinase, was deleted in *A. fumigatus* (SakAΔ strain) and grown in MM liquid culture medium (Xue et al., *Eukaryot Cell* 3(2): 557-560, 2004). The spore germination of SakAΔ strain was dramatically influenced by nitrogen sources. For example, similar rates of spore germination between parent and SakAΔ strains were observed on MM containing 10 mM $NH_4Cl$ or 10 mM Pro, while the spore germination rates of SakAΔ strain was much higher than the parent strain in the MM culture medium containing 10 mM $NaNO_3$, $NaNO_2$, or Phe. In addition, the CAP medium contains high level of glucose and low pH, which contributes additional stresses to *A. niger* growth. Although the Alg3Δ strain had earlier and higher germination in CAP medium, its biomass formation was less than the parent strain at early stages. The dried biomass yields for both parent and Alg3Δ strains were similar after growth in CAP medium for four and half days. However, more citric acid was produced by the Alg3Δ strain than the parent strain. This indicates more glucose was directly converted to citric acid by influence citric acid metabolism and reduction of glucose consumption for complex N-glycan formation and sequentially for other cellular metabolisms.

This disclosure also provides the first demonstration that genetic inactivation of Alg3, in combination with an increase in expression of the loss of aflR expression A (LaeA) gene, can result in substantial improvement of citric acid production in *A. niger*. It is proposed that increased expression of LaeA can also improve citric acid production in *A. niger* or other filamentous fungi. To increase expression of LaeA in fungal cells, a transgene was generated and expressed in *A. niger* as follows. The LaeA gene of *A. nidulans* was operably controlled by glyceraldehyde 3-phosphate dehydrogenase (gpdA) promoter and trpC transcriptional terminator (T trpC) of *A. nidulans*. This chimeric gene was flanked with the upstream of *A. niger* pyrG gene, the pyrithiamine resistance (ptrA) gene of *A. oryzae* and the downstream of *A. niger* pyrG gene. The transgene expression fragment containing the chimeric gene was used to transform the protoplasts of alg3Δ mutants of *A. niger*.

In summary, the deletion of Alg3, increasing expression of LaeA, or both, can be used to increase citric acid production in fungi (such as filamentous fungi, e.g., *A. niger*). In addition, deletion of Alg3 alters the overall N-glycosylation and further influences the spore germination, filamentous growth, sporulation and other organic acid production in *A. niger*.

Alg3Δ Fungi

The present disclosure provides isolated fungi having its Alg3 gene inactivated, wherein such inactivation results in increased citric acid production by the fungi. Such fungi are referred to herein as Alg3Δ fungi. It is disclosed herein that genetic inactivation of Alg3 results in *Aspergillus* fungi that can increase citric acid production as compared to *Aspergillus* having a native Alg3 sequence.

Contemplated herein are isolated fungi containing a genetic inactivation of a dolichyl-P-Man:Man(5)GlcNAc(2)-PP-dolichyl mannosyltransferase gene (Alg3). Any fungus can be used, such as any genus or variety of *Aspergillus*. In particular examples, the disclosed *Aspergillus* fungus is *A. niger*, such as *Aspergillus niger* strain 11414 (American Type Culture Collection (ATCC) No. 11414; NRRL 2270); 1015 (ATCC No. 1015; NRRL 328, CBS 113.46); NRRL 3 (ATCC No. 9029, CBS 120.49, N400); NRRL 3122 (ATCC No. 22343); or 11414KusA-. In other specific examples, the *Aspergillus* is *A. aculeatus*, *A. awamori*, *A. carbonarius*, *A. wentii*, *A. foetidus*, *A. oryzae*, *A. terreus*, or *A. fumigatus*.

In addition, any method for genetic inactivation can be used, as long as the expression of the gene is significantly reduced or eliminated, or the function of the expressed protein is significantly reduced or eliminated. In particular examples, the Alg3 gene is genetically inactivated by complete or partial deletion mutation or by insertional mutation. In some examples genetic inactivation need not be 100% genetic inactivation. In some embodiments, genetic inactivation refers to at least 50%, at least 60%, at least 70%, at least 80%, at least 90%, or at least 95% gene or protein inactivation. The term "reduced" or "decreased" as used herein with respect to a cell and a particular gene or protein activity refers to a lower level of activity than that measured in a comparable cell of the same species. For example, a particular fungi lacking Alg3 activity has reduced Alg3 activity if a comparable fungi not having an Alg3 genetic inactivation has detectable Alg3 activity.

Alg3 sequences are disclosed herein and others are publicly available, for example from GenBank or EMBL. In some examples, the Alg3 gene functionally deleted encodes a protein having at least 80%, at least 90%, at least 95%, at least 97%, or at least 98% sequence identity to SEQ ID NO: 2, 4, 31, 32, 33, 34, 35, or 36. In some examples, the Alg3 gene functionally deleted comprises at least 80%, at least 90%, at least 95%, at least 97%, or at least 98% sequence identity to SEQ ID NO: 1 or 3 or nucleotides 1186-2582 of SEQ ID NO: 1.

The inactivation of Alg3 results in many phenotypes in the fungi. For example, Alg3Δ mutants can have one or more of the following phenotypes: slower growth on citric acid production (CAP) medium, earlier spore germination in CAP medium (for example germination in at least 3 hours, at least 4 hours, or at least 5 hours after inoculation, such as within 3 hours of inoculation), increased spore germination rate in CAP medium, increased citric acid production in CAP medium, slower growth on complete medium (CM) or potato dextrose (PDA) medium, delay initiation of spore germination in CM or PDA medium, reduced sporulation on CM, or combinations thereof.

Such changes (such as increases or decreases) can be relative to a fungi having a wild-type Alg3 gene, such as a parental strain (e.g., *A. niger* strain 11414KusA), grown under the same conditions as the Alg3Δ mutant. In some examples, an increased germination rate is germination of at least 20%, at least 25%, or at least 30% of the spores from an Alg3Δ fungus have germinated 8 hours after inoculation in CAP medium (such as 20% to 35%, such as 32%), as compared to no more than 20%, no more than 15%, or no more than 10% (such as 5 to 15%, or 10%) for *A. niger* strain 11414KusA. In some examples, an increased germination rate is germination of at least 80%, at least 85%, or at least 90% of the spores from an Alg3Δ fungus have germinated 15 hours after inoculation in CAP medium (such as 80% to 95%, such as 90%), as compared to no more than 60%, no more than 65%, or no more than 75% (such as 55 to 65%, or 60%) for *A. niger* strain 11414KusA. In some examples, increased citric acid production in CAP medium is an increase of at least 10%, at least 20%, at least 30%, at least 40%, at least 50%, at least 60%, at least 65%, or at least 70%, by an Alg3Δ fungus as compared to *A. niger* strain 11414KusA. In some examples, reduced sporulation on complete medium is a reduction of sporulation by at least 20%, at least 30%, at least 40%, at least 50%, or at least 60%, (such as a 40% to 60% reduction) by an Alg3Δ fungus as compared to *A. niger* strain 11414KusA.

One skilled in the art will appreciate that additional genes can also be inactivated, wherein the additional genes may or may not provide additional enhancement of citric acid production to the fungus. In one example KusA (e.g., GenBank Accession No. EF061656) is also genetically inactivated.

Also provided by the present disclosure are compositions that include isolated Alg3Δ fungi, such as a growth medium. Also provided by the present disclosure are kits that include isolated Alg3Δ fungi, such as a kit that includes a medium for culturing, storing, or growing the fungus. Exemplary mediums include solid medium (such as those containing agar, for example CM, PDA or MM) and liquid media (such as a fermentation broth, such as CM, MM, or CAP medium).

A. Methods of Functionally Deleting Genes

As used herein, an "inactivated" or "functionally deleted" gene means that the gene has been mutated, for example by insertion, deletion, or substitution (or combinations thereof) of one or more nucleotides such that the mutation substantially reduces (and in some cases abolishes) expression or biological activity of the encoded gene product. The mutation can act through affecting transcription or translation of the gene or its mRNA, or the mutation can affect the polypeptide product itself in such a way as to render it substantially inactive.

Genetic inactivation of one or more genes (which in some examples is also referred to as functional deletion) can be performed using any conventional method known in the art. In one example, a strain of *Aspergillus* is transformed with a vector which has the effect of down-regulating or otherwise inactivating an Alg3 gene. This can be done by mutating control elements such as promoters and the like which control gene expression, by mutating the coding region of the gene so that any protein expressed is substantially inactive, or by deleting the Alg3 gene entirely. For example, an Alg3 gene can be functionally deleted by complete or partial deletion mutation (for example by deleting a portion of the coding region of the gene) or by insertional mutation (for example by inserting a sequence of nucleotides into the coding region of the gene, such as a sequence of about 1-5000 nucleotides). Thus, the disclosure in some examples provides transformed fungi that include at least one exogenous nucleic acid molecule which genetically inactivates an Alg3 gene (such as a nucleic acid sequence encoding SEQ ID NO: 2 or 4). In one example, such a transformed cell produces more citric acid, for example relative to a comparable fungus with a native Alg3 sequence.

In particular examples, an insertional mutation includes introduction of a sequence that is in multiples of three bases (e.g., a sequence of 3, 9, 12, or 15 nucleotides) to reduce the possibility that the insertion will be polar on downstream genes. For example, insertion or deletion of even a single nucleotide that causes a frame shift in the open reading frame, which in turn can cause premature termination of the encoded Alg3 polypeptide or expression of a substantially inactive polypeptide. Mutations can also be generated through insertion of foreign gene sequences, for example the insertion of a gene encoding antibiotic resistance (such as hygromycin or bleomycin).

In one example, genetic inactivation is achieved by deletion of a portion of the coding region of the Alg3 gene. For example, some, most (such as at least 50%) or virtually the entire coding region can be deleted. In particular examples, about 5% to about 100% of the gene is deleted, such as at least 20% of the gene, at least 40% of the gene, at least 75% of the gene, or at least 90% of the Alg3 gene.

Deletion mutants can be constructed using any of a number of techniques known in the art. In one example, allelic exchange is employed to genetically inactivate one or more genes in *Aspergillus*. A specific example of such a method is described in Example 2 below.

In one example, a strategy using counterselectable markers can be employed which has been utilized to delete genes. For a review, see Reyrat et al. (*Infec. Immun.* 66:4011-4017, 1998). In this technique, a double selection strategy is employed wherein a plasmid is constructed encoding both a selectable and counterselectable marker, with flanking DNA sequences derived from both sides of the desired deletion. The selectable marker is used to select for fungi in which the plasmid has integrated into the genome in the appropriate location and manner. The counterselecteable marker is used to select for the very small percentage of fungi that have spontaneously eliminated the integrated plasmid. A fraction of these fungi will then contain only the desired deletion with no other foreign DNA present.

In another technique, the cre-lox system is used for site specific recombination of DNA (for example see Steiger et al., *Appl. Environ. Microbiol.* 77(1):114, 2011). The system includes 34 base pair lox sequences that are recognized by the bacterial cre recombinase gene. If the lox sites are present in the DNA in an appropriate orientation, DNA flanked by the lox sites will be excised by the cre recombinase, resulting in the deletion of all sequences except for one remaining copy of the lox sequence. Using standard recombination techniques, the targeted gene of interest (e.g., Alg3) can be deleted in the *Aspergillus* genome and to replace it with a selectable marker (for example a gene coding for kanamycin resistance) that is flanked by the lox sites. Transient expression (by electroporation of a suicide plasmid containing the cre gene under control of a promoter that functions in *Aspergillus*) of the cre recombinase should result in efficient elimination of the lox flanked marker. This process will produce a mutant containing the desired deletion mutation and one copy of the lox sequence.

In another method, an Alg3 gene sequence in the *Aspergillus* genome is replaced with a marker gene, such as green fluorescent protein, β-galactosidase, or luciferase. In this technique, DNA segments flanking a desired deletion are prepared by PCR and cloned into a suicide (non-replicating) vector for *Aspergillus*. An expression cassette, containing a promoter active in *Aspergillus* and the appropriate marker gene, is cloned between the flanking sequences. The plasmid is introduced into wild-type *Aspergillus*. Fungi that incorporate and express the marker gene are isolated and examined for the appropriate recombination event (replacement of the wild type Alg3 gene with the marker gene).

Thus, for example, a fungal cell can be engineered to have a disrupted Alg3 gene using common mutagenesis or knockout technology. (Methods in Yeast Genetics (1997 edition), Adams, Gottschling, Kaiser, and Sterns, Cold Spring Harbor Press, 1998; Datsenko and Wanner, *Proc. Natl. Acad. Sci. USA* 97: 6640-5, 2000; and Dai et al., *Appl. Environ. Microbiol.* 70(4):2474-85, 2004). Alternatively, antisense technology can be used to reduce or eliminate the activity of Alg3. For example, a fungal cell can be engineered to contain a cDNA that encodes an antisense molecule that prevents Alg3 from being translated. The term "antisense molecule" encompasses any nucleic acid molecule or nucleic acid analog (e.g., peptide nucleic acids) that contains a sequence that corresponds to the coding strand of an endogenous Alg3 gene. An antisense molecule also can have flanking sequences (e.g., regulatory sequences). Thus, antisense molecules can be ribozymes or antisense oligonucleotides. A ribozyme can have any general structure including, without limitation, hairpin, hammerhead, or axehead structures, provided the molecule cleaves RNA. Further, gene silencing can be used to reduce the activity of Alg3.

B. Measuring Gene Inactivation

A fungus having an inactivated Alg3 gene can be identified using any method known in the art. For example, PCR and nucleic acid hybridization techniques, such as Northern and Southern analysis, can be used to confirm that a fungus has an inactivated Alg3 gene. Alternatively, real-time reverse transcription PCR (qRT-PCR) can be used for detection and quantification of targeted messenger RNA, such as mRNA of Alg3 gene in the parent and mutant strains as grown at the same culture conditions. Immunohisto-chemical and biochemical techniques can also be used to determine if a cell expresses Alg3 by detecting the expression of the Alg3 peptide encoded by Alg3. For example, an antibody having specificity for Alg3 can be used to determine whether or not a particular fungus contains a functional nucleic acid encoding Alg3 protein. Further, biochemical techniques can be used to determine if a cell contains a particular gene inactivation by detecting a product produced as a result of the expression of the peptide. For example, structural determination of N-glycans excised from glycoproteins can indicate that a fungal cell contains an inactivated Alg3 gene. In addition, measurements of sporulation, germination, secondary metabolite production, and citric acid production can be measured using the methods described herein.

C. Measuring Citric Acid Production

Methods of determining whether a genetic inactivation of Alg3 in *Aspergillus* increases citric acid production, for example relative to the same strain with a native Alg3 sequence (such as a parental strain), are routine in the art. Although particular examples are disclosed herein, the methods are not limiting.

For example, production of citric acid by *Aspergillus* (such as an Alg3Δ strain) can be measured using a spectrophotometric assay. In one example citric acid production can be determined with an endpoint spectrophotometric enzyme assay (for example see, Bergmeyer, H. U. 1985. Metabolites 2: tri- and dicarboxylic acids, purines, pyrimidines and derivatives, coenzymes, inorganic compounds, p. 5-10. In Citric acids. VCH Publishers, Weinheim, Germany). Citric acid can also be measured by liquid chromatography (LC) or high-performance liquid chromatography (HPLC) methods.

D. Alg3 Sequences

Alg3 protein and nucleic acid sequences are publicly available and specific examples are provided herein. In addition, Alg3 sequences can be identified using routine molecular biology methods.

Examples of Alg3 nucleic acid sequences shown in SEQ ID NOS: 1 and 3. However, the disclosure also encompasses variants of SEQ ID NOS: 1 and 3 which retain the ability to encode an Alg3 protein. One skilled in the art will understand that variant Alg3 nucleic acid sequences can be inactivated. Variant sequences may contain a single insertion, a single deletion, a single substitution, multiple insertions, multiple deletions, multiple substitutions, or any combination thereof (e.g., single deletion together with multiple insertions). In addition, the degeneracy of the code permits multiple nucleic acid sequences to encode the same protein. For example, FIG. 9 shows an alignment of Alg3 nucleic acid sequences from *A. niger* (nucleotides 1986-2518 of SEQ ID NO: 1) and *A. oryzae* (nucleotides 643-1175 of SEQ ID NO: 3), which permits one to identify nucleotides that can tolerate substitution (e.g., those that are not conserved between species) and those that may not (e.g., those that are conserved between species). Such nucleic acid molecules can share at least 80%, at least 85%, at least 90%, at least 95%, at least 97%, at least 98%, or at least 99% sequence identity to any known Alg3 nucleic acid sequence, such as SEQ ID NO: 1 or 3 or nucleotides 1186-1306, 1393-1916 and 1989-2582 of SEQ ID NO: 1.

Examples of Alg3 protein sequences shown in SEQ ID NOS: 2, 4, 31, 32, 33, 34, 35, and 36. However, the disclosure also encompasses variants SEQ ID NOS: 2, 4, 31, 32, 33, 34, 35, and 36 which retain Alg3 activity. One skilled in the art will understand that variant Alg3 enzyme sequences can be inactivated. Variant sequences may contain a single insertion, a single deletion, a single substitution, multiple insertions, multiple deletions, multiple substitutions, or any combination thereof (e.g., single deletion together with multiple insertions). Such polypeptides share at least 80%, at least 85%, at least 90%, at least 95%, at least 97%, at least 98%, or at least 99% sequence identity to an Alg3 sequence, such as SEQ ID NO: 2, 4, 31, 32, 33, 34, 35, or 36.

Variant sequences can be identified, for example by aligning known Alg3 sequences. For example, FIGS. 10A and 10B show the alignment of seven different Alg3 sequences from different organisms. In addition, FIG. 11 shows a detailed alignment of Alg3 protein sequences from *A. niger* (amino acids 12-411 of SEQ ID NO: 2) and *S. cerevisiae*, indicating amino acids that are identical, conserved (+) or not conserved (space). Based on these alignments, variants of Alg3 sequences can be identified. For example, amino acid residues that are conserved between organisms are ones that should not be substituted (such as amino acids M50, T70, Y81, Q100 and D150 based on the numbering for *A. niger*), while amino acid residues that are not conserved between organisms are ones likely to tolerate substitution (such as amino acids R8, L160, S395 and N405 based on the numbering for *A. niger*). Similarly, amino acid positions in FIGS.

10A and 10B indicated with different amino acids at the same position are ones likely to tolerate substitution, while positions with the same amino acid (*) are not.

In some examples, an Alg3 sequence that is to be genetically inactivated encodes or includes one or more conservative amino acid substitutions. A conservative amino acid substitution is a substitution of one amino acid (such as one found in a native sequence) for another amino acid having similar biochemical properties. Typically, conservative substitutions have little to no impact on the activity of a resulting peptide. In one example, an Alg3 sequence (such as any of SEQ ID NOS: 2, 4, 31, 32, 33, 34, 35, or 36) includes one or more amino acid substitutions (for example at 1, 2, 5 or 10 residues). Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val. Further information about conservative substitutions can be found in, among other locations in, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988), WO 00/67796 (Curd et al.) and in standard textbooks of genetics and molecular biology.

The Alg3 gene inactivated in a fungus, in particular examples, includes a sequence that encodes an Alg3 protein having at least at least 80%, at least 85%, at least 90%, at least 95%, at least 97%, at least 98%, or at least 99% sequence identity to an Alg3 sequence, such as SEQ ID NO: 2, 4, 31, 32, 33, 34, 35, or 36, wherein the protein can catalyze the addition of the first dol-p-man derived mannose in an α-1,3 linkage to Man5GlcNAc2-PP-Dol. In a specific example, the Alg3 gene inactivated in a fungus encodes an Alg3 protein shown in SEQ ID NO: 2, 4, 31, 32, 33, 34, 35, or 36.

The Alg3 gene that is to be inactivated in a fungus, in particular examples, includes a sequence having at least at least 80%, at least 85%, at least 90%, at least 95%, at least 97%, at least 98%, or at least 99% sequence identity to an Alg3 nucleic acid sequence, such as SEQ ID NO: 1 or 3 or nucleotides 1186-1306, 1393-1916 and 1989-2582 of SEQ ID NO: 1, and encode an Alg3 protein that can catalyze the addition of the first dol-p-man derived mannose in an α-1,3 linkage to Man5GlcNAc2-PP-Dol. In a specific example, the Alg3 gene inactivated in a fungus is shown in SEQ ID NO: 2 or 4.

One skilled in the art will appreciate that additional Alg3 sequences can be identified using any method such as those described herein. For example, Alg3 nucleic acid molecules that encode an Alg3 protein can be identified and obtained using common molecular cloning or chemical nucleic acid synthesis procedures and techniques, including PCR. In addition, standard nucleic acid sequencing techniques and software programs that translate nucleic acid sequences into amino acid sequences based on the genetic code can be used to determine whether or not a particular nucleic acid has any sequence homology with known Alg3 sequences. Sequence alignment software such as MEGALIGN (DNASTAR, Madison, Wis., 1997) can be used to compare various sequences.

In addition, nucleic acid hybridization techniques can be used to identify and obtain a nucleic acid molecule that encodes an Alg3 protein. Briefly, any known Alg3 nucleic acid molecule, or fragment thereof, can be used as a probe to identify similar nucleic acid molecules by hybridization under conditions of moderate to high stringency. Such similar nucleic acid molecules then can be isolated, sequenced, and analyzed to determine whether the encoded protein is an Alg3 protein.

Any method can be used to introduce an exogenous nucleic acid molecule into a fungal cell, for example to genetically inactivate Alg3. For example, chemical mediated-protoplast transformation, electroporation, *Agrobacterium*-mediated transformation, fusion of protoplasts, and biolistic delivery are common methods for introducing nucleic acid into fungal cells. (See, e.g., Ito et al., *J. Bacteriol.* 153:163-8, 1983; Durrens et al., *Curr. Genet.* 18:7-12, 1990; Sambrook et al., *Molecular cloning: A laboratory manual*, Cold Spring Harbour Laboratory Press, New York, USA, third edition, 2001; and Becker and Guarente, *Methods in Enzymology* 194:182-7, 1991. An exogenous nucleic acid molecule contained within a particular cell of the disclosure can be maintained within that cell in any form. For example, exogenous nucleic acid molecules can be integrated into the genome of the cell or maintained in an episomal state. That is, a cell can be a stable or transient transformant.

Fungi with Increased LaeA Expression or Increased LaeA Expression and Alg3 Deletion The present disclosure provides isolated fungi having increased LaeA expression, wherein such increased expression or activity (for example in combination with an Alg3 functional inactivation, Alg3Δ) results in increased citric acid production by the fungi. Such fungi are referred to herein as increased LaeA fungal strains. It is disclosed herein that increased expression of LaeA (for example in combination with genetic inactivation of Alg3, Alg3Δ) results in *Aspergillus* fungi that can increase citric acid production as compared to *Aspergillus* having native LaeA levels of expression.

Contemplated herein are isolated fungi having increased LaeA activity/expression, for example in combination with a genetic inactivation of Alg3. Any fungus can be used, such as any genus or variety of *Aspergillus*. In particular examples, the *Aspergillus* fungus is *A. niger*, such as *Aspergillus niger* strain 11414 (American Type Culture Collection (ATCC) No. 11414; NRRL 2270); 1015 (ATCC No. 1015; NRRL 328, CBS 113.46); NRRL 3 (ATCC No. 9029, CBS 120.49, N400); NRRL 3122 (ATCC No. 22343); or 11414KusA-. In other specific examples, the *Aspergillus* is *A. aculeatus*, *A. awamori*, *A. carbonarius*, *A. wentii*, *A. foetidus*, *A. fumigatus*, *A. oryzae*, or *A. terreus*.

Any method for genetic enhancement or up-regulation can be used, as long as the expression of the gene and/or gene product is significantly increased, or the function of the expressed protein is significantly increased. In particular examples, LaeA gene expression is up-regulated by transformation of the fungi with one or more copies of a LaeA coding or genomic sequence (which can be a native or non-native LaeA sequence). In some embodiments, up-regulation refers to an increase in gene or protein expression of at least 20%, at least 40%, at least 50%, at least 100%, at least 150%, at least 200%, at least 300%, or at least 500%, for example relative to the parental fungal strain without the additional copies of an LaeA gene. The term "increased" or "up-regulated" as used herein with respect to a cell and a particular gene or protein activity refers to a higher level of activity than that measured in a comparable cell of the same species. For example, a particular fungi having increased or up-regulated LaeA activity has increased LaeA activity if a comparable fungi having native LaeA activity has less detectable LaeA activity (for example as measured by gene or protein expression).

LaeA sequences are disclosed herein and others are publicly available, for example from GenBank or EMBL. In some examples, the LaeA gene upregulated encodes a protein having at least 80%, at least 90%, at least 95%, at least 97%, or at least 98% sequence identity to SEQ ID NO: 41 or 59. In some examples, the LaeA gene upregulated comprises at least 80%, at least 90%, at least 95%, at least 97%, or at least 98% sequence identity to SEQ ID NO: 40 (e.g., nt 1-236 and 367-1252 of SEQ ID NO: 41) or 58 (e.g., nt 1-230 and 373-1267 of SEQ ID NO: 58).

Increasing LaeA activity (for example in combination with genetic inactivation of Alg3) results in many phenotypes in the fungi. For example, such recombinant fungi exhibit increased citric acid production in CAP medium. Such increases can be relative to a fungi having a native or wild-type level of LaeA (or LaeA and Alg3) gene or protein expression, such as a parental strain (e.g., *A. niger* strain 11414KusA), grown under the same conditions as the fungi with increased LaeA activity (or increased LaeA activity and decreased Alg3 activity). In some examples, increased citric acid production in CAP medium is an increase of at least 20%, at least 30%, at least 50%, at least 60%, at least 65%, or at least 70%, by such a recombinant fungus as compared to *A. niger* strain 11414KusA. In some examples, recombinant fungi with increased LaeA activity (for example in combination with genetic inactivation of Alg3) have increased sporulation relative to *A. niger* Alg3Δ on MM, accumulate red color pigments to *A. niger* strain 11414KusA on complete medium, or both.

One skilled in the art will appreciate that additional genes can also be inactivated or upregulated, wherein the additional genes may or may not provide additional enhancement of citric acid production to the fungus. In one example KusA (e.g., GenBank Accession No. EF061656) is also genetically inactivated.

Also provided by the present disclosure are compositions that include isolated LaeA up-regulated fungi, such as a growth medium. Also provided by the present disclosure are kits that include isolated LaeA up-regulated fungi, such as a kit that includes a medium for culturing, storing, or growing the fungus. Exemplary mediums include solid medium (such as those containing agar, for example CM, PDA or MM) and liquid media (such as a fermentation broth, such as CM, MM, or CAP medium).

A. Methods of Up-Regulating Gene and/or Protein Expression

As used herein, an "activated" or "up-regulated" gene means that expression of the gene or gene product (e.g., protein) has been up-regulated, for example by introduction of additional copies of the appropriate gene or coding sequence into the fungus (or other common molecular biology methods), such that the introduce nucleic acid sequence is expressed, resulting in increased expression or biological activity of the encoded gene product.

Increasing expression of one or more genes (which in some examples is also referred to as up-regulation) can be performed using any conventional method known in the art. In one example, a strain of *Aspergillus* is transformed with a vector which has the effect of up-regulating or otherwise activating a LaeA gene (such as a native or non-native LaeA gene). This can be done by introducing one or more LaeA coding sequences (such as a gene sequence), whose expression is controlled by elements such as promoters and the like which control gene expression, by introducing a nucleic acid sequence which itself (or its encoded protein) can increase LaeA protein activity in the fungus, or by introducing another molecule (such as a protein or antibody) increases LaeA protein activity in the fungus. For example, a LaeA gene can be up-regulated by introduction of a vector that includes one or more LaeA sequences (such as 1, 2, 3, 4, 5, 6, 7, 8, 9 or 10 LaeA sequences or copies of such sequences) into the desired fungus. In some examples, such LaeA sequences are from different fungal species, can be multiple copies from a single species, or combinations thereof, such as LaeA sequences from at least 2, 3, 4, 5, 6, 7, 8, 9, or 10 different fungal species. In some examples, the LaeA sequence(s) introduced into the fungus is optimized for codon usage. Thus, the disclosure in some examples provides transformed fungi that include at least one exogenous nucleic acid molecule which includes a LaeA gene or coding sequence (such as a nucleic acid sequence encoding SEQ ID NO: 41 or 59), for example in combination with Alg3Δ. In one example, such transformed cells produce more citric acid, for example relative to a comparable fungus with a native LaeA sequence (or a native LaeA sequence combined with a native Alg3 sequence).

In another technique, the cre-lox system is used for site specific recombination of DNA (for example see Steiger et al., *Appl. Environ. Microbiol.* 77(1):114, 2011). The system includes 34 base pair lox sequences that are recognized by the bacterial cre recombinase gene. If the lox sites are present in the DNA in an appropriate orientation, DNA flanked by the lox sites will be excised by the cre recombinase, resulting in the deletion of all sequences except for one remaining copy of the lox sequence. Using standard recombination techniques, the targeted gene of interest (e.g., LaeA) can be deleted in the *Aspergillus* genome and replaced with one or more copies of a non-native LaeA sequence (for example in *A. niger*, replacing one or both *A. niger* LaeA sequences with one or more, or combination of, LaeA sequences from *A. nidulans, A. flavus, fusarium oxysperorum, penicillium chrysogenum*, which have high secondary metabolite production) flanked by the lox sites. Transient expression (by electroporation of a suicide plasmid containing the cre gene under control of a promoter that functions in *Aspergillus*) of the cre recombinase should result in efficient elimination of the lox flanked marker. This process will produce a fungus containing the desired insertion mutation and one copy of the lox sequence.

In one example, one or more LaeA genes are introduced into fugal cells by chemical mediated proteoplast transformation in combination of yeast-gap repairing method for transgene expression construction.

In one example, a transgene is generated and expressed in the desired fungal cell, such as an Alg3Δ cell, to increase LaeA expression. For example, such a transgene can include a LaeA genomic or cDNA sequence (such as one having at least 80%, at least 85%, at least 90%, at least 95%, at least 97%, at least 98%, or at least 99% sequence identity to any known LaeA sequence, such as SEQ ID NO: 40 or 58), for example operably linked to a promoter, such as a glyceraldehyde 3-phosphate dehydrogenase (gpdA) promoter or other promoter, such as one that has high activity in CAP culture medium, for example a polyubiquitin promoter, Arsa-7, and A-37 from *A. niger*. In one example, the promoter has at least 80%, at least 85%, at least 90%, at least 95%, at least 97%, at least 98%, or at least 99% sequence identity to SEQ ID NO: 37. In one example, the promoter comprises or consists of the sequence shown in SEQ ID NO: 37. In some examples, the transgene further includes pyrG upstream and downstream sequences (for example that are at the 5'- and 3'-end, respectively, of the transgene). The pyrG gene in *A. niger* is mutated and has lost its original functions. Thus, other non-essential gene loci can be used as long as it is not influenced by the native neighbor genes. In one example, the pyrG upstream and downstream sequences have at least 80%, at least 85%, at least 90%, at least 95%, at least 97%, at least 98%, or at least 99% sequence identity to SEQ ID NO: 45 and 48, respectively. In one example, the pyrG upstream and downstream sequences comprise or consist of the sequence shown in SEQ ID NO: 45 or 48, respectively. In some examples, the transgene further includes a trpC transcriptional terminator sequence of *A. nidulans*, for example downstream of the LaeA sequence. As an alternative to trpC, other transcriptional terminators can be used, such as promoters which include a transcriptional terminators (e.g., ArsA7, Arsa-37, polyubiquitin (ubi4)). In one example, the trpC transcriptional terminator has at least 80%, at least 85%, at least 90%, at least 95%, at least 97%, at least 98%, or at least 99% sequence identity to SEQ ID NO: 46. In one example, the trpC transcriptional terminator comprises or consists of the sequence shown in SEQ ID NO: 46. In some examples, the transgene further includes a ptrA sequence, for example downstream of the trpC transcriptional terminator sequence. As an alternative to ptrA, the bleomycin gene or bar gene can be used. In one example, the ptrA sequence has at least 80%, at least 85%, at least 90%, at least 95%, at least 97%, at least 98%, or at least 99% sequence identity to SEQ ID NO: 47. In one example, the ptrA sequence comprises or consists of the sequence shown in SEQ ID NO: 47. In one example, the transgene comprises a sequence having at least 80%, at least 85%, at least 90%, at least 95%, at least 97%, at least 98%, or at least 99% sequence identity to SEQ ID NO: 44 or 57. In one example, the transgene comprises or consists of the sequence shown in SEQ ID NO: 44 or 57.

Thus, for example, a fungal cell can be engineered to have increased copies of LaeA using common recombinant technology methods.

B. Measuring Gene Activation or Up-Regulation

A fungus having an activated or up-regulated LaeA gene can be identified using any method known in the art. For example, PCR and nucleic acid hybridization techniques, such as Northern, RT-PCR, and Southern analysis, can be used to confirm that a fungus has an up-regulated LaeA gene, such as an increase in the LaeA copy number. Immunohistochemical and biochemical techniques can also be used to determine if a cell expresses LaeA by detecting the expression of the LaeA peptide encoded by LaeA. For example, an antibody having specificity for LaeA can be used to determine whether or not a particular fungus has increased LaeA protein expression. Further, biochemical techniques can be used to determine if a cell has increased LaeA expression by detecting a product produced as a result of the expression of the peptide. For example, measurement of secondary metabolites can indicate that a fungal cell contains an up-regulated LaeA gene. In addition, measurements of citric acid production can be measured using the methods described herein.

C. Measuring Citric Acid Production

Methods of determining whether a genetic up-regulation of LaeA (alone or in combination with inactivation of Alg3) in *Aspergillus* increases citric acid production, for example relative to the same strain with a native LaeA sequence, Alg3 sequence, or both (such as a parental strain), are routine in the art. Although particular examples are disclosed herein (see above and in the examples below), the methods are not limiting.

D. LaeA Sequences

LaeA protein and nucleic acid sequences are publicly available and specific examples are provided herein. In addition, LaeA sequences can be identified using routine molecular biology methods.

Examples of LaeA nucleic acid sequences shown in SEQ ID NOS: 40 and 58. However, the disclosure also encompasses variants of SEQ ID NOS: 40 and 58 (such as the coding regions nt 1-236 and 367-1252 of SEQ ID NO: 41 and nt 1-230 and 373-1267 of SEQ ID NO: 58) which retain the ability to encode a LaeA protein. One skilled in the art will understand that variant LaeA nucleic acid sequences can be used to increase expression of LaeA. Variant sequences may contain a single insertion, a single deletion, a single substitution, multiple insertions, multiple deletions, multiple substitutions, or any combination thereof (e.g., single deletion together with multiple insertions). In addition, the degeneracy of the code permits multiple nucleic acid sequences to encode the same protein. Thus, in one example, a LaeA sequence having at least 80%, at least 85%, at least 90%, at least 95%, at least 97%, at least 98%, or at least 99% sequence identity to any known LaeA sequence, such as SEQ ID NO: 40 or 58 (such as the coding regions nt 1-236 and 367-1252 of SEQ ID NO: 41 and nt 1-230 and 373-1267 of SEQ ID NO: 58) can be expressed in a fungal cell to increase LaeA expression in the fungal cell.

For example, FIG. 12 shows an alignment of LaeA protein sequences from *A. nidulans* (aa 14-372 of SEQ ID NO: 41) and *A. niger* (aa 14-370 of SEQ ID NO: 59), which permits one to identify amino acids that can tolerate substitution (e.g., those that are not conserved between species) and those that may not (e.g., those that are conserved between species). Based on these alignments, variants of LaeA sequences can be identified. For example, amino acid residues that are conserved between organisms are ones that should not be substituted (such as amino acids S16, M42, and P52 based on the numbering for *A. nidulans*), while amino acid residues that are not conserved between organisms are ones likely to tolerate substitution (such as amino acids T15, S44, and N325 based on the numbering for *A. nidulans*). Similarly, amino acid positions in FIG. 12 indicated with a space are ones likely to tolerate substitution, while positions with the same amino acid are not.

Such protein molecules can share at least 80%, at least 85%, at least 90%, at least 95%, at least 97%, at least 98%, or at least 99% sequence identity to any known LaeA nucleic acid sequence, such as SEQ ID NOS: 41 and 59, and such variants can be used to increase LaeA activity in a fungal cell. One skilled in the art will understand that variant LaeA enzyme sequences can be used to increase LaeA activity in a fungal cell. Variant sequences may contain a single insertion, a single deletion, a single substitution, multiple insertions, multiple deletions, multiple substitutions, or any combination thereof (e.g., single deletion together with multiple insertions).

In some examples, a LaeA sequence whose expression is to be up-regulated encodes or includes one or more conservative amino acid substitutions. A conservative amino acid substitution is a substitution of one amino acid (such as one found in a native sequence) for another amino acid having similar biochemical properties. Typically, conservative substitutions have little to no impact on the activity of a resulting peptide. In one example, a LaeA sequence (such as any of SEQ ID NOS: 41 and 59) includes one or more amino acid substitutions (for example at 1, 2, 5 or 10 residues). Examples of amino acids which may be substituted for an original amino acid in a protein and which are regarded as conservative substitutions include those discussed above for Alg3.

The LaeA gene up-regulated in a fungus, in particular examples, includes a sequence that encodes a LaeA protein having at least at least 80%, at least 85%, at least 90%, at least 95%, at least 97%, at least 98%, or at least 99% sequence identity to an LaeA sequence, such as SEQ ID NO: 41 or 59, wherein the protein can regulate secondary metabolite production in *Aspergillus*. In a specific example, the LaeA gene up-regulated in a fungus encodes a LaeA protein shown in SEQ ID NO: 41 or 59.

The LaeA gene up-regulated in a fungus, in particular examples, includes a sequence having at least at least 80%, at least 85%, at least 90%, at least 95%, at least 97%, at least 98%, or at least 99% sequence identity to a LaeA nucleic acid sequence, such as SEQ ID NO: 40 or 58 (or to the coding regions nt 1-236 and 367-1252 of SEQ ID NO: 41 or nt 1-230 and 373-1267 of SEQ ID NO: 58), and encodes a LaeA protein which can regulate secondary metabolite production in *Aspergillus*. In a specific example, the LaeA gene upregulated in a fungus is shown in SEQ ID NO: 40 or 58 (or includes the coding regions nt 1-236 and 367-1252 of SEQ ID NO: 41 or nt 1-230 and 373-1267 of SEQ ID NO: 58).

One skilled in the art will appreciate that additional LaeA sequences can be identified and obtained using any method such as those described herein. For example, LaeA nucleic acid molecules that encode a LaeA protein can be identified and obtained using common molecular cloning or chemical nucleic acid synthesis procedures and techniques, including PCR. In addition, standard nucleic acid sequencing techniques and software programs that translate nucleic acid sequences into amino acid sequences based on the genetic code can be used to determine whether or not a particular nucleic acid has any sequence homology with known LaeA sequences. Sequence alignment software such as MEGA-LIGN (DNASTAR, Madison, Wis., 1997) can be used to compare various sequences.

In addition, nucleic acid hybridization techniques can be used to identify and obtain a nucleic acid molecule that encodes a LaeA protein. Briefly, any known LaeA nucleic acid molecule, or fragment thereof, can be used as a probe to identify similar nucleic acid molecules by hybridization under conditions of moderate to high stringency. Such similar nucleic acid molecules then can be isolated, sequenced, and analyzed to determine whether the encoded protein is a LaeA protein. The gene specific oligonucleotide pair can also be designed, synthesized and used for real-time RT-PCR to quantify the LaeA gene transcription level.

Any method can be used to introduce an exogenous nucleic acid molecule into a fungal cell, for example to genetically enhance LaeA expression. For example, chemical mediated-protoplast transformation, electroporation, *Agrobacterium*-mediated transformation, fusion of protoplasts, and biolistic delivery are common methods for introducing nucleic acid into fungal cells. (See, e.g., Ito et al., *J. Bacteriol.* 153:163-8, 1983; Durrens et al., *Curr. Genet.* 18:7-12, 1990; Sambrook et al., *Molecular cloning: A laboratory manual*, Cold Spring Harbour Laboratory Press, New York, USA, second edition, 1989; and Becker and Guarente, *Methods in Enzymology* 194:182-7, 1991). An exogenous nucleic acid molecule contained within a particular cell of the disclosure can be maintained within that cell in any form. For example, exogenous nucleic acid molecules can be integrated into the genome of the cell or maintained in an episomal state. That is, a cell can be a stable or transient transformant.

Production of Citric Acid Using Alg3Δ Mutants, Fungi with Increased LaeA Expression, or Both The fungi provided herein, namely Alg3Δ fungi, up-regulated LaeA fungi, and fungi with both Alg3Δ and up-regulated LaeA, can be used to produce citric acid, as well as derivatives thereof such as hydroxycitric acid (for example for medical applications). Such fungi can be from any species, such as *Aspergillus* or *Rhizopus* cells. For example, the disclosure provides methods of making citric acid, which can include culturing Alg3Δ fungi, up-regulated LaeA fungi, or fungi with both Alg3Δ and up-regulated LaeA, under conditions that permit the fungus to make citric acid, for example in CAP medium.

Citric acid (2-hydroxy-propane-1,2,3-tricarboxylic acid) combines a pleasant taste with low toxicity and palatability and is a ubiquitous food additive. It is also able to complex heavy metal ions, like iron and copper, and is therefore applied in the stabilization of oils and fats or ascorbinic acid during metal ion-catalyzed oxidation reactions. Consequently, it is today one of the bulk products produced by fermentation, most of which occurs with the fungus *Aspergillus niger*, although a small portion is also produced by fermentation with yeast, such as *Candida oleophila* and *Candida lipolytica*.

Citric acid production generally requires a unique combination of several unusual nutrient conditions (e.g., excessive concentrations of carbon source, and dissolved oxygen, or suboptimal concentrations of certain trace metals and phosphate), which synergistically influence the yield of citric acid. Table 1 below shows the environmental parameters that influence citric acid accumulation.

TABLE 1

Parameters that influence citric acid accumulation by *A. niger*

| Parameter | Requirement for citric acid accumulation |
|---|---|
| Carbon source concentration | Higher than 50 g/l |
| Carbon source type | Enable rapid catabolism |
| Nitrogen source | Consumption leads to some decrease in pH |
| Phosphate concentration | Suboptimal |
| Aeration | In excess |
| Trace metal ions | Limiting, especially $Mn^{2+}$ |
| pH | Below pH 3 |

Methods of making citric acid, which can include culturing Alg3Δ fungi, up-regulated LaeA fungi, or fungi with both Alg3Δ and up-regulated LaeA, under conditions that permit the fungus to make citric acid, are provided. In general, the culture media and/or culture conditions can be such that the fungi grow to an adequate density and produce citric acid efficiently. In one example the Alg3Δ fungi, up-regulated LaeA fungi, or fungi with both Alg3Δ and up-regulated LaeA, are cultured or grown in a liquid medium that includes sucrose and/or glucose as the carbon source, for example at a concentration of at least 50 g/liter, such as at least 100 g/l, or at least 140 g/l. Thus, a fungus within the scope of the disclosure in some examples can utilize a variety of carbon sources. In one example the Alg3Δ fungi, up-regulated LaeA fungi, or fungi with both Alg3Δ and up-regulated LaeA, are cultured or grown in a liquid medium that includes a very small amount of manganese, such as less than 100 parts per billion (ppb), less than 50 ppb, less than 20 ppb, less than 15 ppb, for example 5 ppb to 15 ppb or 10 ppb to 15 ppb, such as 5, 10, 13, 15 or 20 ppb. In one example the Alg3Δ fungi, up-regulated LaeA fungi, or fungi with both Alg3Δ and up-regulated LaeA, are cultured or grown in a liquid medium having an initial pH of less than 3, such as less than 2.5, for example about pH 1.8 to 3, 1.8 to 2.5, 1.8 to 2.2, 1.9 to 2.1, for example pH 1.8, 1.9, 2, 2.1, 2.2, 2.3, 2.4, 2.5, 2.6, 2.7, 2.8 or 2.9. In some examples the Alg3Δ fungi, up-regulated LaeA fungi, or fungi with both Alg3Δ and up-regulated LaeA, are cultured or grown in a liquid medium at about 25 to 35° C. with rotation (such as 28 to 32° C., or 30° C.).

In a specific example, the Alg3Δ fungi, up-regulated LaeA fungi, or fungi with both Alg3Δ and up-regulated LaeA, are grown in citric acid production (CAP) medium. In a specific example, the CAP medium includes 140 g of glucose/liter, 3.1 g of $NH_4NO_3$/liter, 0.15 g of $KH_2PO_4$/liter, 0.15 g of NaCl/liter, 2.2 g of $MgSO_4 \cdot 7H_2O$/liter, 6.6 mg of $ZnSO_4 \cdot 7H_2O$/liter, and 0.1 mg of $FeCl_3$/liter adjusted to about pH 2 with 4 M $H_2SO_4$. Cations can be removed from the glucose solution by ion exchange on Dowex 50W-X8, 100/200-mesh, H cation exchange resin (Fisher Scientific, Pittsburgh, Pa.) prior to adding the other nutrient components. The manganese concentration in the medium can be adjusted by the addition of appropriate volumes of a stock solution of $MnCl_2 \cdot 4H_2O$ (10 mM). In one example, the manganese concentration is less than 50 ppb, such as less than 20 ppb, for example 5 to 15 ppb, such as 10 ppb.

Methods of culturing *Aspergillus* to enable citric acid production are well known in the art. In one example, the fungi are grown in culture containers (such as baffled flasks, and in some examples are silanized (5% solution of dichlorodimethylsilane in heptane (Sigma, St. Louis, Mo.)). The Alg3Δ fungi, up-regulated LaeA fungi, or fungi with both Alg3Δ and up-regulated LaeA, provided herein can be grown in CAP media containing low amounts of Mn2+ (e.g., 10 ppb) at 30° C. with rotation (e.g., 200 to 250 rpm) for at least 3 days (e.g., 3 to 7 days). Each culture container is inoculated with spores (such as at least $10^6$ spores/ml) and incubated for at least 12 or at least 15 hours at 30° C. and 200 to 250 rpm to obtain properly pelleted morphology.

In one example, the Alg3Δ fungi, up-regulated LaeA fungi, or fungi with both Alg3Δ and up-regulated LaeA, produce more citric acid than a corresponding fungus with wild-type Alg3. In specific examples, the Alg3Δ fungi, up-regulated LaeA fungi, or fungi with both Alg3Δ and up-regulated LaeA, produce at least 25 g/l of citric acid (for example at least 30 g/l, at least 32 g/l, at least 35 g/l, at least 40 g/l, at least 42 g/l, at least 45 g/l, at least 50 g/l, at least 52 g/l or at least 55 g/l), for example after at least 4 days (such as at least 5 days, at least 6 days, at least 7 days, at least 8 days, or at least 10 days, such as after 4 to 6 days, 8 to 10 days, or 4 to 5 days) when grown in CAP medium at 30° C. with 200 rpm shaking.

In some examples, the method further includes isolating the citric acid made by the Alg3Δ fungi, up-regulated LaeA fungi, or fungi with both Alg3Δ and up-regulated LaeA. Once produced, any method can be used to isolate the citric acid. For example, common separation techniques can be used to remove the fungal biomass from the culture medium, and common isolation procedures (e.g., filtration, distillation, precipitation, electrodialysis, and ion-exchange procedures) can be used to obtain the citric acid from the broth (such as a fungi-free broth). In addition, the citric acid can be isolated from the culture medium after the citric acid production phase has been terminated.

Example 1

Materials and Methods

This example describes methods used in the experiments described in Examples 2-5 below.

Strains and Media.

The *Escherichia coli* strains Top 10 and *Saccharomyces cerevisiae* strain YVH10 were used as hosts for routine cloning and gap repair experiments. *A. niger* strain ATCC 11414 (American Type Culture Collection, Rockville, Md.), was grown on potato dextrose agar plates (PDA) and complete medium (CM) agar plates at 30° C. for culture maintenance and spore preparation, respectively. The mutant strain *Aspergillus niger* 11414KusA was generated by the deletion of kusA in *A. niger* strain 11414 by the replacement with *A. fumigatus* pyrG gene, which encodes the ortholog of the ku70 protein that involves in the non-homologous end joining pathway of DNA repair for the integration of a DNA fragment into the genome in other eukaryotes, and was confirmed by Southern blotting analysis. The 11414kusA strain with high rate of homologous replacement was mainly used as a parent strain. The cultures on PDA or complete medium (CM) agar plates were incubated for four days at 30° C. and the spores were harvested by washing with sterile 0.8% Tween 80 (polyoxyethylenesorbitan monooleate). The CM medium contains 20 g of D-glucose/liter, 5 g yeast extract/liter, 2 g trypticase peptone/liter, 1 g casamino acids/liter, 6 g $NaNO_3$/liter, 0.52 g KCl/liter, 0.52 g $MgSO_4 \cdot 7H_2O$/liter, 1.52 g $KH_2PO_4$/liter, 36.7 mg $ZnSO_4 \cdot 7H_2O$/liter, 18.3 mg $H3BO_3$/liter, 8.3 mg $MnCl_2 \cdot 4H_2O$/liter, 8.3 mg $FeSO_4 7H_2O$, 2.8 mg $CoCl_2 \cdot 6H_2O$/liter, 2.7 mg $CuSO_4 \cdot 5H_2O$/liter, 2.5 mg $Na_2MoO_4 \cdot 2H_2O$/liter, 83.3 mg $Na_2$ EDTA/liter, 1 mg biotin/liter, 1 mg pyridoxin/liter, 1 mg thiamine/liter, 1 mg riboflavin/liter, 1 mg p-aminobenzoic acid/liter and 1 mg nicotinic acid/liter. The PDA medium contains 4 g/liter potato starch and 20 g/liter dextrose. Conidia were enumerated with a hemacytometer. Aliquots of the resulting spore suspension ($1 \times 10^9$ spores/ml) were used to inoculate baffled-flask liquid cultures. The citric acid production (CAP) medium contained 140 g/l of glucose, 3.1 g/l $NH_4NO_3$, 0.15 g/l $KH_2PO_4$, 0.15 g/l NaCl, 2.2 g/l $MgSO_4 \cdot 7H_2O$, 6.6 mg/l $ZnSO_4 \cdot 7H_2O$, and 0.1 mg/l $FeCl_3$ adjusted to pH 2.1 with 4 M $H_2SO_4$. Cations were removed from the glucose solution by ion-exchange on Dowex 50W-X8, 100-200 mesh, H cation exchange resin (Fisher Scientific, Pittsburgh, Pa.) prior to adding the other nutrient components.

Culture Methods.

Glass baffled-flasks of 250 ml or 1000 ml were silanized by rinsing in a 5% solution of dichlorodimethylsilane in heptane (Sigma, St. Louis, Mo.) to minimize leaching of metals. For citric acid production tests, $1 \times 10^{-6}$ spores/ml of parent or mutant strains were grown in 80 ml CAP media containing 10 ppb $Mn^{2+}$ in 250 ml baffled flasks or 220 ml CAP media in 1000 ml baffled flasks at 30° C. and 200 rpm. Samples for citric acid analysis were taken at intervals. The biomass of transgenic clones and parent stain were prepared from 2 ml CM station cultures with proper antibiotics and grown in 16×125 mm glass culture-tubes at 30° C. without shaking. The biomass formed on the surface of the culture medium was collected, frozen immediately in liquid nitrogen and dried in the lyophilizer.

Dried Biomass Measurement:

After proper cultivation, the cell mass from citric acid production culture was collected by centrifugation at room temperature and 4500×g for 5 min in Sorvall floor centrifuge with swinging-bucket rotor. The cell mass was then transferred onto the Whatman Grade No 1 filter paper or left in centrifuge tubes for freeze-drying. The biomass was then dried in high temperature oven at 80° C. or freeze-dried in the lyophilizer. Prior to being used, the centrifuge tube or Whatman filter paper was weighted and re-weighted after the biomass was completely dried.

Total Genomic DNA Isolation for PCR and Southern Blotting Analysis.

Total genomic DNA was isolated from *A. niger* according to the SDS extraction method described previously by Dellaporta et al. (*Plant Molecular Biology Reporter* 1(4):19-21, 1983) with some modifications. Briefly, fungal biomass from 2 ml station cultures was looped and transferred into a 1.5 ml microcentrifuge tube. A needle size hole on the cap was punched with 18 gauge needle. The tube was immediately frozen in liquid $N_2$ for 5 minutes and biomass in the tube was dried in a VirTis benchtop manifold freeze dryer (SP Scientific, Gardiner, N.Y.) overnight. The dried biomass and two 3.5 mm diameter glass beads were transferred into the 2 ml polypropylene microvial, where biomass was pulverized into fine power with Mini-Beadbeater-8 (Bio Spec Products Inc., Bartlesville, Okla.) for one minute. Then, 500 µl of 60° C. extraction buffer and 80 µl of 15% SDS were added into the microcentrifuge tube and incubated at 65° C. for at least 30 minutes with occasionally swirling to mix. Two-hundred microliters of 5M potassium acetate was added, mixed and incubated on ice for 30 minutes. The supernatant was collected by centrifugation at 12,000 g for 10 minutes at 4° C. and transferred into the new microcentrifuge tube. The total nucleic acids were precipitated with 780 µl of 2-propanol for 30 minutes at −20° C. and centrifuged at 12,000 g for 10 minutes. The nucleic acids were re-suspended in 200 µl 50TE buffer containing 2 RNase (10 stock solution) and incubated in Eppendorf thermomixer at 50° C. and 500 rpm for 30 minutes. The proteins and cell debris was removed by being added and well mixed 20 µl 3M sodium acetate and equal volume of phenol:chloroform and centrifuged at 15,000 g for 5 minutes. The supernatant was transferred to new DNase-free microcentrifuge tube containing 220 µl of 2-propanol, mixed well and incubated at room temperature for 5 minutes. The genomic DNA was pelleted by centrifugation at 15,000 g for 10 minutes and washed with 500 µl of 70% ethanol. The genomic DNA was re-suspended in 80 µl 10 mM TrisHCl (pH8.0) buffer and determined with Qubit fluorometer (Invitrogen, Carlsbad, Calif.). One microgram of total genomic DNA was digested with restriction endonuclease BamH and SacII. The genomic DNA fragments were separated in 1% agarose gel electrophoretically and transferred onto the zeta-probe membrane (BioRad) with alkaline capillary transfer method. A 3.8 kb genomic DNA fragment containing the Alg3 sequence was used for preparation of the biotin-labeled probe. The genomic DNA in Zeta-probe membrane was hybridized with the biotin-labeled probe overnight in 60° C. hybridization oven. The genomic DNA on hybridized membrane was visualized with North2South chemiluminescent detection kit (Pierce Protein Research Products, Rockford, Ill.).

Spore Production and Germination.

The spore production on the PDA or CM agar plates described above was excised with plastic closures of culture tubes in 27 mm diameter and transferred into the 50 ml centrifuge tubes containing 25 ml 0.8% tween 80. The spores were released from the agar surface by scraping with plastic loops and vortexed with vortex mixer at top speed. The spores were diluted properly and enumerated with a hemacytometer. The spore production in a unit area ($cm^2$) was determined. For spore germination, $1 \times 10^5$ spores per well were added into each well of 24 well Schwarz sensoplate and incubated in the microscopic incubator with temperature control at 30° C. The spore germination was automatically imaged hourly for 24 hrs through the Olympus inverted system microscope (Olympus America Inc., Center Valley, Pa., USA). The spore germination was visualized with Adobe Photoshop CS5 (San Jose, Calif.) and counted manually.

Citric Acid Measurements.

Citric acid concentrations were determined with an endpoint spectrophotometric enzyme assay as described in the instruction from the manufacturer (R-Biopharm AG/Roche, Darmstadt, Germany) with a proper dilution.

Table 2 shows oligonucleotides used in the methods.

TABLE 2

Oligonucleotides used

| Name | Sequence | Product size (kb) |
|---|---|---|
| Alg3Δ construction | | |
| Alg3-ForScr | CGGTTTCCCTTCAGTTTCCAGT (SEQ ID NO: 5) | |
| Alg3-1 | GTAACGCCAGGGTTTTCCCAGTCACGACGTCATAACTTCTCTCCCCTCC (SEQ ID NO: 6) | 1.06 |
| Alg3-2 | ATCCACTTAACGTTACTGAAATCTCCAACTTCATGGACACACACAGACC (SEQ ID NO: 7) | |
| Hph-F | GGTCTGTGTGTGTCCATGAAGTTGGAGATTTCAGTAACGTTAAGTGGAT (SEQ ID NO: 8) | 1.49 |
| Hph-R | GCTACTACTGATCCCTCTGCGTCGGAGACAGAAGATGATATTGAAGGAG (SEQ ID NO: 9) | 1.03 |
| Alg3-3 | CTCCTTCAATATCATCTTCTGTCTCCGACGCAGAGGGATCAGTAGTAGC (SEQ ID NO: 10) | |
| Alg3-4 | GCGGATAACAATTTCACACAGGAAACAGCCGTGAGAGGTTTGTAGTACG (SEQ ID NO: 11) | |
| Alg3-RevScr | AAGCTGAGAGCGACATCTTCA (SEQ ID NO: 12) | |
| hyg-RevScr | GTACTTCTACACAGCCATCGGTCCA (SEQ ID NO: 13) | |
| hyg-ForScr | GTACTTCTACACAGCCATCGGTCCA (SEQ ID NO: 14) | |
| Alg3Δ + Alg3 construction | | |
| pryGScr | TCTGCTGTCTTGCATGAGGTCCTT (SEQ ID NO: 15) | |
| pyrGScr | Agcgtaggacaaggtcgtctctgt (SEQ ID NO: 16) | |

TABLE 2-continued

Oligonucleotides used

| Name | Sequence | Product size (kb) |
|---|---|---|
| 5-pyrG5F | GTAACGCCAGGGTTTTCCCAGTCACGACgtttaaacATGCATCATTCTC CCGCTTTGT (SEQ ID NO: 17) | 2.34 |
| 5-pyrG3R | agaaagagtcaccggtcacGacatcgccaatcacctcaatcac (SEQ ID NO: 18) | |
| ble5F | gtgattgaggtgattggcgatgtCgtgaccggtgactctttct (SEQ ID NO: 19) | 1.69 |
| Ble3R | TCCAACCTTGTAGCAACCAAAGCTTCGAGCGTCCCAAAACCT (SEQ ID NO: 20) | 1.47 |
| Alg3-5F1 | <u>AGGTTTTGGGACGCTCGAAGCTTTGGTTGCTACAAGGTTGGA</u> (SEQ ID NO: 21) | 1.47 |
| Alg3-3R1 | TCAAGTAGAGCACAGCAAATAGTATCTGA (SEQ ID NO: 22) | 1.23 |
| Alg3-5F2 | TCAGATACTATTTGCTGTGCTCTACTTGA (SEQ ID NO: 23) | |
| Alg3-3R2 | ttgatccttgtgccacaccaTCCTACGTGGTCATCGATACCA (SEQ ID NO: 24) | |
| 3-pyrG5F | <u>TGGTATCGATGACCACGTAGGA</u>tggtgtggcacaaggatcaa (SEQ ID NO: 25) | |
| 3-pyrG3R | GCGGATAACAATTTCACACAGGAAACAGCgtttaaactgtgccagtcaa ttgtccgaagt (SEQ ID NO: 26) | |
| Alg3Seq-1 | TACAGACGCGTGTACGCATGT (SEQ ID NO: 27) | |
| Alg3seq-2 | TGCTATTGTCCACAGATACCGAGA (SEQ ID NO: 28) | |
| Alg3seq-3 | GAGCTAACCAGACAGTTCATGT (SEQ ID NO: 29) | |
| Alg3seq-4 | Tcgtcgtaccgcattgatcct (SEQ ID NO: 30) | |

Example 2

Genetic Inactivation of Alg3 in *A. niger*

This example describes methods used to genetically clone and then inactivate Alg3 in *A. niger* strain 11414KusA. Based on these teachings, one skilled in the art will appreciate that Alg3 can be similarly inactivated in other strains of *Aspergillus*.

Alg3 has been identified and characterized in *Arabidopsis thaliana, Homo sapiens, Pichia pastoris, Trypanosoma brucei* and *Saccharomyces cerevisiae* (see for example Korner et al., *EMBO J.* 18(23): 6816-6822, 1999; Davidson et al., *Glycobiology* 14(5):399-407, 2004; Manthri et al., *Glycobiology* 18(5): 367-383, 2008; Kajiura et al., *Glycobiology* 20(6):736-751, 2010). A database search based on the amino acid sequence of *S. cerevisiae* Alg3 identified a putative α-1,3-mannosyltransferase gene in JGI (DOE Joint Genome Institute)-*A. niger* genome database (jgi|Aspni5|42720). The *A. niger* Alg3 gene contains two introns and its 1400 bp open reading frame (nt 1186-1306, 1393-1916 and 1989-2582 of SEQ ID NO: 1) encodes a protein consisting of 413 amino acids (SEQ ID NO: 2), which contains one potential N-glycosite at the amino acid position 374. The predicted Alg3 amino acid sequence has 39% sequence identity to the *S. cerevisiae* Alg3.

Figure 1A:
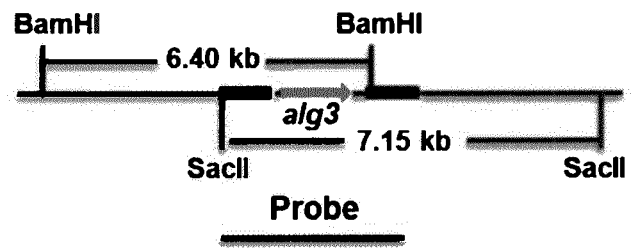
FIG. 1A is a schematic drawing showing a restriction map of the 10.9 kb fragment containing the *A. niger* Alg3 gene.
Figure 1B:
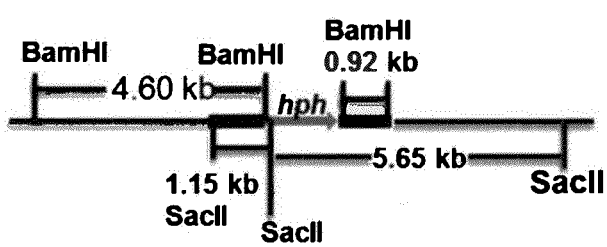
FIG. 1B is a schematic drawing showing the introduction of the hyg-selective marker, which was flanked by the upstream and downstream DNA sequences of Alg3. Integration of the linear molecules by homologous recombination replaces Alg3 with hph in the chromosome.
Figure 1C:
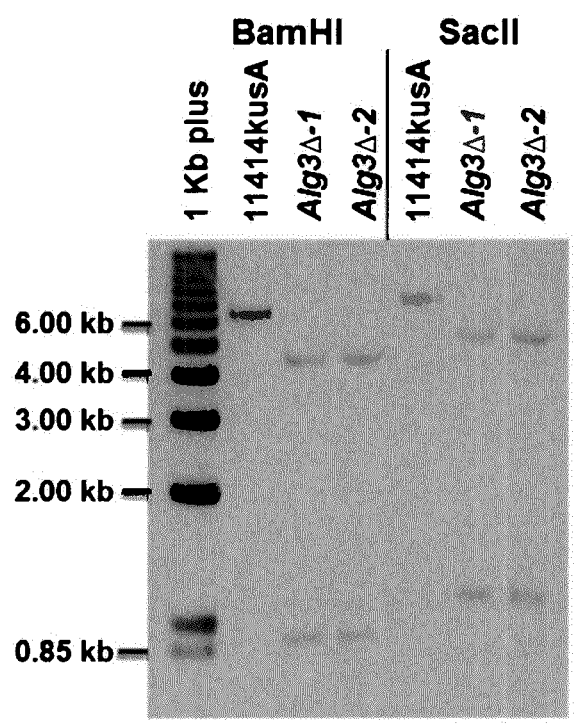
FIG. 1C is a digital image of a Southern blot showing the genomic DNA hybridization of parent and Alg3Δ strains. One parent and two selected Alg3Δ strains are shown, which have the correct enzyme restriction pattern.
Figure 2:
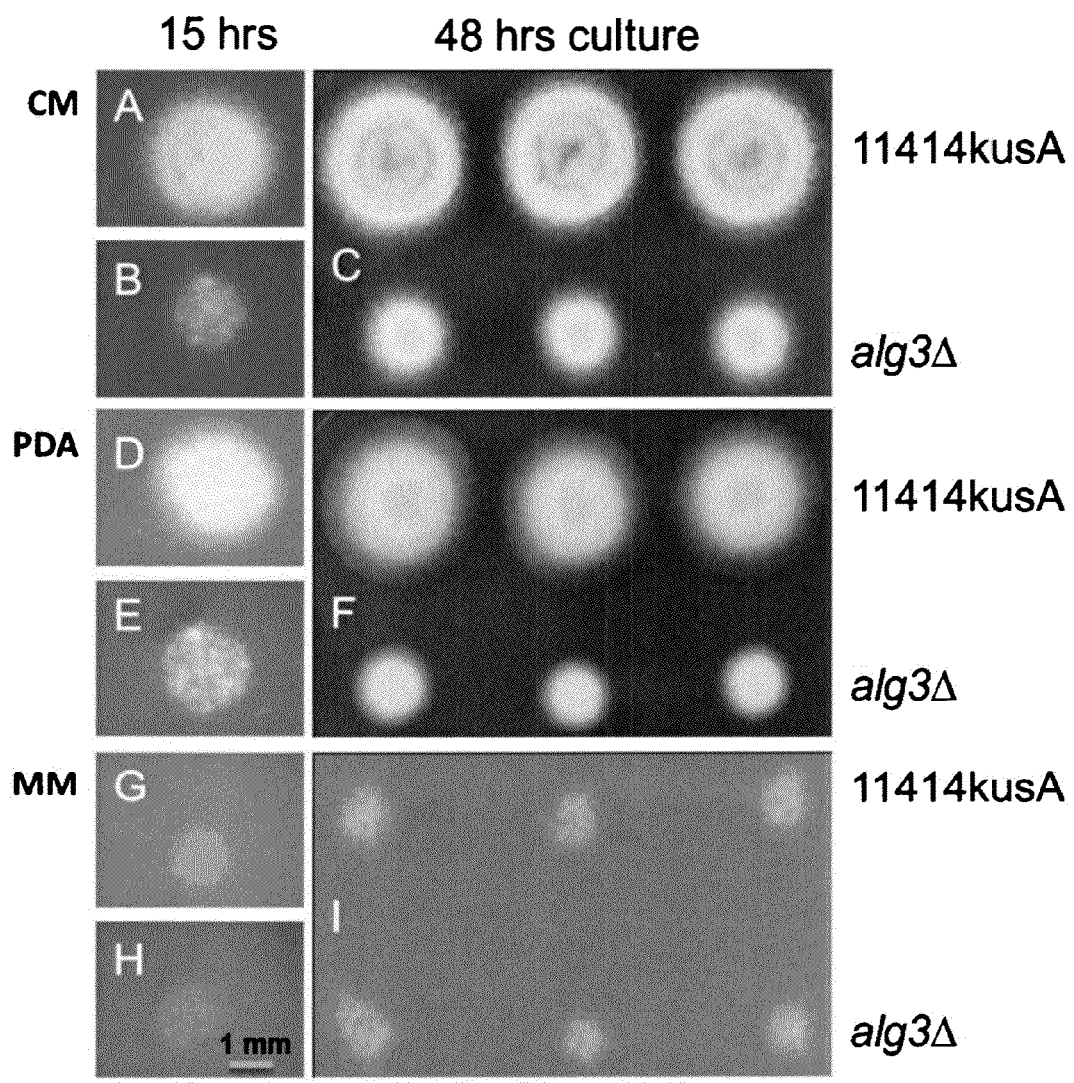
FIGS. 2A-I are digital images showing the Alg3Δ and parent 11414kusA strains grown on agar plates of complete medium (CM), potato dextrose (PDA), and minimal medium (MM) at 30° C. for 15 hrs or 48 hrs. (A) parent strain, (B) Alg3Δ strain, and (C) both parent and Alg3Δ strains grown on complete medium plate. (D) parent strain, (E) Alg3Δ strain, and (F) both parent and Alg3Δ strains were grown on PDA agar plates. (G) parent strain, (H) Alg3Δ strain, and (I) both parent and Alg3Δ strains were grown on MM agar plates.

Alg3 was functionally inactivated in *A. niger* using a gene deletion vector constructed by yeast gap repairing approach. The 5'- and 3'-end of the hygromycin marker (hph) gene was flanked with about 1 kb upstream and downstream fragments of Alg3 coding region that were isolated by PCR from *A. niger* genomic DNA. The DNA sequence of the upstream and downstream fragments was confirmed by DNA sequencing analysis. The Alg3 in *A. niger* was deleted by homologous replacement with hygromycin marker (hph) gene in the kusA deletion background of *A. niger*, where the kusA gene, encoding the ortholog of the Ku70 protein in other eukaryotes, was deleted for dramatically improved homologous integration efficiency. FIGS. 1A and 1B show the predicted restriction enzyme digestion patterns of genomic DNA of the parent and mutant strains with BamHI and SacII. FIG. 1C shows the Southern blotting analysis of the digested genomic DNA of parent and mutant strains. The results confirm that the Alg3 coding region in *A. niger* was replaced by the hygromycin selection marker gene (hph) in the Alg3Δ strains.

Example 3

Effects of Alg3 Deletion on *A. niger* Growth and Development

This example describes methods used to determine the effect genetically inactivating Alg3 in *A. niger*.

It was previously demonstrated that the deletion of Alg3 in different organisms causes underglycosylation, but no obvious phenotype changes were observed at the selected culture condition in those studies (Aebi et al., *Glycobiology* 6(4): 439-444, 1996; Korner et al., *EMBO J.* 18(23): 6816-6822, 1999; Davidson et al., *Glycobiology* 14(5):399-407, 2004;

Manthri et al., *Glycobiology* 18(5): 367-383, 2008; Kajiura et al., *Glycobiology* 20(6):736-751, 2010).

Figure 3A:
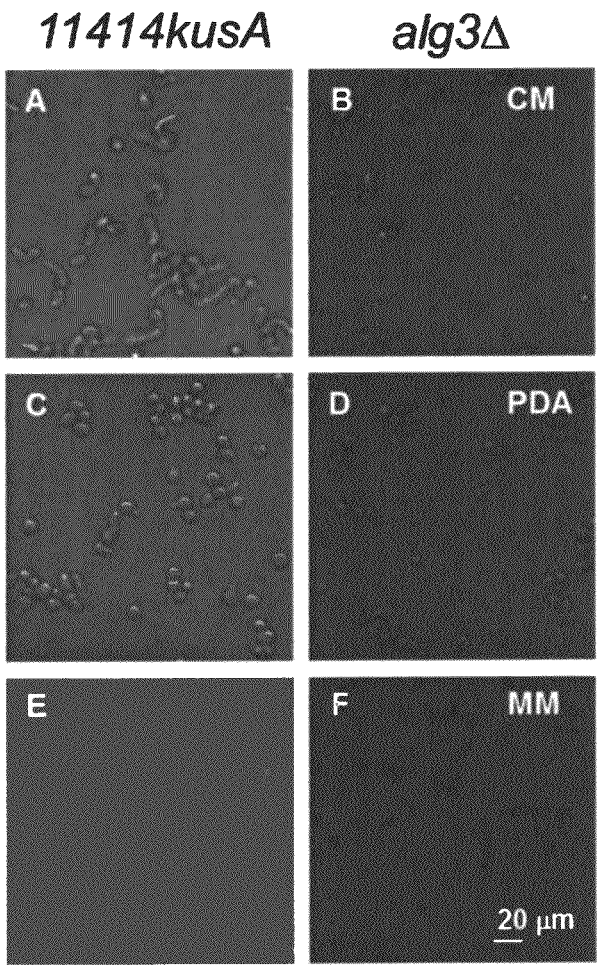
FIG. 3A shows digital images showing the spore germination of parent 11414kusA and Alg3Δ strains in liquid cultures of complete medium (CM), potato dextrose medium (PDA), and minimal medium (MM) at 30° C. for 7 hours. Panels A and B are germinated spores in CM liquid culture. Panels C and D are germinated spores in PDA liquid culture. Panels E and F are germinated spores in MM liquid culture. The left panels for the parent 11414kusA strain and the right panels for the Alg3Δ strain.
Figure 3B:
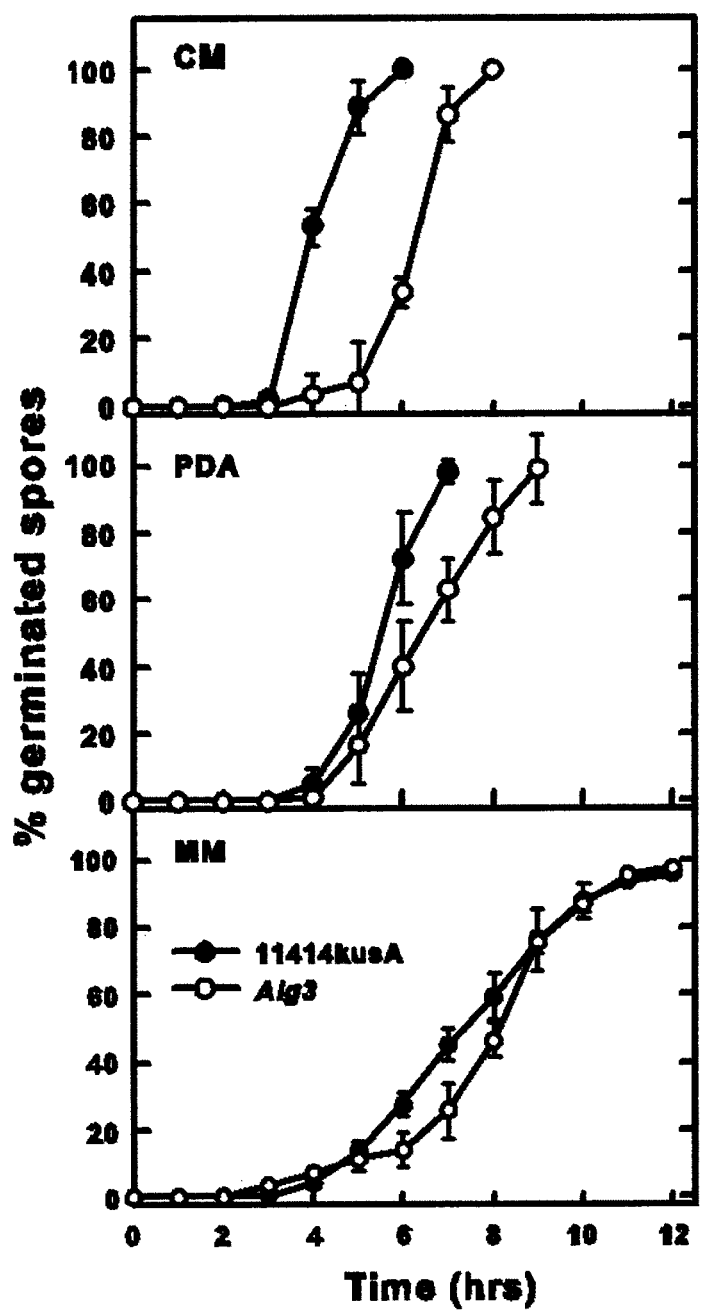
FIG. 3B provides graphs showing the time courses of the percentage of spore germination of parent 11414kusA and Alg3Δ strains grown in the liquid cultures of complete medium (CM; top graph), potato dextrose medium (PDA; middle graph), or minimal medium (MM; bottom graph). The solid filled cycle is the parent 11414kusA strain and open cycle is the Alg3Δ strain.

The effects of the Alg3 deletion were examined on CM, PDA and MM plates. As exhibited in FIGS. 2A-I, the Alg3Δ strain grew much slower than the parent strain when grown on either CM or PDA medium plate, but there was no significant difference between the Alg3Δ mutants and parent strain when grown on the MM medium plate. When both Alg3Δ strain and parent strain were grown in the liquid culture of CM and PDA, the initiation of spore germination of Alg3Δ strain was pronouncedly delayed (FIG. 3A), but the spore germination rate was not affected by the Alg3 deletion (FIG. 3B). These results demonstrate that deletion of Alg3 has significant effects on *A. niger* growth on nutrient rich media.

Figure 4:
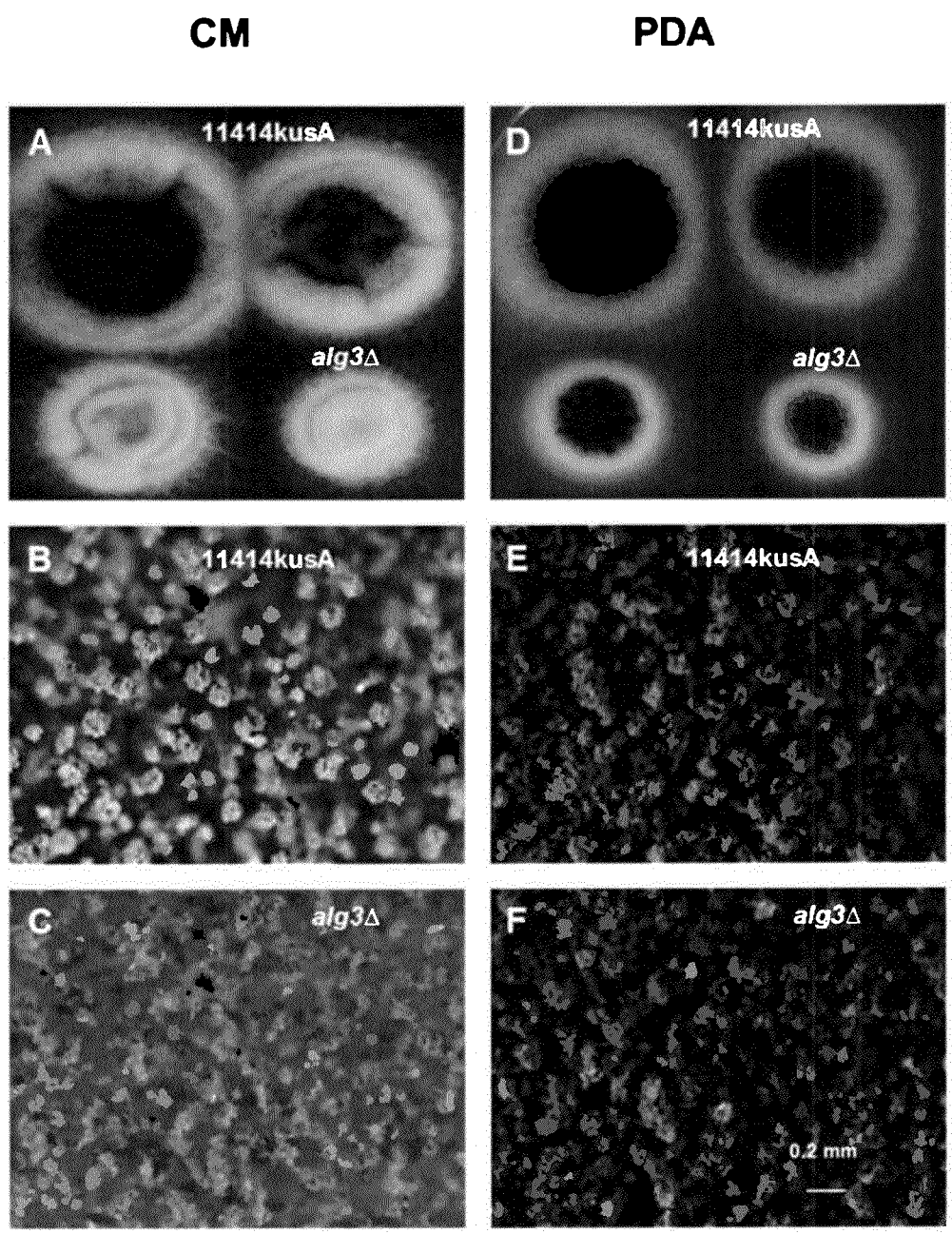
FIG. 4 provides digital images and stereo microscopy digital images of parent and Alg3Δ strains grown on agar plates of complete medium (CM) and potato dextrose (PDA) at 30° C. for 4 days.

The effects of Alg3 deletion on spore production on both CM and PDA plates were also examined. The Alg3 deletion had a substantial reduction of sporulation on CM medium plate, while no obvious difference was exhibited on PDA plate (FIG. 4). The spore production at given area was enumerated with hemocytometer (Table 3). The average spore production of Alg3Δ was $2.64 \times 10^7$ spores/cm$^2$, about 40% of parent strain ($6.44 \times 10^7$ spores/cm$^2$) on CM medium plates, while average spore production per a square millimeter was similar between Alg3Δ mutant ($7.72 \times 10^7$ spores/cm$^2$) and parent strains ($7.89 \times 10^7$ spores/cm$^2$) on PDA medium plates.

TABLE 3

Average spore production in PDA and CM media plates ($\times 10^7$ sp/cm$^2$). This was averaged from four cuts and 3 replicate counting.

| Strain | CM pates | PDA |
|---|---|---|
| 11414-kusA | 6.44 ± 1.24 | 7.72 ± 1.78 |
| Alg3Δ | 2.64 ± 0.49 | 7.89 ± 1.18 |

Example 4

Effects of Alg3 Deletion on Spore Germination, Growth and Citric Acid Production This example describes methods used to measure spore germination, growth, and citric acid production in the Alg3Δ *A. niger* strain generated in Example 1. Based on these teachings, one skilled in the art will appreciate that spore germination, growth, and citric acid production can be similarly measured in other Alg3Δ strains of *Aspergillus*.

*A. niger* strain ATCC11414 is a strain developed for industrial production of citric acid. *A. niger* morphology plays a role in citric acid production. The fungal morphology affect overall molecular regulation in response to the endogenous and exogenous factors, which include the regulations of transcription, post-transcription, translation and post-translation. Therefore, the effects of Alg3 deletion on *A. niger* growth on CAP agar plates at different pHs or in CAP liquid culture conditions was determined.

Figure 5:
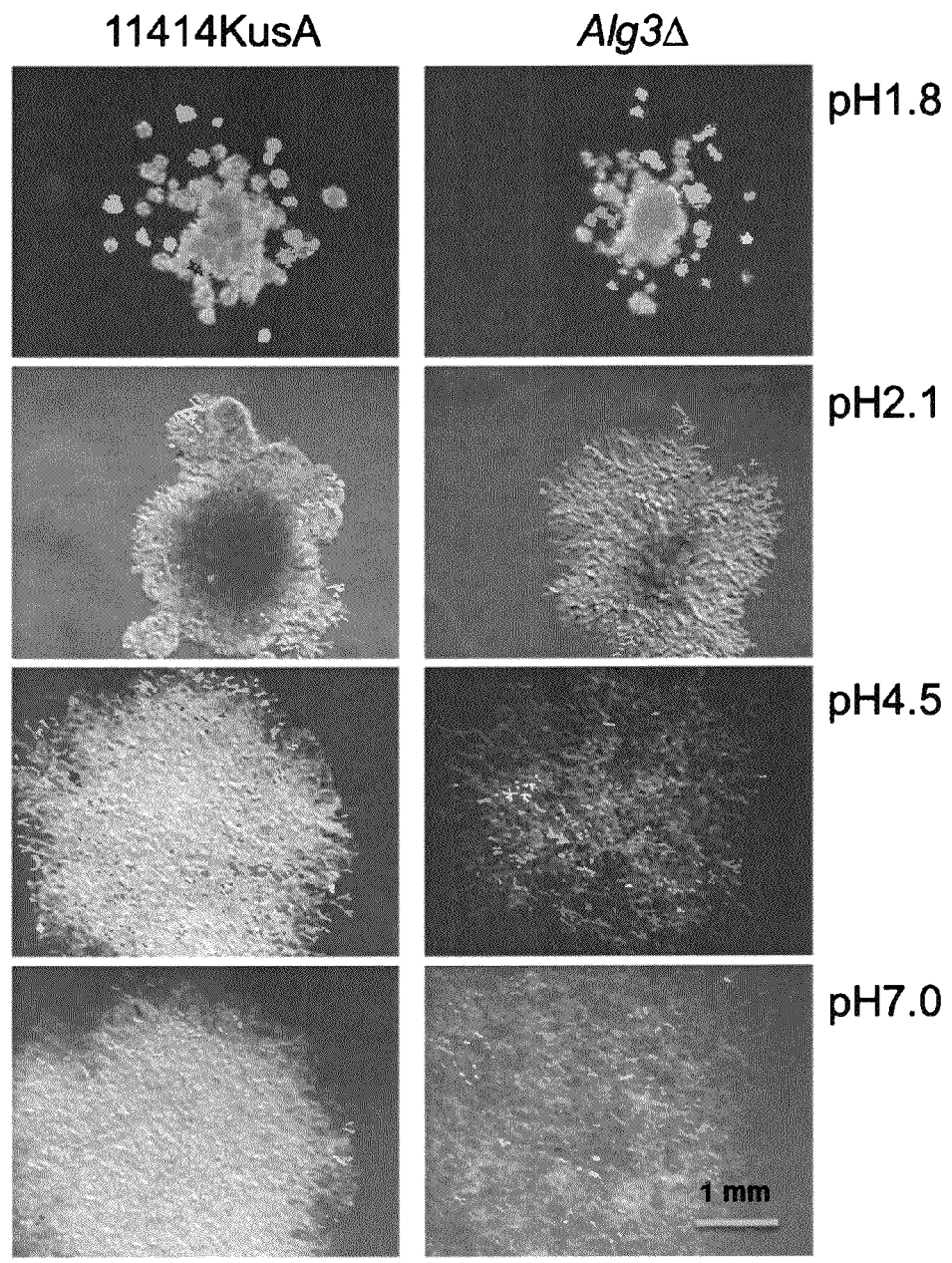
FIG. 5 provides stereo microscopy digital images parent 11414kusA and Alg3Δ strains grown on citric acid production (CAP) medium plates at different pH levels for 27 hrs. The left panels for parent strain 11414kusA and right panels for the Alg3Δ strain.

FIG. 5 shows the effects of Alg3 deletion in fungi grown on CAP medium plates at different pH conditions after 28 hrs in culture. When the Alg3Δ strain was grown on the CAP medium plates at pH 1.8, its growth was relatively slower than the parent strain, where its colonies were much smaller than the parent strain. At pH 2.1, the Alg3Δ strain formed a less tight pellet than that of parent strain. Growth of the Alg3Δ strain on the CAP medium at pH 4.5 and pH 7.0 was affected more profoundly than that of parent strain, where the Alg3Δ strain formed thinner layer of biomass on the agar plates than that of parent strain. These results show that the Alg3 deletion reduces the normal growth of *A. niger* at different levels on CAP culture medium plates at different pHs.

The spore germination of the Alg3Δ and parent strains in CAP liquid culture medium was also examined by using automated microscopic imaging, enumerating the germination manually in a same visual unit area, and expressing spore germination as a percentage of total spores at the same visual unit area. FIG. 6 shows the different dynamics of spore germination between the Alg3Δ and parent strains. The spore germination of Alg3Δ strain began as early as 3 hrs after spore inoculation, while the parent strain was not initiated until 6 hrs after spore inoculation. After 8 hrs inoculation, more than 32% spores of Alg3Δ mutant germinated, while only 10% of parent strain spores did (FIGS. 6A, 6C, 6E). After 15 hrs growth in CAP liquid medium, more than 90% spores of Alg3Δ strain germinated, while only 50% spores of parent strain did (FIGS. 6B, 6D and 6E). After 24 hrs of growth in the liquid culture, about 75% spores of parent strain germinated, while the Alg3Δ strain achieved 94% of germination rate (FIG. 6E). The Alg3 deletion leads to earlier germination and a higher germination rate than parent strain.

Figure 7:
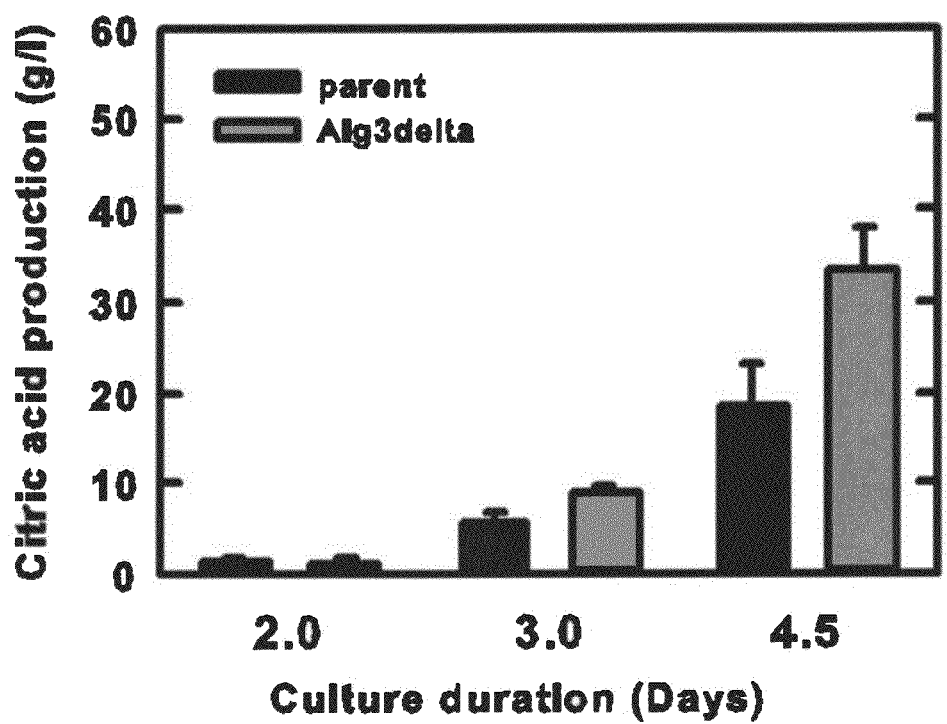
FIG. 7 is a graph showing the time course of citric acid production by parent 11414kusA and Alg3Δ strains in the liquid culture of citric acid production at 30° C. and 200 rmp.

The effect of Alg3 deletion on citric acid production was determined in CAP flask cultures. FIG. 7 shows the time course of citric acid production in CAP liquid medium. The yield of citric acid production was similar between the Alg3Δ mutant and parent strain in 2 days culture. After 3 days culture, the average citric acid production by Alg3Δ mutants was 8.8 g/l citric acid, while the parent strain only produced 5.8 g/l. After 4.5 days of culture, the parent strain accumulated 18.8 g/l citric acid and the Alg3Δ mutant produced 33.3 g/l citric acid (more than 70% higher than the parent strain). Thus, the Alg3 deletion substantially improves the citric acid production in *A. niger*.

The effect of Alg3 deletion on citric acid production was also examined by complementation of its original gene into the alg3Δ mutant. FIG. 8B shows the citric acid production in CAP liquid medium after 10 days of culture. The yield of citric acid production was similar between the alg3Δ complemented (cAlg3Δ) mutant and parent strain, but much lower than the alg3Δ mutant in 10 days culture. After 10 days culture, the average citric acid production by Alg3Δ mutants was 46.1 g/l citric acid, while the parent and calg3Δ strain only produced 34.8 and 29.4 g/l, respectively.

Example 5 pPTRpGPDALaeA Plasmid Vector Construction

This example describes methods used to generate the pPTRpGPDALaeA plasmid vector (FIG. 13). One skilled in the art will appreciate that although gpdA and LaeA sequences were used from *Aspergillus nidulans*, one skilled in the art will appreciate that variants of these sequences can be used in the fungi and methods provided herein, such as gpdA and LaeA sequences from other *Aspergillus* species. In one example, a gpdA sequence having at least 80%, at least 90%, at least 95%, or at least 98% sequence identity to SEQ ID NO: 37 is used in the fungi and methods provided herein.

The *Aspergillus nidulans* glyceraldehyde 3-phosphate dehydrogenase (gpdA) promoter (SEQ ID NO: 37) was isolated from the pAN8-1 plasmid DNA using the primer set gpdA5F/gpdA3R (gpdA5F: CGCAGATCTC AAGCTG-TAAG GATTTCGGCA SEQ ID NO: 38; gpdA3R: CAC-CGGGCCC ATCTCAAACA TTGTGATGTC TGCT-CAAGCG SEQ ID NO: 39) and the LaeA coding sequence of genomic DNA from *A. nidulans* (SEQ ID NO: 40) obtained by PCR using LaeA5F/LaeA3R (LaeA5F: CGCTTGAGCA GACATCACAA TGTTTGAGAT GGGCCCGGTG; SEQ ID NO: 42; LaeA3R: CGCAGATCTG AGGATTATGA GAAGGGAGC; SEQ ID NO: 43).

The DNA fragment of pGPDA and LaeA was filled together by overlap PCR and a HindIII restriction enzyme site was introduced at both 5'- and 3'-end of the DNA fragment. The DNA fragment (SEQ ID NO: 44) and pPTR1 plasmid DNA were cut with Hind III and ligated together by a quick DNA ligation kit at 25° C. for 30 min. The ligated plasmid DNA was transferred into the Top 10 *E. coli* competent cells by lithium acetate mediated transformation. The transformed bacterial colonies were screened for the DNA fragment insertion by PCR with the primers gpdA5F (SEQ ID NO: 38) and LaeA3R (SEQ ID NO: 43). The plasmid DNA for the selected transformed colonies was prepared for restriction enzyme confirmation and further expression vector construction.

Example 6 pRS426-LaeA Vector Construction

Figure 14:
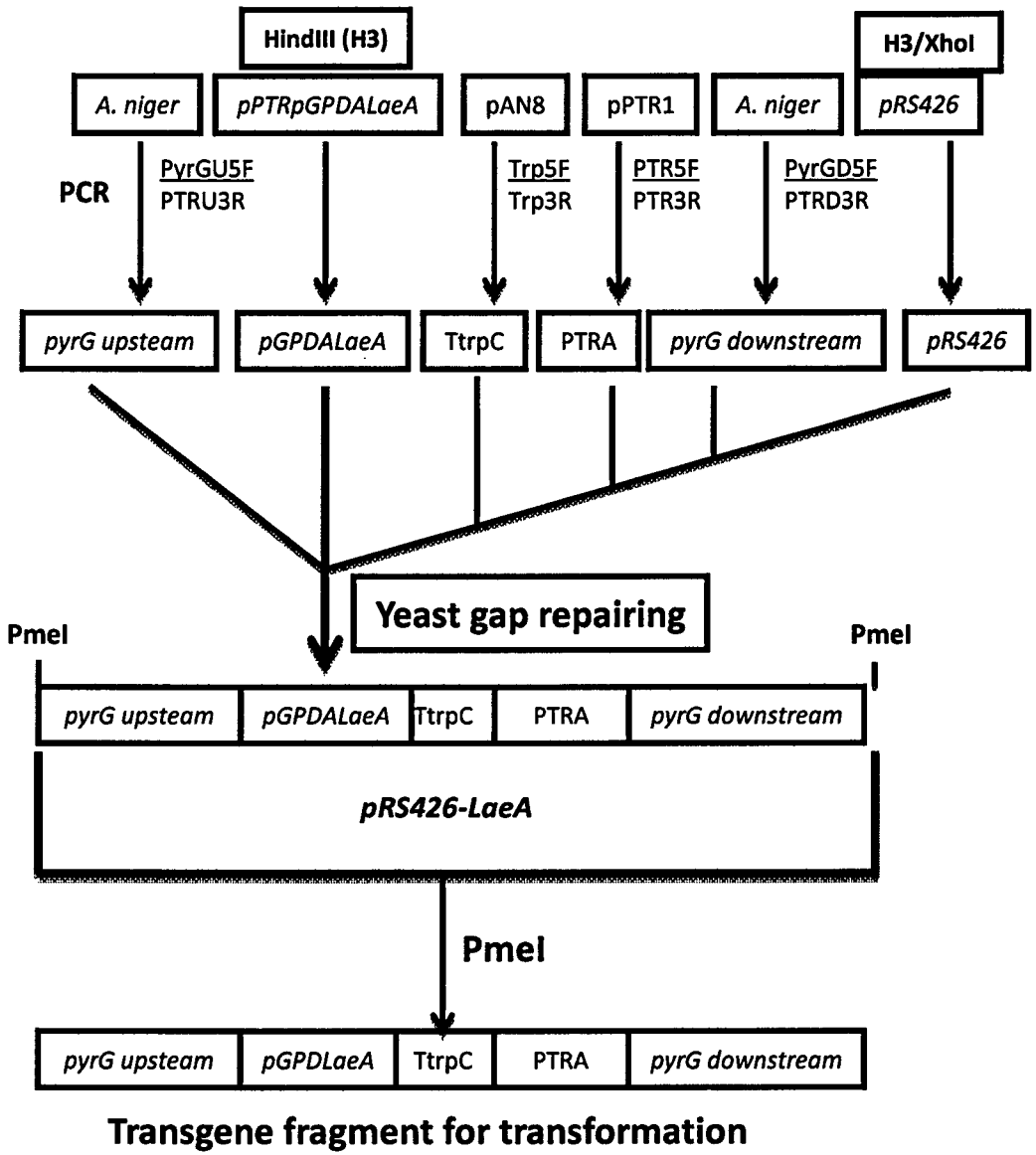
FIG. 14 is schematic illustrating a plasmid vector pRS426-LaeA, which contains the upstream region of pyrG gene of *A. niger*, the coding region of LaeA gene under the control of gpdA promoter and transcriptional terminator of trpC gene from *A. nidulans*, the pyrithiamine resistance (ptrA) gene from *A. oryzae*, and the downstream region of pyrG gene of *A. niger*. The unique restriction enzyme PmeI site was introduced at the both end of transgene expression fragment.

This example describes methods used to generate a transgene containing *A. niger* LaeA (FIG. 14).

PCR was performed to isolate DNA fragments of *A. niger* pyrG upstream region (SEQ ID NO: 45), trpC transcriptional terminator of *A. nidulans* (SEQ ID NO: 46), pyrithiamine resistance gene (ptrA) of *Aspergillus oryzae* (SEQ ID NO: 47), and *A. niger* pyrG downstream region (SEQ ID NO: 48), using primers pyrGU5F/PTRU3R (pyrGU5F: GTAACGC-CAG GGTTTTCCCA GTCACGACGT TAAACATGC ATCATTCTCC CGCTTTGT, SEQ ID NO: 49; pyrGU3R: TGCCGAAATC CTTACAGCTT GAAGCTTCAT CGC-CAATCAC CTCAATCAC, SEQ ID NO: 50), Trp5F/Trp3R (Trp5F: AGCTCCCTTC TCATAATCCT CAAGCTTGGA CCGATGGCTG TGTAGAAGT, SEQ ID NO: 51; Trp3R: CGTAATCAAT TGCCCGTCTG TCAGAGAGCG GATTC-CTCAG TCTCGT; SEQ ID NO: 52), PTR5F/PTR3R (PTR5F: ACGAGACTGA GGAATCCGCT CTCTGA-CAGA CGGGCAATTG ATTACG, SEQ ID NO: 53; PTR3R: ACAGCAGTGC TTATCTGCGA TGACGAGCCG CTCT-TGCATC TTTGT, SEQ ID NO: 54) and PyrGD5F/PTRD3R (pyrGD5F: ACAAAGATGC AAGAGCGGCT CGT-CATCGCA GATAAGCACT GCTGT; SEQ ID NO: 55, pyrGD3R: TGAGACGCTG TTTCACCGAG TACATCGCCA ATCACCTCAA TCAC, SEQ ID NO: 56), respectively.

As shown in FIG. 14, the DNA fragment of pGDPALaeA (SEQ ID NO: 44) was isolated from pPTRpGDPALaeA (FIG. 13) by HindIII digestion. The yeast gap repairing vector pRS426 was double digested with restriction enzyme HindIII and XhoI. Hundred nanograms of each DNA fragment generated from PCR (i.e., SEQ ID NOS: 45-56) or restriction enzyme digestions were used for *S. cerevisiae* transformation. The gap repairing plasmid DNA in the total *S. cerevisiae* genomic DNA was isolated by transferred into the Top 10 *E. coli* cells.

The transformed plasmid DNA was confirmed by PCR and digested with PmeI. The PmeI DNA fragment (SEQ ID NO: 57) was used for *A. niger* transformation.

One skilled in the art will appreciate that although the pyrG upstream and downstream sequences, trpC transcriptional terminator sequence, and ptrA sequence used were from particular organisms, one skilled in the art will appreciate that variants of these sequences can be used in the fungi and methods provided herein, such as those from other *Aspergillus* species. In one example, pyrG upstream and downstream sequences having at least 80%, at least 90%, at least 95%, or at least 98% sequence identity to SEQ ID NO: 45 and 48 are used in the fungi and methods provided herein. In one example, a trpC transcriptional terminator sequence having at least 80%, at least 90%, at least 95%, or at least 98% sequence identity to SEQ ID NO: 46 is used in the fungi and methods provided herein. In one example, a ptrA sequence having at least 80%, at least 90%, at least 95%, or at least 98% sequence identity to SEQ ID NO: 47 is used in the fungi and methods provided herein.

Example 7

Expression of pGDPALaeA-Containing Transgene in *A. niger*

This example describes methods used to introduce pGP-DALaeA (SEQ ID NO: 57) into *A. niger*.

The originally transformed *A. niger* colonies were picked from the minimal medium plates with 0.1 μg/ml pyrithiamine hydrobromide selection on minimal medium agar plates without thiamine supplementation. The single spore colonies were picked for spore production after the initial transformant spores were grown on the same selection medium plates. The biomass was harvested from the single spore colony isolates grown in minimal medium with pyrithiamine selection and dried in the VirTis bench top freeze dryer. The genomic DNA was prepared for PCR confirmation of pGDPALaeA insertion in transgenic *A. niger*. As shown in FIG. 15A, the primer set of PTR5F (SEQ ID NO: 53) and PTR3R (SEQ ID NO: 54) was used to confirm the presence of *A. oryzae* pyrithiamine resistance gene (ptrA) in transgenic *A. niger* with the expected size of 2 kb PCR DNA fragment. As shown in FIG. 15B, the primer set LaeA5F (SEQ ID NO: 42) and TRP3R (SEQ ID NO: 52) was used to demonstrate that the transgene *A. nidulans* LaeA was under the control of gdpA promoter and trpC transcriptional terminator of *A. nidulans* with the expected 3.4 kb PCR fragment size. The genomic DNA of parent strain and the plasmid DNA of transgene vector carrying the pGDPALaeA fragment were used for negative and positive references.

Example 8

Increased Production of Citric Acid

This example describes methods used to demonstrate that citric acid production was increased in the presence of increased expression of LaeA, alone or in combination with deletion of Alg3.

Citric acid was produced as described in Example 1.

Figure 16:
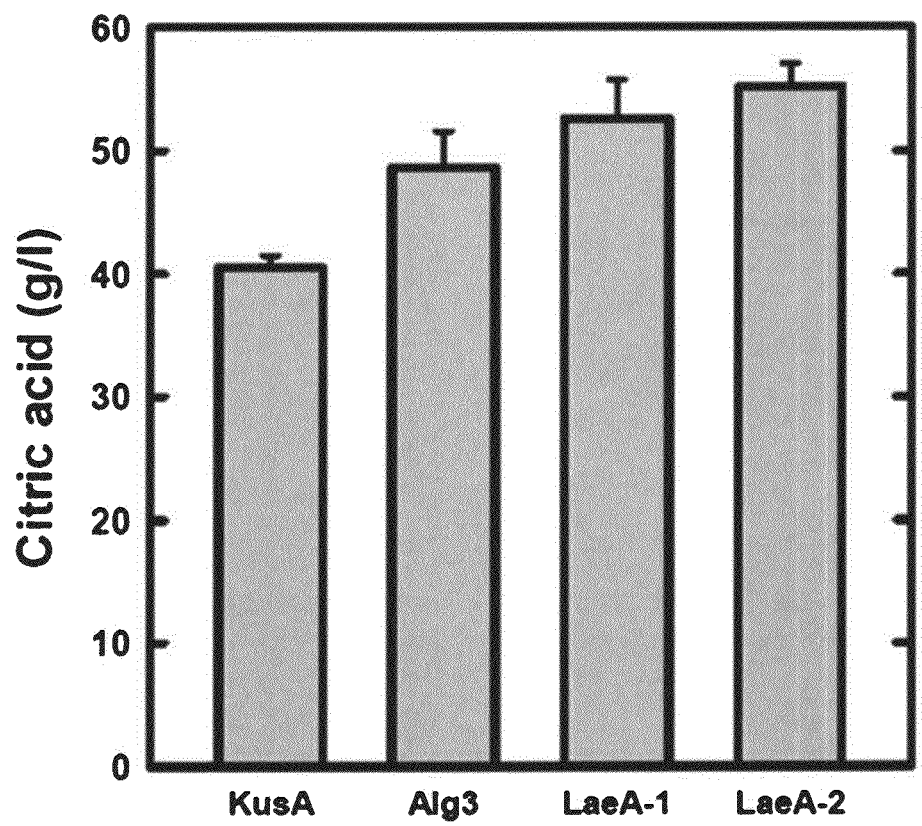
FIG. 16 is a bar graph showing the results of citric acid production after 10 days in culture of parent strain (kusA), alg3Δ mutant (Alg3), and over-expression of LaeA gene in alg3Δ (LaeA-1 and LaeA-2) mutants. The data for each strain is the average of three replicates.

As shown in FIG. 16, of citric acid production was increased in the Alg3Δ mutant (Alg3), and in the mutants over-expressing LaeA in Alg3Δ (LaeA-1 and LaeA-2), as compared to the parent strain (kusA).

In view of the many possible embodiments to which the principles of the disclosed invention may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. An isolated fungus comprising a genetic inactivation of an endogenous dolichyl-P-Man:Man(5)GlcNAc(2)-PP-dolichyl mannosyltransferase (Alg3) gene, wherein the fungus is an *Aspergillus* species and the Alg3 gene is genetically inactivated by complete or partial deletion mutation or by insertional mutation, wherein the endogenous Alg3 gene prior to the genetic inactivation encodes a protein having at least 80% sequence identity to the polypeptide of SEQ ID NO: 2 or 4.

2. The isolated fungus of claim 1, wherein said fungus has been transformed with at least one *Aspergillus* LaeA (loss of aflR expression A) gene, wherein said LaeA gene encodes a protein having at least 80% sequence identity to the polypeptide of SEQ ID NO: 41 or 59.

3. The isolated fungus of claim 1, wherein the *Aspergillus* species is *Aspergillus niger* (*A. niger*).

4. The isolated fungus of claim 3, wherein the *A. niger* is *A. niger* strain American Type Culture Collection (ATCC) 11414 or *A. niger* strain 11414KusA.

5. An isolated fungus comprising a genetic inactivation of an endogenous dolichyl-P-Man:Man(5)GlcNAc(2)-PP-dolichyl mannosyltransferase (Alg3) gene, wherein the fungus is an *Aspergillus* species and the Alg3 gene is genetically inactivated by complete or partial deletion mutation or by insertional mutation, wherein the endogenous Alg3 gene prior to the genetic inactivation has at least 80% sequence identity to the polynucleotide of SEQ ID NO: 1 or 3.

6. The isolated fungus of claim 1, wherein said fungus has been transformed with at least one *Aspergillus* LaeA (loss of aflR expression A) gene, wherein said LaeA gene has at least 80% sequence identity to (a) nucleotides 1-236 and 367-1252 of SEQ ID NO: 40, or (b) nucleotides 1-230 and 373-1267 of SEQ ID NO: 58.

7. The isolated fungus of claim 1, wherein compared to the parental *Aspergillus* strain having a wild-type Alg3 gene and cultured under the same conditions, the fungus:
grows slower on citric acid production medium;
has earlier spore germination in citric acid production medium;
produces at least 20% more citric acid when grown in citric acid production medium;
grows slower on complete medium or potato dextrose medium;
has reduced sporulation on complete medium; and/or
accumulates red color pigments on complete medium.

8. The isolated fungus claim 1, wherein:
8 hours after inoculation in citric acid production medium, at least 30% of spores from the fungus have germinated compared to about 10% of spores from the parental *Aspergillus* strain having a wild type Alg3 gene when grown in the same citric acid production medium under the same conditions;
15 hours after inoculation in citric acid production medium, at least 90% of spores from the fungus have germinated compared to about 50% of spores from the parental *Aspergillus* strain having a wild type Alg3 gene when grown in the same citric acid production medium under the same conditions; and/or
initiation of spore germination by the fungus is delayed relative to the parental *Aspergillus* strain having a wild-type Alg3 gene in complete medium or potato dextrose medium, wherein the fungus and the parental strain are cultured under the same conditions.

9. The isolated fungus of claim 7, wherein the citric acid production medium comprises 140 g/l of glucose, 3.1 g/l $NH_4NO_3$, 0.15 g/l $KH_2PO_4$, 0.15 g/l NaCl, 2.2 g/l $MgSO_4.7H_2O$, 6.6 mg/l $ZnSO_4.7H_2O$, 0.1 mg/l $FeCl_3$, and 10 ppb $Mn^{2+}$, wherein the pH of the citric acid production medium is adjusted to pH 2 with 4 M $H_2SO_4$.

10. A composition comprising the isolated fungus of claim 1.

11. A kit, comprising:
the fungus of claim 1; and
a medium for culturing the fungus.

12. A fermentation broth comprising the fungus claim 1.

13. A method of making citric acid, comprising:
culturing the isolated fungus of claim 1 under conditions that permit the fungus to make citric acid; thereby making citric acid.

14. The method of claim 13, wherein the fungus is cultured in media comprising at least 50 g/l sugar and 8 to 15 ppb manganese.

15. The method of claim 13, further comprising isolating the citric acid made by culturing the fungus.

16. The isolated fungus of claim 1, wherein prior to genetic inactivation, the Alg3 gene encodes the protein of SEQ ID NO: 2 or SEQ ID NO: 4.

17. The isolated fungus of claim 2, wherein the *Aspergillus* LaeA gene encodes a protein comprising SEQ ID NO: 41 or SEQ ID NO: 59.

18. The isolated fungus of claim 2, wherein the *Aspergillus* LaeA gene comprises (a) nucleotides 1-236 and 367-1252 of SEQ ID NO: 40, or (b) nucleotides 1-230 and 373-1267 of SEQ ID NO: 58.

19. An isolated fungus, comprising a genetic inactivation of an endogenous dolichyl-P-Man:Man(5)GlcNAc(2)-PP-dolichyl mannosyltransferase (Alg3) gene, wherein the Alg3 gene is genetically inactivated by complete or partial deletion mutation or by insertional mutation, and wherein prior to genetic inactivation, the Alg3 gene encodes the protein of SEQ ID NO: 2 or SEQ ID NO: 4.

20. The isolated fungus of claim 19, wherein the fungus is transformed with a nucleic acid molecule encoding the protein of SEQ ID NO: 41 or SEQ ID NO: 59.

* * * * *

UNITED STATES PATENT AND TRADEMARK OFFICE
CERTIFICATE OF CORRECTION

| | | |
|---|---|---|
| PATENT NO. | : 9,023,637 B2 | Page 1 of 1 |
| APPLICATION NO. | : 13/691396 | |
| DATED | : May 5, 2015 | |
| INVENTOR(S) | : Dai et al. | |

It is certified that error appears in the above-identified patent and that said Letters Patent is hereby corrected as shown below:

In the Specification:

Column 1, following line 12, ACKNOWLEDGMENT OF GOVERNMENT SUPPORT should be added and should read –This invention was made with government support under contract number DE-AC05-76RLO1830 awarded by the U.S. Department of Energy. The government has certain rights in the invention.–

In the Claims:

Column 108, line 34, "fungus claim" should read –fungus of claim–

Column 108, line 38, "wild type" should read –wild-type–

Column 108, line 44, "wild type" should read –wild-type–

Column 108, line 55, "$MgSO_4.7H_2O$, 6.6 mg/l $ZnSO_4.7H_2O$" should read –$MgSO_4 \cdot 7H_2O$, 6.6 mg/l $ZnSO_4 \cdot 7H_2O$–

Column 108, line 63, "fungus claim" should read –fungus of claim–

Signed and Sealed this
First Day of March, 2016

Michelle K. Lee
*Director of the United States Patent and Trademark Office*